United States Patent
LaVon et al.

(10) Patent No.: US 10,993,851 B2
(45) Date of Patent: May 4, 2021

(54) HIP-TO-WAIST AND WAIST-TO-CROTCH SILHOUETTE(S) OF ABSORBENT ARTICLE(S) COMPRISING BEAMED ELASTICS

(71) Applicant: The Procter & Gamble Company, Cincinnati, OH (US)

(72) Inventors: Gary Dean LaVon, Liberty Township, OH (US); Bret Darren Seitz, Cincinnati, OH (US); Uwe Schneider, West Chester, OH (US); Sarah Marie Wade, Springfield Township, OH (US); Joseph Allen Eckstein, Sunman, IN (US)

(73) Assignee: The Procter & Gamble Company, Cincinnati, OH (US)

(*) Notice: Subject to any disclaimer, the term of this patent is extended or adjusted under 35 U.S.C. 154(b) by 412 days.

(21) Appl. No.: 15/846,433

(22) Filed: Dec. 19, 2017

(65) Prior Publication Data

US 2018/0168876 A1    Jun. 21, 2018

Related U.S. Application Data

(60) Provisional application No. 62/436,589, filed on Dec. 20, 2016, provisional application No. 62/483,965, (Continued)

(51) Int. Cl.
*A61F 13/49*     (2006.01)
*A61F 13/15*     (2006.01)
(Continued)

(52) U.S. Cl.
CPC .... *A61F 13/4902* (2013.01); *A61F 13/15593* (2013.01); *A61F 13/49061* (2013.01);
(Continued)

(58) Field of Classification Search
CPC .......... A61F 13/15593; A61F 13/51478; A61F 13/51464; A61F 13/491; A61F 13/49061;
(Continued)

(56) References Cited

U.S. PATENT DOCUMENTS 3,113,225 A    12/1963   Kleesattel et al.
3,434,189 A     3/1969   Buck et al.
(Continued)

FOREIGN PATENT DOCUMENTS

CA    2158790    3/1996
CN    1276196    6/1999
(Continued)

OTHER PUBLICATIONS

ATSM International Designation: D4910/D4910M—08 (Reapproved 2013) Standard Tables of Body Measurements for Children, Infant Sizes—Preemie to 24 Months (Year: 2013).*
(Continued)

*Primary Examiner* — Susan S Su
(74) *Attorney, Agent, or Firm* — Charles R. Matson; Richard L. Alexander

(57) ABSTRACT

The present disclosure relates to absorbent articles comprising belts comprising one or more pluralities of tightly spaced (less than 4 mm, less than 3 mm, less than 2 mm, and less than 1 mm) and/or low decitex (less than 300, less than 200, less than 100 dtex) and/or low strain (less than 300%, less than 200%, less than 100%) elastics to deliver low pressure less than 1 psi (according to the conditions defined by the Pressure-Under-Strand Test in the Method below) under the elastics, while providing adequate modulus of (between about 2 gf/mm and 15 gf/mm), resulting in a Product Hip-to-Waist Silhouette from about 0.8 to about 1.1 and a Product Waist-to-Crotch Silhouette from about 0.8 to about 2.0 to provide for the advantages described above.

20 Claims, 36 Drawing Sheets

Related U.S. Application Data filed on Apr. 11, 2017, provisional application No. 62/553,149, filed on Sep. 1, 2017, provisional application No. 62/553,171, filed on Sep. 1, 2017, provisional application No. 62/553,538, filed on Sep. 1, 2017, provisional application No. 62/581,278, filed on Nov. 3, 2017.

(51) Int. Cl.

| | | |
|---|---|---|
| B32B 27/12 | (2006.01) | |
| D01F 6/04 | (2006.01) | |
| D01D 5/08 | (2006.01) | |
| B29C 65/08 | (2006.01) | |
| B29C 65/48 | (2006.01) | |
| B29L 31/48 | (2006.01) | |
| B05C 1/08 | (2006.01) | |
| B32B 37/14 | (2006.01) | |
| B65H 39/16 | (2006.01) | |
| B65H 51/30 | (2006.01) | |
| B29C 65/00 | (2006.01) | |
| B29C 65/74 | (2006.01) | |
| B29K 701/12 | (2006.01) | |
| A61F 13/53 | (2006.01) | |
| A61F 13/64 | (2006.01) | |
| A61F 13/84 | (2006.01) | |
| B32B 5/04 | (2006.01) | |
| B32B 37/00 | (2006.01) | |
| B32B 37/12 | (2006.01) | |
| D04H 3/12 | (2006.01) | |
| A61F 13/56 | (2006.01) | |
| B32B 37/22 | (2006.01) | |
| A61F 13/513 | (2006.01) | |

(52) U.S. Cl.
CPC ... *A61F 13/15601* (2013.01); *A61F 13/15699* (2013.01); *A61F 13/15739* (2013.01); *A61F 13/15764* (2013.01); *A61F 13/49012* (2013.01); *A61F 13/49015* (2013.01); *A61F 13/49017* (2013.01); *A61F 13/49019* (2013.01); *A61F 13/53* (2013.01); *A61F 13/5622* (2013.01); *A61F 13/64* (2013.01); *A61F 2013/1591* (2013.01); *A61F 2013/15292* (2013.01); *A61F 2013/15373* (2013.01); *A61F 2013/15406* (2013.01); *A61F 2013/15447* (2013.01); *A61F 2013/15552* (2013.01); *A61F 2013/15869* (2013.01); *A61F 2013/15918* (2013.01); *A61F 2013/15959* (2013.01); *A61F 2013/49022* (2013.01); *A61F 2013/49025* (2013.01); *A61F 2013/49026* (2013.01); *A61F 2013/49074* (2013.01); *A61F 2013/49092* (2013.01); *A61F 2013/49093* (2013.01); *A61F 2013/51322* (2013.01); *A61F 2013/530343* (2013.01); *A61F 2013/8497* (2013.01); *B05C 1/0808* (2013.01); *B29C 65/08* (2013.01); *B29C 65/086* (2013.01); *B29C 65/48* (2013.01); *B29C 65/74* (2013.01); *B29C 66/01* (2013.01); *B29C 66/344* (2013.01); *B29C 66/8141* (2013.01); *B29C 66/83411* (2013.01); *B29K 2701/12* (2013.01); *B29K 2995/0046* (2013.01); *B29L 2031/4878* (2013.01); *B32B 5/04* (2013.01); *B32B 27/12* (2013.01); *B32B 37/0053* (2013.01); *B32B 37/12* (2013.01); *B32B 37/144* (2013.01); *B32B 37/22* (2013.01); *B32B 2305/20* (2013.01); *B32B 2307/51* (2013.01); *B32B 2307/726* (2013.01); *B32B 2555/02* (2013.01); *B65H 39/16* (2013.01); *B65H 51/30* (2013.01); *C08J 2300/26* (2013.01); *D01D 5/08* (2013.01); *D01F 6/04* (2013.01); *D04H 3/12* (2013.01)

(58) Field of Classification Search
CPC .... A61F 13/15; A61F 13/64; A61F 13/55115; A61F 13/493; A61F 13/49017; A61F 13/511; A61F 13/4902; A61F 13/49014; B32B 37/22; B32B 37/12; B32B 37/0053; B32B 7/12; B32B 5/04; B32B 5/022; D04H 3/12; D01F 6/62

See application file for complete search history.

(56) References Cited

U.S. PATENT DOCUMENTS

| | | |
|---|---|---|
| 3,508,722 A | 4/1970 | Kohl |
| 3,562,041 A | 2/1971 | Robertson |
| 3,575,782 A | 4/1971 | Hansen |
| 3,733,238 A | 5/1973 | Long et al. |
| 3,860,003 A | 1/1975 | Buell |
| 3,871,378 A | 3/1975 | Duncan et al. |
| 4,251,587 A | 2/1981 | Mimura et al. |
| 4,333,979 A | 6/1982 | Sciaraffa et al. |
| 4,525,905 A | 7/1985 | Bogucki-Land |
| 4,610,678 A | 9/1986 | Weisman et al. |
| 4,640,859 A | 2/1987 | Hansen et al. |
| 4,657,539 A * | 4/1987 | Hasse .............. A61F 13/4942 604/385.25 |
| 4,673,402 A | 6/1987 | Weisman et al. |
| 4,695,278 A | 9/1987 | Lawson |
| 4,704,115 A | 11/1987 | Buell |
| 4,741,941 A | 5/1988 | Englebert et al. |
| 4,776,911 A | 10/1988 | Uda et al. |
| 4,795,454 A | 1/1989 | Dragoo |
| 4,834,735 A | 5/1989 | Alemany et al. |
| 4,854,984 A | 8/1989 | Ball et al. |
| 4,888,231 A | 12/1989 | Angstadt |
| 4,909,803 A | 3/1990 | Aziz et al. |
| 4,940,464 A | 7/1990 | Van Gompel et al. |
| 4,984,584 A | 1/1991 | Hansen et al. |
| 5,003,676 A | 4/1991 | McFalls |
| 5,060,881 A | 10/1991 | Bogucki-Land |
| 5,092,861 A | 3/1992 | Nomura et al. |
| 5,110,403 A | 5/1992 | Ehlert |
| 5,167,897 A | 12/1992 | Weber et al. |
| 5,246,433 A | 9/1993 | Hasse et al. |
| 5,334,289 A | 8/1994 | Trokhan et al. |
| 5,342,341 A | 8/1994 | Igaue et al. |
| 5,360,420 A | 11/1994 | Cook et al. |
| 5,393,360 A | 2/1995 | Bridges et al. |
| 5,413,849 A | 5/1995 | Austin et al. |
| 5,514,523 A | 5/1996 | Trokhan et al. |
| 5,531,729 A | 7/1996 | Coles et al. |
| 5,558,658 A | 9/1996 | Menard et al. |
| 5,562,646 A | 10/1996 | Goldman et al. |
| 5,569,234 A | 10/1996 | Buell et al. |
| 5,575,874 A | 11/1996 | Griesbach, III et al. |
| 5,599,335 A | 2/1997 | Goldman et al. |
| 5,599,420 A | 2/1997 | Yeo et al. |
| 5,628,097 A | 5/1997 | Benson et al. |
| 5,643,588 A | 7/1997 | Roe et al. |
| 5,643,653 A | 7/1997 | Griesbach, III et al. |
| 5,669,894 A | 9/1997 | Goldman et al. |
| 5,674,216 A | 10/1997 | Buell et al. |
| 5,702,551 A | 12/1997 | Huber et al. |
| 5,775,380 A | 7/1998 | Roelstraete et al. |
| 5,827,259 A * | 10/1998 | Laux .............. A61F 13/49011 604/385.29 |
| 5,858,504 A | 1/1999 | Steven |
| 5,887,322 A | 3/1999 | Hartzheim et al. |
| 5,895,623 A | 4/1999 | Trokhan et al. |
| 5,897,545 A | 4/1999 | Kline et al. |
| 5,916,661 A | 6/1999 | Benson et al. |
| 5,957,908 A | 9/1999 | Kline et al. |
| 5,968,025 A | 10/1999 | Roe et al. |

(56) References Cited

U.S. PATENT DOCUMENTS

| | | | |
|---|---|---|---|
| 5,993,433 A | 11/1999 | St Louis et al. |
| 5,997,521 A | 12/1999 | Robles et al. |
| 6,036,796 A | 3/2000 | Halbert et al. |
| 6,043,168 A | 3/2000 | Colman et al. |
| 6,107,537 A | 8/2000 | Elder et al. |
| 6,107,539 A | 8/2000 | Palumbo et al. |
| 6,118,041 A | 9/2000 | Roe et al. |
| 6,120,487 A | 9/2000 | Ashton |
| 6,120,489 A | 9/2000 | Johnson et al. |
| 6,139,941 A | 10/2000 | Jankevics et al. |
| 6,153,209 A | 11/2000 | Vega et al. |
| 6,248,195 B1 | 6/2001 | Schmitz |
| 6,248,197 B1 | 6/2001 | Nakanishi et al. |
| 6,291,039 B1 | 9/2001 | Combe et al. |
| 6,319,239 B1 | 11/2001 | Daniels et al. |
| 6,383,431 B1 | 5/2002 | Dobrin et al. |
| 6,395,957 B1 | 5/2002 | Chen et al. |
| 6,410,129 B2 | 6/2002 | Zhang et al. |
| 6,426,444 B2 | 7/2002 | Roe et al. |
| 6,475,600 B1 | 11/2002 | Morman et al. |
| 6,478,785 B1 | 11/2002 | Ashton et al. |
| 6,482,191 B1 | 11/2002 | Roe et al. |
| 6,508,641 B1 | 1/2003 | Kubik |
| 6,545,197 B1 | 4/2003 | Muller et al. |
| 6,554,815 B1 | 4/2003 | Umebayashi |
| 6,586,652 B1 | 7/2003 | Roe et al. |
| 6,617,016 B2 | 9/2003 | Zhang et al. |
| 6,627,787 B1 | 9/2003 | Roe et al. |
| 6,632,504 B1 | 10/2003 | Gillespie et al. |
| 6,645,330 B2 | 11/2003 | Pargass et al. |
| 6,673,418 B1 | 1/2004 | DeOlivera et al. |
| 6,676,054 B2 | 1/2004 | Heaney et al. |
| 6,702,798 B2 * | 3/2004 | Christoffel ........ A61F 13/55115 604/385.01 |
| 6,790,798 B1 | 9/2004 | Suzuki et al. |
| 6,821,301 B2 | 11/2004 | Azuse et al. |
| 6,825,393 B2 | 11/2004 | Roe et al. |
| 6,861,571 B1 | 3/2005 | Roe et al. |
| 7,008,685 B2 | 3/2006 | Groitzsch et al. |
| 7,118,558 B2 | 10/2006 | Wu et al. |
| 7,465,367 B2 | 12/2008 | Day |
| 7,569,039 B2 | 8/2009 | Matsuda et al. |
| 7,582,348 B2 | 9/2009 | Ando et al. |
| 7,642,398 B2 | 1/2010 | Järpenberg et al. |
| 7,708,849 B2 | 5/2010 | McCabe |
| 7,777,094 B2 | 8/2010 | Mori et al. |
| 7,861,756 B2 | 1/2011 | Jenquin et al. |
| 7,878,447 B2 | 2/2011 | Hartzheim |
| 7,901,393 B2 | 3/2011 | Matsuda et al. |
| 7,905,446 B2 | 3/2011 | Hartzheim |
| 7,954,213 B2 | 6/2011 | Mizutani et al. |
| 8,093,161 B2 | 1/2012 | Bansal et al. |
| 8,143,177 B2 | 3/2012 | Noda et al. |
| 8,186,296 B2 | 5/2012 | Brown et al. |
| 8,226,625 B2 | 7/2012 | Turner et al. |
| 8,308,706 B2 | 11/2012 | Fukae |
| 8,377,554 B2 | 2/2013 | Martin et al. |
| 8,388,594 B2 | 3/2013 | Turner et al. |
| 8,440,043 B1 | 5/2013 | Schneider et al. |
| 8,585,666 B2 | 11/2013 | Weisman et al. |
| 8,647,319 B2 | 2/2014 | Een et al. |
| 8,729,332 B2 | 5/2014 | Takahashi et al. |
| 8,778,127 B2 | 7/2014 | Schneider et al. |
| 8,853,108 B2 | 10/2014 | Ahoniemi et al. |
| 8,906,275 B2 | 12/2014 | Davis et al. |
| 8,939,957 B2 | 1/2015 | Raycheck et al. |
| 9,005,392 B2 | 4/2015 | Schneider et al. |
| 9,039,855 B2 | 5/2015 | Schneider et al. |
| 9,050,213 B2 | 6/2015 | LaVon et al. |
| 9,156,648 B2 | 10/2015 | Yamamoto |
| 9,168,182 B2 | 10/2015 | Hargett et al. |
| 9,198,804 B2 | 12/2015 | Nakamura et al. |
| 9,226,861 B2 | 1/2016 | Lavon et al. |
| 9,248,054 B2 | 2/2016 | Brown et al. |
| 9,265,672 B2 | 2/2016 | Brown et al. |
| 9,295,590 B2 | 3/2016 | Brown et al. |
| 9,370,775 B2 | 6/2016 | Harvey et al. |
| 9,440,043 B2 | 9/2016 | Schneider et al. |
| 9,453,303 B2 | 9/2016 | Aberg et al. |
| 9,539,735 B2 | 1/2017 | Ferguson et al. |
| 9,732,454 B2 | 8/2017 | Davis et al. |
| 9,758,339 B2 | 9/2017 | Yanez, Jr. et al. |
| 9,795,520 B2 | 10/2017 | Kaneko et al. |
| 9,877,876 B2 | 1/2018 | Huang et al. |
| 1,019,024 A1 | 1/2019 | Ashraf et al. |
| 1,059,604 A1 | 3/2020 | Koshijima et al. |
| 1,079,219 A1 | 10/2020 | Hohm et al. |
| 2001/0030014 A1 | 10/2001 | Kwok |
| 2002/0026660 A1 | 3/2002 | Goda |
| 2002/0046802 A1 | 4/2002 | Tachibana et al. |
| 2002/0072723 A1 | 6/2002 | Ronn et al. |
| 2002/0099347 A1 | 7/2002 | Chen et al. |
| 2002/0103469 A1 | 8/2002 | Chen et al. |
| 2002/0134067 A1 | 9/2002 | Heaney et al. |
| 2002/0153271 A1 | 10/2002 | McManus et al. |
| 2002/0177829 A1 | 11/2002 | Fell et al. |
| 2003/0044585 A1 | 3/2003 | Taylor et al. |
| 2003/0070780 A1 | 4/2003 | Chen et al. |
| 2003/0087056 A1 | 5/2003 | Ducker et al. |
| 2003/0093045 A1 | 5/2003 | Erdman |
| 2003/0119404 A1 | 6/2003 | Belau et al. |
| 2003/0125687 A1 | 7/2003 | Gubernick et al. |
| 2003/0144643 A1 | 7/2003 | Jaärpenberg et al. |
| 2003/0203162 A1 | 10/2003 | Christopher et al. |
| 2003/0233082 A1 | 12/2003 | Kline et al. |
| 2004/0006323 A1 | 1/2004 | Hall et al. |
| 2004/0030317 A1 * | 2/2004 | Torigoshi .......... A61F 13/49014 604/385.27 |
| 2004/0059309 A1 | 3/2004 | Nortman |
| 2004/0097895 A1 | 5/2004 | Busam et al. |
| 2004/0127881 A1 | 7/2004 | Stevens et al. |
| 2004/0133180 A1 | 7/2004 | Mori et al. |
| 2004/0158212 A1 | 8/2004 | Ponomarenko et al. |
| 2004/0158217 A1 | 8/2004 | Wu et al. |
| 2004/0219854 A1 | 11/2004 | Groitzsch et al. |
| 2004/0230171 A1 | 11/2004 | Ando et al. |
| 2005/0013975 A1 | 1/2005 | Brock et al. |
| 2005/0107764 A1 | 5/2005 | Matsuda et al. |
| 2005/0148971 A1 | 7/2005 | Kuroda et al. |
| 2005/0230037 A1 | 10/2005 | Jenquin et al. |
| 2005/0244640 A1 | 11/2005 | Riswick et al. |
| 2005/0267431 A1 | 12/2005 | Sasaki et al. |
| 2006/0047260 A1 | 3/2006 | Ashton et al. |
| 2006/0069373 A1 | 3/2006 | Schlinz et al. |
| 2006/0087053 A1 | 4/2006 | O'Donnell et al. |
| 2006/0105075 A1 | 5/2006 | Otsubo |
| 2006/0189954 A1 | 8/2006 | Kudo et al. |
| 2006/0228969 A1 | 10/2006 | Erdman |
| 2006/0270302 A1 | 11/2006 | Ando et al. |
| 2007/0026753 A1 | 2/2007 | Neely et al. |
| 2007/0045143 A1 | 3/2007 | Clough et al. |
| 2007/0045144 A1 | 3/2007 | Wheeler et al. |
| 2007/0131335 A1 | 6/2007 | Zhou et al. |
| 2007/0141311 A1 | 6/2007 | Mleziva et al. |
| 2007/0179466 A1 | 8/2007 | Tremblay et al. |
| 2007/0196650 A1 | 8/2007 | Yamamoto et al. |
| 2008/0134487 A1 | 6/2008 | Hartono |
| 2008/0149292 A1 | 6/2008 | Scherb |
| 2008/0161768 A1 | 7/2008 | Baba et al. |
| 2008/0287897 A1 | 11/2008 | Guzman et al. |
| 2009/0177176 A1 * | 7/2009 | Saito ................ A61F 13/49017 604/385.29 |
| 2009/0204093 A1 | 8/2009 | Vasic et al. |
| 2009/0312730 A1 | 12/2009 | LaVon et al. |
| 2010/0022151 A1 | 1/2010 | Malowaniec |
| 2010/0036346 A1 | 2/2010 | Hammons et al. |
| 2010/0048072 A1 | 2/2010 | Kauschke |
| 2010/0075103 A1 | 3/2010 | Miyamoto |
| 2010/0076394 A1 | 3/2010 | Hayase et al. |
| 2010/0248575 A1 | 9/2010 | Malz |
| 2010/0307668 A1 | 12/2010 | Lange et al. |
| 2011/0092943 A1 | 4/2011 | Bishop et al. |
| 2011/0118689 A1 | 5/2011 | Een et al. |
| 2011/0120897 A1 | 5/2011 | Takahashi |

(56) References Cited

U.S. PATENT DOCUMENTS

| | | |
|---|---|---|
| 2011/0250378 A1 | 10/2011 | Eaton et al. |
| 2012/0004633 A1 | 1/2012 | Marcelo et al. |
| 2012/0061015 A1 | 3/2012 | LaVon et al. |
| 2012/0061016 A1 | 3/2012 | LaVon et al. |
| 2012/0071852 A1 | 3/2012 | Tsang et al. |
| 2012/0095429 A1 | 4/2012 | Kobayashi et al. |
| 2012/0271267 A1* | 10/2012 | Love .................. A61F 13/49011 604/385.101 |
| 2012/0277713 A1 | 11/2012 | Raycheck et al. |
| 2012/0323206 A1 | 12/2012 | McMorrow et al. |
| 2013/0032656 A1 | 2/2013 | Yamamoto |
| 2013/0072887 A1 | 3/2013 | LaVon et al. |
| 2013/0102982 A1* | 4/2013 | Nakano ............. A61F 13/49019 604/365 |
| 2013/0112584 A1 | 5/2013 | Gaspari et al. |
| 2013/0139960 A1 | 6/2013 | Maruyama et al. |
| 2013/0171421 A1 | 7/2013 | Weisman et al. |
| 2013/0199696 A1 | 8/2013 | Schneider et al. |
| 2013/0199707 A1 | 8/2013 | Schneider |
| 2013/0211356 A1 | 8/2013 | Nishikawa et al. |
| 2013/0211363 A1* | 8/2013 | LaVon ............... A61F 13/49012 604/385.3 |
| 2013/0255861 A1 | 10/2013 | Schneider |
| 2013/0255862 A1 | 10/2013 | Schneider et al. |
| 2013/0255863 A1 | 10/2013 | LaVon et al. |
| 2013/0255864 A1 | 10/2013 | Schneider et al. |
| 2013/0255865 A1 | 10/2013 | Brown et al. |
| 2013/0261589 A1 | 10/2013 | Fujkawa et al. |
| 2013/0306226 A1 | 11/2013 | Zink et al. |
| 2014/0000794 A1 | 1/2014 | Hamilton et al. |
| 2014/0005621 A1 | 1/2014 | Roe et al. |
| 2014/0018759 A1 | 1/2014 | Jayasinghe et al. |
| 2014/0041797 A1 | 2/2014 | Schneider |
| 2014/0107605 A1 | 4/2014 | Schroer, Jr. et al. |
| 2014/0127460 A1 | 5/2014 | Xu et al. |
| 2014/0136893 A1 | 5/2014 | Xie et al. |
| 2014/0148773 A1 | 5/2014 | Brown et al. |
| 2014/0234575 A1 | 8/2014 | Mitsuno et al. |
| 2014/0235127 A1 | 8/2014 | DeJesus et al. |
| 2014/0257231 A1 | 9/2014 | Wang et al. |
| 2014/0276517 A1 | 9/2014 | Chester et al. |
| 2014/0288521 A1 | 9/2014 | Wade et al. |
| 2014/0296815 A1 | 10/2014 | Takken et al. |
| 2014/0302286 A1 | 10/2014 | Okuda et al. |
| 2014/0305570 A1 | 10/2014 | Matsunaga et al. |
| 2014/0324009 A1 | 10/2014 | Lee et al. |
| 2014/0343525 A1 | 11/2014 | Roh et al. |
| 2014/0377506 A1 | 12/2014 | Eckstein et al. |
| 2014/0377513 A1 | 12/2014 | Galie et al. |
| 2015/0083309 A1 | 3/2015 | Long et al. |
| 2015/0126956 A1 | 5/2015 | Raycheck et al. |
| 2015/0136893 A1 | 5/2015 | Koskol |
| 2015/0164708 A1 | 6/2015 | Hashimoto et al. |
| 2015/0167207 A1 | 6/2015 | Bongartz et al. |
| 2015/0173967 A1 | 6/2015 | Kreuzer et al. |
| 2015/0230995 A1 | 8/2015 | Kaneko et al. |
| 2015/0245958 A1 | 9/2015 | Chmielewski et al. |
| 2015/0257941 A1 | 9/2015 | Eckstein et al. |
| 2015/0282999 A1 | 10/2015 | Arizti et al. |
| 2015/0320612 A1 | 11/2015 | Seitz et al. |
| 2015/0320613 A1 | 11/2015 | Seitz et al. |
| 2015/0320619 A1 | 11/2015 | Seitz et al. |
| 2015/0320620 A1 | 11/2015 | Seitz et al. |
| 2015/0320622 A1* | 11/2015 | Seitz ................. A61F 13/55115 604/385.02 |
| 2015/0328056 A1 | 11/2015 | Een et al. |
| 2015/0351972 A1 | 12/2015 | Bing-Wo |
| 2016/0058624 A1 | 3/2016 | Hohm et al. |
| 2016/0058627 A1 | 3/2016 | Barnes et al. |
| 2016/0067119 A1 | 3/2016 | Weisman et al. |
| 2016/0100989 A1 | 4/2016 | Seitz et al. |
| 2016/0100997 A1 | 4/2016 | Seitz et al. |
| 2016/0106633 A1 | 4/2016 | Nagata et al. |
| 2016/0129661 A1 | 5/2016 | Arora et al. |
| 2016/0136009 A1 | 5/2016 | Weisman et al. |
| 2016/0228305 A1 | 8/2016 | Gualtieri et al. |
| 2016/0270977 A1 | 9/2016 | Surushi et al. |
| 2016/0331600 A1 | 11/2016 | Polidori et al. |
| 2017/0014281 A1 | 1/2017 | Xie et al. |
| 2017/0027774 A1 | 2/2017 | Ashraf et al. |
| 2017/0029993 A1 | 2/2017 | Ashraf et al. |
| 2017/0029994 A1 | 2/2017 | Ashraf et al. |
| 2017/0056256 A1 | 3/2017 | Smith et al. |
| 2017/0065461 A1 | 3/2017 | Schneider |
| 2017/0079852 A1 | 3/2017 | Fujima et al. |
| 2017/0119595 A1 | 5/2017 | Carla et al. |
| 2017/0191198 A1 | 7/2017 | Ashraf et al. |
| 2017/0258650 A1 | 9/2017 | Rosati et al. |
| 2017/0281417 A1 | 10/2017 | Ishikawa |
| 2017/0319403 A1 | 11/2017 | Bewick-Sonntag et al. |
| 2017/0348163 A1 | 12/2017 | Lakso et al. |
| 2018/0092784 A1 | 4/2018 | Wade et al. |
| 2018/0140473 A1 | 5/2018 | Koshijima et al. |
| 2018/0168874 A1 | 6/2018 | LaVon et al. |
| 2018/0168875 A1 | 6/2018 | LaVon et al. |
| 2018/0168876 A1 | 6/2018 | LaVon et al. |
| 2018/0168877 A1 | 6/2018 | Schneider et al. |
| 2018/0168878 A1 | 6/2018 | Schneider et al. |
| 2018/0168879 A1 | 6/2018 | Schneider et al. |
| 2018/0168880 A1 | 6/2018 | Schneider et al. |
| 2018/0168885 A1 | 6/2018 | Zink, II et al. |
| 2018/0168887 A1 | 6/2018 | LaVon et al. |
| 2018/0168888 A1 | 6/2018 | Zink, II et al. |
| 2018/0168889 A1 | 6/2018 | LaVon et al. |
| 2018/0168890 A1 | 6/2018 | LaVon et al. |
| 2018/0168891 A1 | 6/2018 | Wise et al. |
| 2018/0168892 A1 | 6/2018 | LaVon et al. |
| 2018/0168893 A1 | 6/2018 | Ashraf et al. |
| 2018/0169964 A1 | 6/2018 | Schneider et al. |
| 2018/0170026 A1 | 6/2018 | Schneider et al. |
| 2018/0170027 A1 | 6/2018 | Schneider et al. |
| 2018/0214318 A1 | 8/2018 | Ashraf et al. |
| 2018/0214321 A1 | 8/2018 | Ashraf et al. |
| 2018/0216269 A1 | 8/2018 | Ashraf et al. |
| 2018/0216270 A1 | 8/2018 | Ashraf et al. |
| 2018/0216271 A1 | 8/2018 | Ashraf et al. |
| 2018/0333311 A1* | 11/2018 | Maki ..................... A61F 13/49 |
| 2019/0003079 A1 | 1/2019 | Ashraf et al. |
| 2019/0003080 A1 | 1/2019 | Ashraf et al. |
| 2019/0070041 A1 | 3/2019 | Schneider et al. |
| 2019/0070042 A1 | 3/2019 | LaVon et al. |
| 2019/0112737 A1 | 4/2019 | Ashraf et al. |
| 2019/0254881 A1 | 8/2019 | Ishikawa et al. |
| 2019/0298586 A1 | 10/2019 | Ashraf et al. |
| 2019/0298587 A1 | 10/2019 | Ashraf et al. |
| 2019/0246196 A1 | 12/2019 | Han et al. |
| 2019/0374392 A1 | 12/2019 | Ninomiya et al. |
| 2019/0374404 A1 | 12/2019 | Ninomiya et al. |
| 2020/0155370 A1 | 5/2020 | Ohtsubo et al. |
| 2020/0155371 A1 | 5/2020 | Ohtsubo et al. |
| 2020/0206040 A1 | 7/2020 | Andrews et al. |
| 2020/0214901 A1 | 7/2020 | Andrews et al. |
| 2020/0298545 A1 | 9/2020 | Andrews et al. |

FOREIGN PATENT DOCUMENTS

| | | |
|---|---|---|
| CN | 1685099 | 10/2005 |
| CN | 101746057 | 6/2010 |
| CN | 105997351 | 10/2016 |
| EP | 0989218 | 3/2000 |
| EP | 1305248 | 5/2003 |
| EP | 1452157 | 9/2004 |
| EP | 1473148 | 11/2004 |
| EP | 1393701 | 7/2013 |
| EP | 3056176 | 8/2016 |
| EP | 3092997 | 8/2017 |
| EP | 3251642 | 12/2017 |
| EP | 3257488 | 12/2017 |
| EP | 3563817 A1 | 11/2019 |
| JP | 3213543 A | 9/1991 |
| JP | H03213543 | 9/1991 |
| JP | H04030847 | 2/1992 |
| JP | H06254117 | 9/1994 |
| JP | 8071107 A | 3/1996 |

(56) References Cited

FOREIGN PATENT DOCUMENTS

| | | |
|---|---|---|
| JP | H08071107 | 3/1996 |
| JP | H08132576 | 5/1996 |
| JP | 2000026015 | 1/2000 |
| JP | 2000160460 | 6/2000 |
| JP | 3086141 B2 | 9/2000 |
| JP | 2002035029 | 2/2002 |
| JP | 2002178428 | 6/2002 |
| JP | 2002248127 | 9/2002 |
| JP | 2003521949 | 7/2003 |
| JP | 2004081365 | 3/2004 |
| JP | 2004229857 | 8/2004 |
| JP | 2004237410 | 8/2004 |
| JP | 2004254862 | 9/2004 |
| JP | 2004298362 | 10/2004 |
| JP | 2005320636 | 11/2005 |
| JP | 2006149747 | 6/2006 |
| JP | 2006149749 | 6/2006 |
| JP | 2006204673 | 12/2006 |
| JP | 2007190397 | 8/2007 |
| JP | 2008029749 | 2/2008 |
| JP | 2008055198 | 3/2008 |
| JP | 2008104853 | 5/2008 |
| JP | 2008105425 | 5/2008 |
| JP | 2008154998 | 5/2008 |
| JP | 2008148942 | 7/2008 |
| JP | 2008179128 | 8/2008 |
| JP | 2008194493 | 8/2008 |
| JP | 2008229006 | 10/2008 |
| JP | 2008229007 | 10/2008 |
| JP | 2008253290 | 10/2008 |
| JP | 2008260131 | 10/2008 |
| JP | 2008264480 | 11/2008 |
| JP | 2008272250 | 11/2008 |
| JP | 2008272253 | 11/2008 |
| JP | 2008296585 | 12/2008 |
| JP | 2009000161 | 1/2009 |
| JP | 2009039341 | 2/2009 |
| JP | 2009056156 | 3/2009 |
| JP | 2009106667 | 5/2009 |
| JP | 2009172231 | 8/2009 |
| JP | 2009240804 | 10/2009 |
| JP | 2009241607 | 10/2009 |
| JP | 2010131833 | 6/2010 |
| JP | 2011015707 | 1/2011 |
| JP | 2011111165 | 6/2011 |
| JP | 2011178124 | 9/2011 |
| JP | 2011225000 | 11/2011 |
| JP | 2012050882 | 3/2012 |
| JP | 2012050883 | 3/2012 |
| JP | 2012115358 | 6/2012 |
| JP | 2012521498 | 9/2012 |
| JP | 5124187 | 11/2012 |
| JP | 5124188 | 11/2012 |
| JP | 2013138795 | 7/2013 |
| JP | 2014097257 | 5/2014 |
| JP | 2014111222 | 6/2014 |
| JP | 2014188042 | 10/2014 |
| JP | 2015510831 | 4/2015 |
| JP | 2015521499 | 7/2015 |
| JP | 2016013687 | 1/2016 |
| JP | 2016016536 | 2/2016 |
| JP | 5942819 | 6/2016 |
| JP | 2016193199 | 11/2016 |
| JP | 6149635 | 6/2017 |
| JP | 2020054741 A | 4/2018 |
| JP | 2020054742 A | 4/2018 |
| JP | 2020054744 A | 4/2018 |
| JP | 2020054745 A | 4/2018 |
| JP | 2019081304 | 5/2019 |
| JP | 2019166804 | 10/2019 |
| JP | 2019181807 | 10/2019 |
| WO | WO 9925296 | 5/1999 |
| WO | WO 20030059603 | 7/2003 |
| WO | WO2008123348 | 10/2008 |
| WO | WO2003015681 | 2/2013 |
| WO | WO2013084977 | 6/2013 |
| WO | WO20140841 68 | 6/2014 |
| WO | WO2014196669 | 11/2014 |
| WO | WO 2016047320 | 3/2016 |
| WO | WO20160056092 | 4/2016 |
| WO | WO20160056093 | 4/2016 |
| WO | WO20160063346 | 4/2016 |
| WO | WO20160067387 | 5/2016 |
| WO | WO20160071981 | 5/2016 |
| WO | WO20160075974 | 5/2016 |
| WO | WO20160098416 | 6/2016 |
| WO | WO20160104412 | 6/2016 |
| WO | WO20160104422 | 6/2016 |
| WO | WO20160158499 | 10/2016 |
| WO | WO20160158746 | 10/2016 |
| WO | WO20160208502 | 12/2016 |
| WO | WO20160208513 | 12/2016 |
| WO | WO2017105997 | 6/2017 |
| WO | WO 2018061288 | 4/2018 |
| WO | WO 2018084145 | 5/2018 |
| WO | WO 2018154680 A1 | 8/2018 |
| WO | WO 2018154682 A1 | 8/2018 |
| WO | WO 2018167836 A1 | 8/2018 |
| WO | WO 2019046363 | 3/2019 |
| WO | WO 2019111203 | 6/2019 |
| WO | WO 2019150802 A1 | 8/2019 |
| WO | WO 2020006996 | 1/2020 |

OTHER PUBLICATIONS

3D Nonwovens Developments for textured nonwovens; Detlef Frey; http://web.archive.org/web/20170919080326/https://www.reicofil.com/en/pages/3d_no nwovens, Sep. 19, 2017.
PCT International Search Report, PCT/US2017/067254, dated Apr. 9, 2018.
All Office Actions, U.S. Appl. No. 15/846,745.
All Office Actions, U.S. Appl. No. 15/846,341.
All Office Actions, U.S. Appl. No. 15/846,360.
All Office Actions, U.S. Appl. No. 15/846,371.
All Office Actions, U.S. Appl. No. 15/846,391.
All Office Actions, U.S. Appl. No. 15/846,409.
All Office Actions, U.S. Appl. No. 16/117,579.
American Cancer Society—What Cancer Patients Their Families and Caregivers Need to Know About Covid 19—Is Impacting Our Patient Services.
ASTM—Standard Tables of Body Measurements for Adult Females Misses Figure Type Size Range 00-20.

* cited by examiner

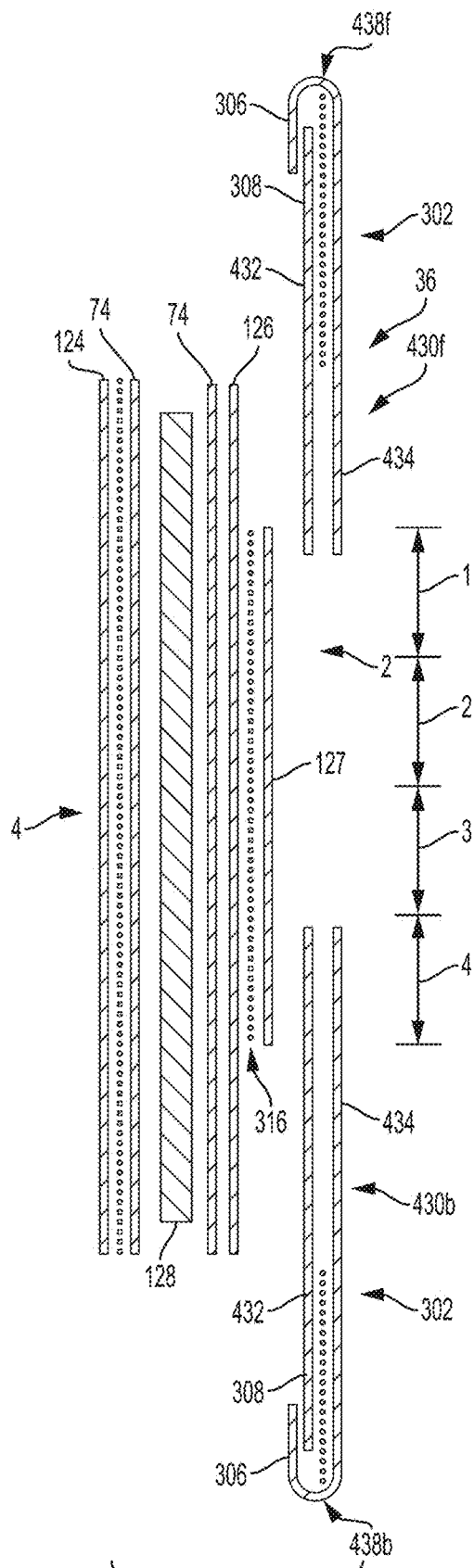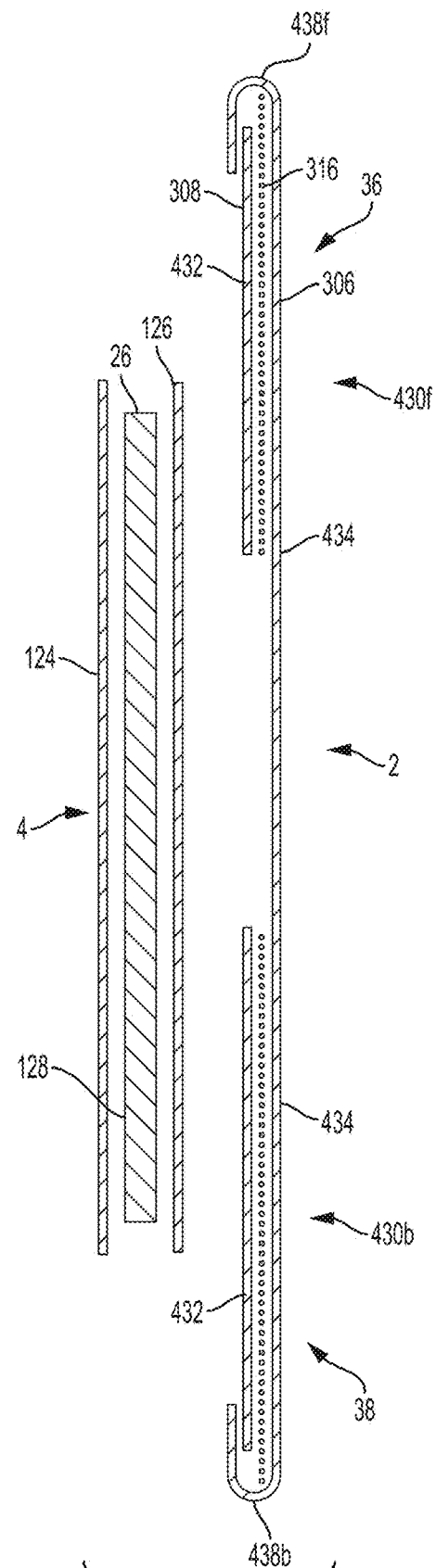
FIG. 7D
FIG. 7E

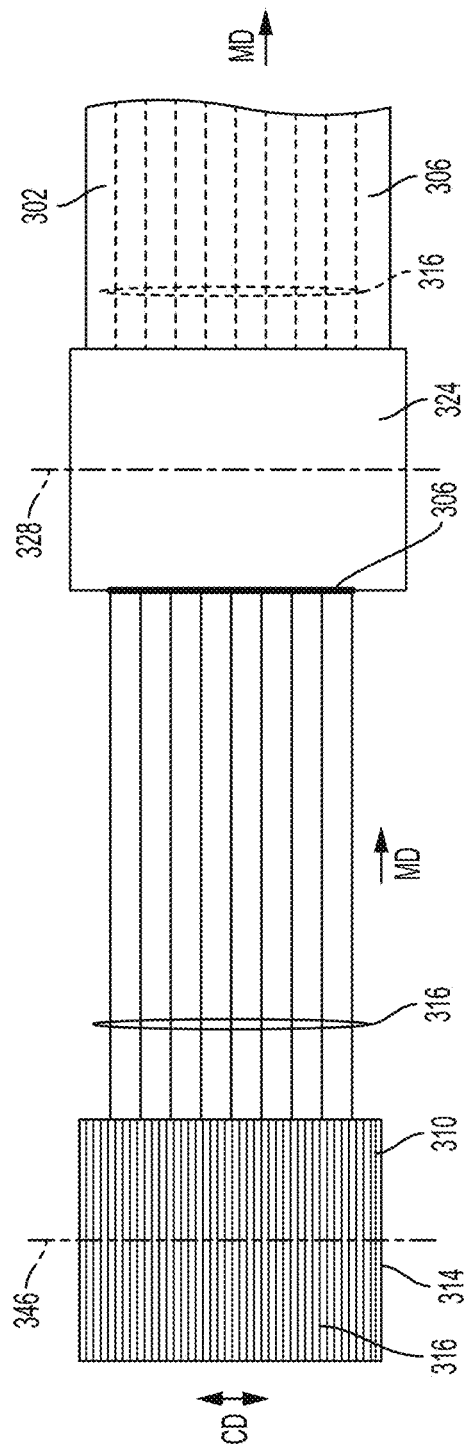

HIP-TO-WAIST AND WAIST-TO-CROTCH SILHOUETTE(S) OF ABSORBENT ARTICLE(S) COMPRISING BEAMED ELASTICS

CROSS-REFERENCE TO RELATED APPLICATIONS

This application claims the benefit, under 35 USC 119(e), to U.S. Provisional Patent Application No. 62/436,589, filed on Dec. 20, 2016 (P&G 14618P); U.S. Provisional Patent Application No. 62/483,965, filed on Apr. 11, 2017 (P&G 14778P); U.S. Provisional Patent Application No. 62/553,149, filed on Sep. 1, 2017 (P&G 14917P); U.S. Provisional Patent Application No. 62/553,171, filed on Sep. 1, 2017 (P&G 14918P); U.S. Provisional Patent Application No. 62/553,538, filed on Sep. 1, 2017 (P&G 14921P); and U.S. Provisional Patent Application No. 62/581,278, filed on Nov. 3, 2017 (P&G 15007P); each of which are herein incorporated by reference in their entirety.

FIELD OF THE INVENTION

The present disclosure relates to absorbent articles, more particularly, to disposable absorbent articles comprising improved elastomeric laminates configured to perform in various components of the disposable absorbent articles.

BACKGROUND OF THE INVENTION

The present disclosure details elastomeric laminates which allow elastomeric absorbent article components (e.g., belts, side panels, etc.) to incorporated into absorbent articles to create more rectangular shapes. The inventive elastomeric laminates as disclosed herein enable products which deliver consumer preferred stretch properties (modulus, pressure on body, air permeability, etc.), while maintaining a wide flexibility in product dimensions (via pre-strain). They accomplish this via the wide latitude of moduli not available with today's marketed stranded products. Today's marketed stranded products are limited in their modulus range. This is due to their strand spacing's and strand decitex, which result in a relatively low modulus and therefore require more stretch to deliver the necessary pressure for sustaining fit. Therefore, they typically require more pre-strain, hence result in a more contracted relaxed product. A key benefit of present disclosure is that the improved elastomeric laminates deliver sufficient wearing pressure, necessary for good fit, without the amount of pre-strain required in today's currently marketed stranded closed-form pant articles. This results in articles that have greater dimensional flexibility without compromising wearing comfort and good fit.

A key benefit of having the Relaxed Product Waist Width, the Relaxed Product Hip Width, and the Relaxed Product Crotch Width (each defined below) relatively equal to each other is that they combine to create a more rectangular, more uniform, and, hence, a more stable package. Absorbent articles are generally distributed to consumers in packages of multiple stacked articles, as illustrated in FIG. 17. The more dimensionally rectangular the articles, in particular at lateral and longitudinal distal edges, the greater the uniformity and stability of the package. The stability of the package is further enhanced if the lateral distal edges are roughly parallel to each other and longitudinal distal edges are roughly parallel to each other. This creates a generally rectangular shape, enabling improved package stability, which allows greater ease of shipping and storing (e.g., in trucks and on store shelves). For Adult incontinence diapers, due to their larger overall dimensions, the Product Waist-to-Crotch Silhouette can be from about 0.8 up to about 2.8. This still facilitates rectangular, stable packages without the necessity for a Relaxed Product Crotch Width that is too large relative to the size of the wearer.

The present disclosure also details elastomeric laminates that enable the design concepts detailed above. The inventive elastomeric laminates disclosed herein comprise a greater number of elastic strands having a greater fineness and a closer spacing than has been previously disclosed or practiced in disposable absorbent articles. These improved elastomeric laminates can be used as disposable absorbent article (e.g., taped diapers, pants, pads, and liners) components for fit and gasketing at the waist, legs, crotch, and sides of the wearer to generally provide the greatest level of extensibility, the most comfortable wearing conditions, improved leakage protection, and a better fit.

More particularly, these improved elastomeric laminates offer several advantages that enable the best executions of the design concepts detailed above, including less pressure of the elastics on the wearer's skin at a given modulus versus traditional elastomeric laminates known today. These improvements result in enhancing application, fit, comfort, and reduced marking of the wearer's skin. The inventive elastomeric laminates disclosed in this application perform better than traditional stranded and film versions of laminates used in disposable absorbent articles today.

SUMMARY OF THE INVENTION

In one disclosed example, an absorbent article may comprise a front waist region, a back waist region, and a crotch region therebetween, a chassis, a back belt, and a front belt. The chassis may comprise a topsheet, a backsheet and an absorbent core disposed between the topsheet and the backsheet, and the chassis may comprise a front end edge, a back end edge, and a pair of laterally opposing side edges. The back belt may be disposed in the back waist region and overlap and extend outboard of the back end edge of the chassis. A front belt may be disposed in the front waist region and overlap and extend outboard of the front end edge of the chassis. The front belt may be joined to the back belt at or adjacent the laterally opposing belt side edges to form leg openings and a waist opening to form a closed-form pant. A longitudinal axis may extend from the midpoint of the front waist edge to the midpoint of the back waist edge and a lateral axis may extend perpendicular to the longitudinal axis through the midpoint of the longitudinal axis. The back belt may comprise a first plurality of elastics comprising greater than about 40 elastic strands, and the front belt may comprise a second plurality of elastics comprising greater than about 40 elastic strands. The first plurality of elastics may have an Average-Strand-Spacing of less than 4 mm, and the second plurality of elastics may have an Average-Strand-Spacing of less than 4 mm. The absorbent article may have a Product Hip-to-Waist Silhouette from about 0.8 to about 1.1, a Product Waist-to-Crotch Silhouette may be from about 0.8 to about 2.0, a Relaxed Product Waist Width from about 80 mm to about 270 mm, and a Relaxed Product Hip Width from about 80 mm to about 300 mm.

The Relaxed Product Waist Width may be from about 170 mm to about 270 mm, and the Relaxed Product Hip Width may be from about 170 to about 300 mm.

The Relaxed Product Waist Width may be from about 80 mm to about 180 mm, and the Relaxed Product Hip Width may be from about 80 mm to about 200 mm.

The back belt may comprise a first plurality of elastics comprising greater than about 70 elastic strands, and the front belt may comprise a second plurality of elastics comprising greater than about 50 elastic strands.

The first plurality of elastics may have an Average-Strand-Spacing of less than 3 mm, and the second plurality of elastics may have an Average-Strand-Spacing of less than 3 mm.

An Average-Dtex of the first plurality of elastics may be from about 10 to about 500, and the Average-Dtex of the second plurality of elastics may be from about 10 to about 500.

A Pressure-Under-Strand of the first plurality of elastics may be from about 0.1 to about 1 psi, and the Pressure-Under-Strand of the second plurality of elastics is from about 0.1 to about 1 psi.

The back belt may be divided into 4 equal sections, wherein Section 4 may comprise a proximal end edge of the back belt, Section 1 may comprise a distal end edge of the back belt, Section 2 may be proximate to Section 1 and Section 3 may be proximate to Section 4, where at least two of the sections may each have greater than 10 elastic strands; and where the front belt may be divided into 4 equal sections, wherein Section 4 may comprise a proximal end edge of the back belt, Section 1 may comprise a distal end edge of the back belt, Section 2 may be proximate to Section 1 and Section 3 may be proximate to Section 4, where at least two of the sections may each have greater than 10 elastic strands.

Section 1 of the back belt may be longitudinally longer than Section 1 of the front belt.

The first plurality of elastics of the back belt may be between an inner and an outer nonwoven, and where the second plurality of elastics of the front belt may be between an inner and an outer nonwoven, and where the inner nonwovens of the front and back belts may be separate and distinct and longitudinally spaced from each other, and where the outer nonwovens of the front and back belts may be separate and distinct and longitudinally spaced from each other.

In another disclosed example, an absorbent article may comprise a front waist region, a back waist region, and a crotch region therebetween, a chassis, a back belt, and a front belt. The chassis may comprise a topsheet, a backsheet and an absorbent core disposed between the topsheet and the backsheet, and the chassis may comprise a front end edge, a back end edge, and a pair of laterally opposing side edges. The back belt may be disposed in the back waist region overlapping and extending outboard of the back end edge of the chassis. The front belt disposed in the front waist region overlapping and extending outboard of the front end edge of the chassis.

The front belt may be joined to the back belt at or adjacent the laterally opposing belt side edges to form leg openings and a waist opening to form a closed-form pant. A longitudinal axis may extend from the midpoint of the front waist edge to the midpoint of the back waist edge, and a lateral axis extending perpendicular to the longitudinal axis through the midpoint of the longitudinal axis. The back belt may comprise a first plurality of elastics comprising greater than about 60 elastic strands, and the front belt may comprise a second plurality of elastics comprising greater than about 60 elastic strands. The first plurality of elastics may have an Average-Strand-Spacing of less than 4 mm, and the second plurality of elastics may have an Average-Strand-Spacing of less than 4 mm. The absorbent article may have a Product Length-to-Waist Silhouette is from about 0.8 to about 1.08, a Product-Waist-to-Crotch Silhouette is from about 0.8 to about 2.8, a Relaxed Product Waist Width from about 200 mm to about 400 mm, and a Relaxed Product Hip Width from about 200 mm to about 450 mm.

The Relaxed Product Waist Width may be from about 300 mm to about 400 mm and a Relaxed Product Hip Width from about 300 mm to about 450 mm.

The Relaxed Product Waist Width may be from about 200 mm to about 300 mm and a Relaxed Product Hip Width from about 200 mm to about 350 mm.

The back belt may comprise a first plurality of elastics comprising greater than about 80 elastic strands, and the front belt may comprise a second plurality of elastics comprising greater than about 80 elastic strands.

The first plurality of elastics may have an Average-Strand-Spacing of less than 2.5 mm, and the second plurality of elastics may have an Average-Strand-Spacing of less than 2.5 mm.

The Average-Dtex of the first plurality of elastics may be from about 10 to about 500, and the Average-Dtex of the second plurality of elastics may be from about 10 to about 500.

The Pressure-Under-Strand of the first plurality of elastics may be from about 0.1 to about 1 psi, and the Pressure-Under-Strand of the second plurality of elastics may be from about 0.1 to about 1 psi.

The back belt may be divided into 4 equal sections, where Section 4 may comprise a proximal end edge of the back belt, Section 1 may comprise a distal end edge of the back belt, Section 2 may be proximate to Section 1 and Section 3 may be proximate to Section 4, where at least two of the sections may each have greater than 20 elastic strands; and where the front belt may be divided into 4 equal sections, wherein Section 4 may comprise a proximal end edge of the back belt, Section 1 may comprise a distal end edge of the back belt, Section 2 may be proximate to Section 1 and Section 3 may be proximate to Section 4, where at least two of the sections may each have greater than 20 elastic strands.

The first plurality of elastics of the back belt may be between an inner and an outer nonwoven, and where the second plurality of elastics of the front belt may be between an inner and an outer nonwoven, and where the inner nonwovens of the front and back belts are separate and distinct and longitudinally spaced from each other, and where the outer nonwovens of the front and back belts may have a common nonwoven layer that extends continuously from a distal end edge of the front belt to a distal end edge of the back belt.

The first plurality of elastics of the back belt may be between an inner and an outer nonwoven, and where the second plurality of elastics of the front belt may be between an inner and an outer nonwoven, and where the inner nonwovens of the front and back belts may be a common nonwoven layer that extends continuously from a distal end edge of the front belt to a distal end edge of the back belt, and where the outer nonwovens of the front and back belts may be a common nonwoven layer that extends continuously from a distal end edge of the front belt to a distal end edge of the back belt.

BRIEF DESCRIPTION OF THE DRAWINGS

FIG. 7D is a cross section view of an alternate embodiment of the pant of FIG. 7 taken along the longitudinal axis 42, showing longitudinally opposing discrete belts, wherein a plurality of elastics 316 are oriented parallel with the lateral axis 44 between the core wrap 74 and the topsheet 124 and oriented parallel with the lateral axis 44 between the backsheet film 126 and the backsheet nonwoven 127.

FIG. 7E is a cross section view of an alternate embodiment of the belt pant of FIG. 7 taken along the longitudinal axis 42, showing longitudinally opposing discrete inner belt layers 432 and a common outer belt layer 434, and showing a plurality of elastics 316 extending continuously across the core.

FIG. 14A is a view of the converting apparatus of FIG. 14 taken along line 14A-14A.

DETAILED DESCRIPTION

Figure 1:
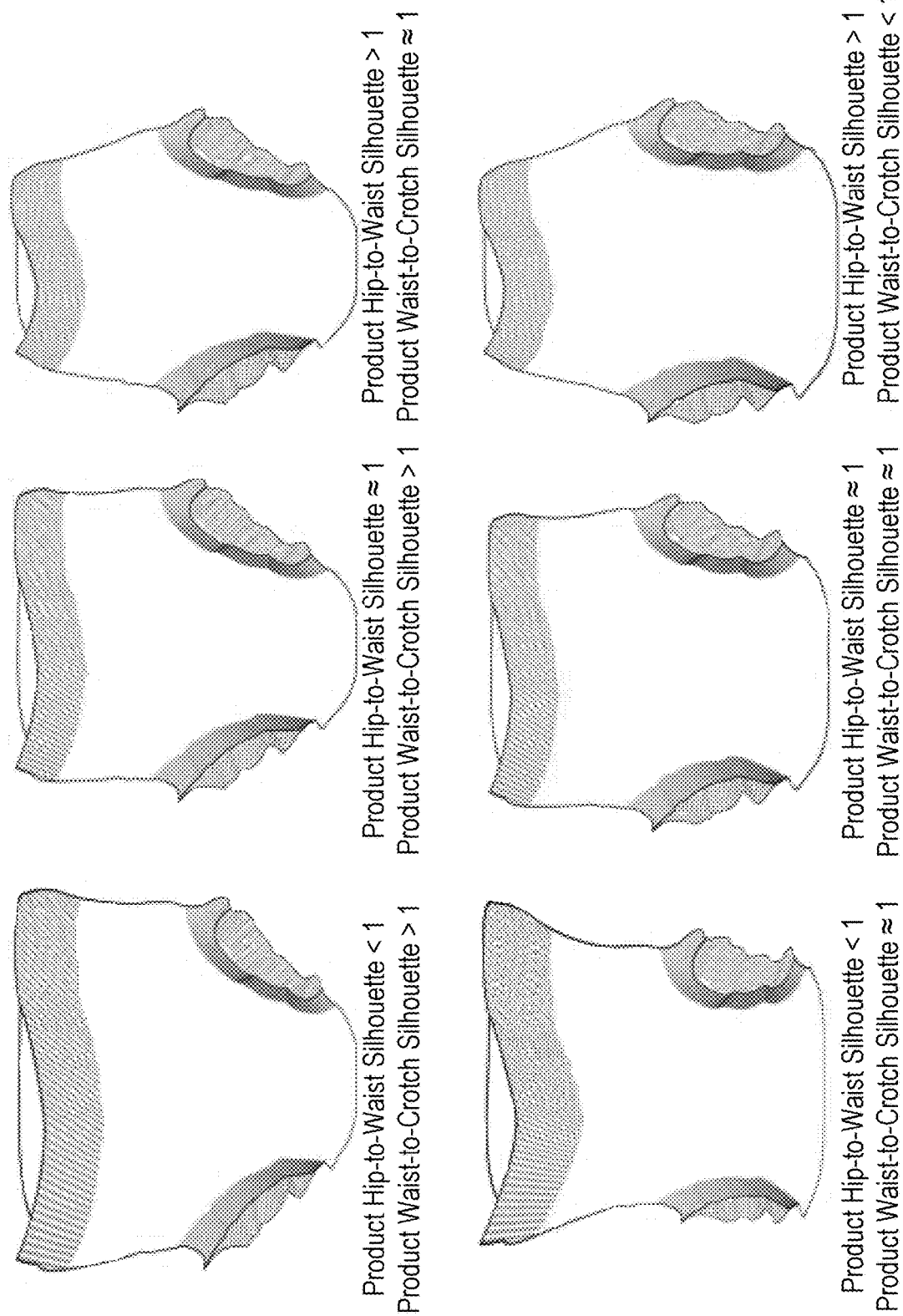
FIG. 1 shows illustrates the Product Hip-to-Waist Silhouette and Product Waist-to-Crotch Silhouette.

The present disclosure details improved elastomeric laminates (also referred to as "beamed elastomeric laminates" comprising "beamed elastics") comprising a greater number of elastic strands having a greater fineness (i.e., lower decitex) and a closer spacing than has been previously disclosed or practiced in disposable absorbent articles. These improved elastomeric laminates can be used as disposable absorbent article (for, example, taped diapers, pants, pads, and liners) components for fit and gasketing at the waist, legs, crotch and sides of the wearer to generally provide the greatest level of extensibility, the most comfortable wearing conditions, improved leakage protection and a better fit.

The following term explanations may be useful in understanding the present disclosure:

"Disposable," in reference to absorbent articles, means that the absorbent articles, are generally not intended to be laundered or otherwise restored or reused as absorbent articles (i.e., they are intended to be discarded after a single use and, preferably, to be recycled, composted or otherwise discarded in an environmentally compatible manner). Disposable absorbent articles often comprise adhesive between the layers and/or a plurality of elastics to hold the article together (e.g., ear panels, side panels, and belts are joined to the chassis via adhesive and the layers of the ear panels, side panels, belts, and chassis are joined together using adhesive). Alternatively, heat and/or pressure bonding are used with the adhesive or in place of the adhesive. In such instances portions of the material layers may become partially melted and pressed together such that once cooled they are physically bonded together. Nonwovens (including, for example, polypropylene, polyethylene, etc.) adhesives (including, for example, styrenic block copolymers (e.g., SIS, SBS)), and absorbent gelling material (AGM 51—see FIGS. 7 and 7B) make up more than 50%, more than 75%, and often more than 90% of the disposable absorbent article weight. And, a core comprising the AGM 51 is often held within the chassis in a manner that would encapsulate and contain the AGM 51 under normal conditions. Such disposable absorbent articles typically have an absorbent capacity of greater than about 100 mL of fluid and can have capacities of up to about 500 mL of fluid or more. Stitching (including the use of thread) and/or woven materials are typically not used to make a disposable absorbent article. If stitching or woven materials are used, they make up an extremely small percentage of the disposable absorbent article. Some landing zones of disposable absorbent articles for fasteners can comprise a woven material, but no other part of a disposable absorbent article typically comprises woven materials.

"Absorbent article" refers to devices, which absorb and contain body exudates and, more specifically, refers to devices, which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, feminine pads, absorbent inserts, and the like.

"Proximal" and "Distal" refer respectively to the location of an element relatively near to or far from the longitudinal or lateral centerline of a structure (e.g., the proximal edge of a longitudinally extending element is located nearer to the longitudinal axis than the distal edge of the same element is located relative to the same longitudinal axis).

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Longitudinal" refers to a direction running substantially perpendicular from a waist edge to an opposing waist edge of the article and generally parallel to the maximum linear dimension of the article. Directions within 45 degrees of the longitudinal direction are considered to be "longitudinal."

"Lateral" refers to a direction running from a longitudinally extending side edge to an opposing longitudinally extending side edge of the article and generally at a right angle to the longitudinal direction. Directions within 45 degrees of the lateral direction are considered to be "lateral."

"Disposed" refers to an element being located in a particular place or position.

"Joined" encompasses configurations whereby an element is directly secured to another element by affixing the element directly to the other element, and configurations whereby an element is indirectly secured to another element by affixing the element to intermediate member(s), which, in turn are affixed to the other element.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable."

"Elastic," "elastomer," or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force. Elastomeric materials may include elastomeric films, scrims, nonwovens, ribbons, strands and other sheet-like structures.

"Pre-strain" refers to the strain imposed on an elastic or elastomeric material prior to combining it with another element of the elastomeric laminate or the absorbent article. Pre-strain is determined by the following equation Pre-strain=((extended length of the elastic-relaxed length of the elastic)/relaxed length of the elastic)*100.

"Decitex" also known as "Dtex" is a measurement used in the textile industry used for measuring yarns or filaments. 1 Decitex=1 gram per 10,000 meters. In other words, if 10,000 linear meters of a yarn or filament weights 500 grams that yarn or filament would have a decitex of 500.

"Substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers of fibrous materials, nonwovens, films and foils such as polymeric films or metallic foils. These materials may be used alone or may comprise two or more layers laminated together. As such, a web is a substrate.

"Nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

"Machine direction" (MD) is used herein to refer to the direction of material flow through a process. In addition, relative placement and movement of material can be described as flowing in the machine direction through a process from upstream in the process to downstream in the process.

"Cross direction" (CD) is used herein to refer to a direction that is generally perpendicular to the machine direction.

"Taped diaper" (also referred to as "open diaper") refers to disposable absorbent articles having an initial front waist region and an initial back waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Example taped diapers are disclosed in various suitable configurations U.S. Pat. Nos. 5,167,897, 5,360,420, 5,599,335, 5,643,588, 5,674,216, 5,702,551, 5,968,025, 6,107,537, 6,118,041, 6,153,209, 6,410,129, 6,426,444, 6,586,652, 6,627,787, 6,617,016, 6,825,393, and 6,861,571; and U.S. Patent Publication Nos. 2013/0072887 A1; 2013/0211356 A1; and 2013/0306226 A1.

"Pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be pre-formed or pre-fastened by various techniques including, but not limited to, joining together portions of the article using any refastenable and/or permanent closure member (e.g., seams, heat bonds, pressure welds, adhesives, cohesive bonds, mechanical fasteners, etc.). A pant can be pre-formed anywhere along the circumference of the article in the waist region (e.g., side fastened or seamed, front waist fastened or seamed, rear waist fastened or seamed). Example diaper pants in various configurations are disclosed in U.S. Pat. Nos. 4,940,464; 5,092,861; 5,246,433; 5,569,234; 5,897, 545; 5,957,908; 6,120,487; 6,120,489; 7,569,039 and U.S. Patent Publication Nos. 2003/0233082 A1; 2005/0107764 A1, 2012/0061016 A1, 2012/0061015 A1; 2013/0255861 A1; 2013/0255862 A1; 2013/0255863 A1; 2013/0255864 A1; and 2013/0255865 A1, all of which are incorporated by reference herein.

"Closed-form" means opposing waist regions are joined, as packaged, either permanently or refastenably to form a continuous waist opening and leg openings.

"Open-form" means opposing waist regions are not initially joined to form a continuous waist opening and leg openings but comprise a closure means such as a fastening system to join the waist regions to form the waist and leg openings before or during application to a wearer of the article.

"Channel," as used herein, is a region or zone in an absorbent material layer that has a substantially lower basis weight (e.g., less than 50%, less than 70%, less than 90%) than the surrounding material in the material layer. The channel may be a region in a material layer that is substantially absorbent material-free (e.g., 90% absorbent material-free, 95% absorbent material-free, or 99% absorbent material-free, or completely absorbent material-free). A channel may extend through one or more absorbent material layers. The channel generally has a lower bending modulus than the surrounding regions of the absorbent material layer, enabling the material layer to bend more easily and/or rapidly distribute more bodily exudates within the channel than in the surrounding areas of the absorbent material layer. Thus, a channel is not merely an indentation in the material layer that does not create a reduced basis weight in the material layer in the area of the channel.

Figure 2:
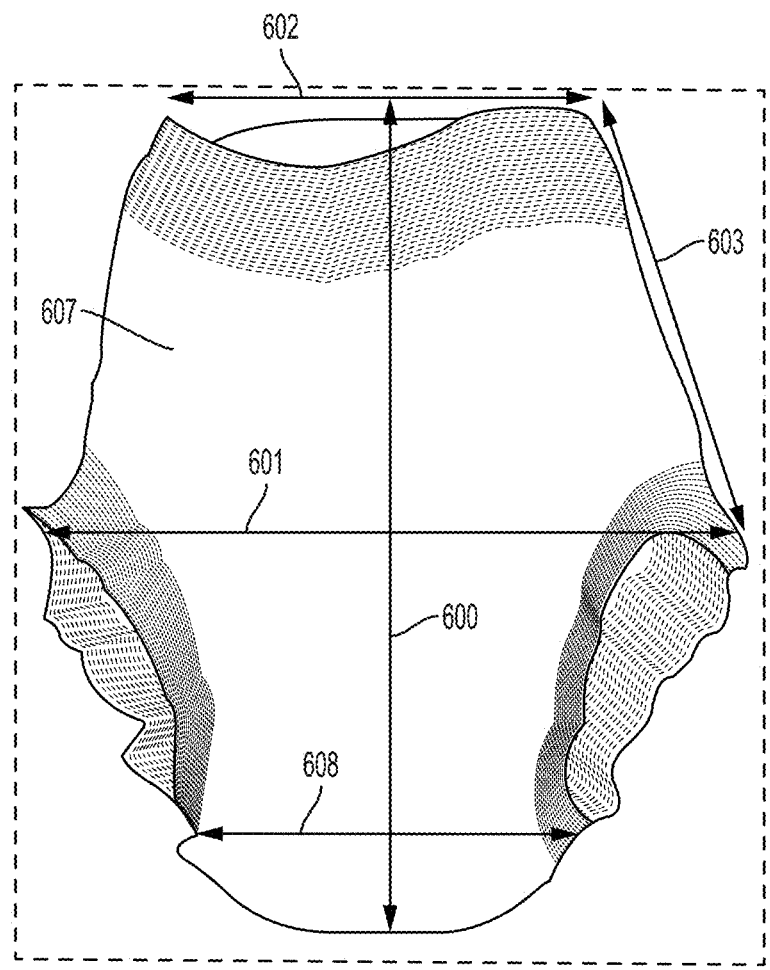
FIG. 2 shows a closed-form pant product in its laid out, relaxed, and unfolded state.

"Relaxed Product Waist Width" means the lateral distance from the distal most point at the right side of the front waist edge to the distal most point at the left side of the front waist edge. The lateral distance is measured perpendicular to the longitudinal axis of the product. Refer to FIG. 2.

"Relaxed Product Hip Width" means the lateral distance from the laterally distal most point of the left side edge of the product at the upper edge of the left leg opening to the laterally distal most point of the right side edge of the product at the upper edge of the right leg opening. Refer to FIG. 2. The lateral distance is measured perpendicular to the longitudinal axis of the product.

"Relaxed Product Crotch Width" means the lateral distance from the distal most point at the right side of the bottom edge to the distal most point at the left side of the bottom edge. The lateral distance is measured perpendicular to the longitudinal axis of the product. Refer to FIG. 2.

"Product Hip-to-Waist Silhouette" means Relaxed Product Hip Width (601) (mm) divided by the Relaxed Product Waist Width (602) (mm). See FIG. 2.

"Product Waist-to-Crotch Silhouette" means Relaxed Product Waist Width (602) (mm) divided by the Relaxed Product Crotch Width (608) (mm). See FIG. 2.

Absorbent Articles of the Present Disclosure

Products comprising elastomeric laminates of the present disclosure may comprise absorbent articles 100 of differing structure and/or form that are generally designed and configured to manage bodily exudates such as urine, menses, and/or feces, such as disposable taped and pants, including baby and adult disposable absorbent articles.

As shown in the figures, the absorbent articles 100 of the present disclosure may comprise a chassis 200 comprising a topsheet 124, a backsheet 125, and an absorbent core 128 disposed at least partially between the topsheet 124 and the backsheet 125. The chassis 200 may further comprise an inner leg cuff 150 and an outer leg cuff 140 (the cuffs generally referred to as 52).

One end portion of an absorbent article 100 may be configured as a front waist region 36 and the longitudinally opposing end portion may be configured as a back waist region 38. An intermediate portion of the absorbent article 100 extending longitudinally between the front waist region 36 and the back waist region 38 may be configured as a crotch region 37. The length of each of the front waist region 36, the back waist region 38 and the crotch region 37 may be about ⅓ of the length of the absorbent article 100, for example (see, for example, FIGS. 9 and 10). Alternatively, the length of each of the front waist region 36, the back waist region 38, and the crotch region 37 may have other dimensions (e.g., defined by the belt or ear panel or side panel dimensions—see, for example, FIGS. 3B, 4, and 7). The absorbent article 100 may have a laterally extending front waist end edge 136 in the front waist region 36 and a longitudinally opposing and laterally extending back waist end edge 138 in the back waist region 38.

Figure 7:
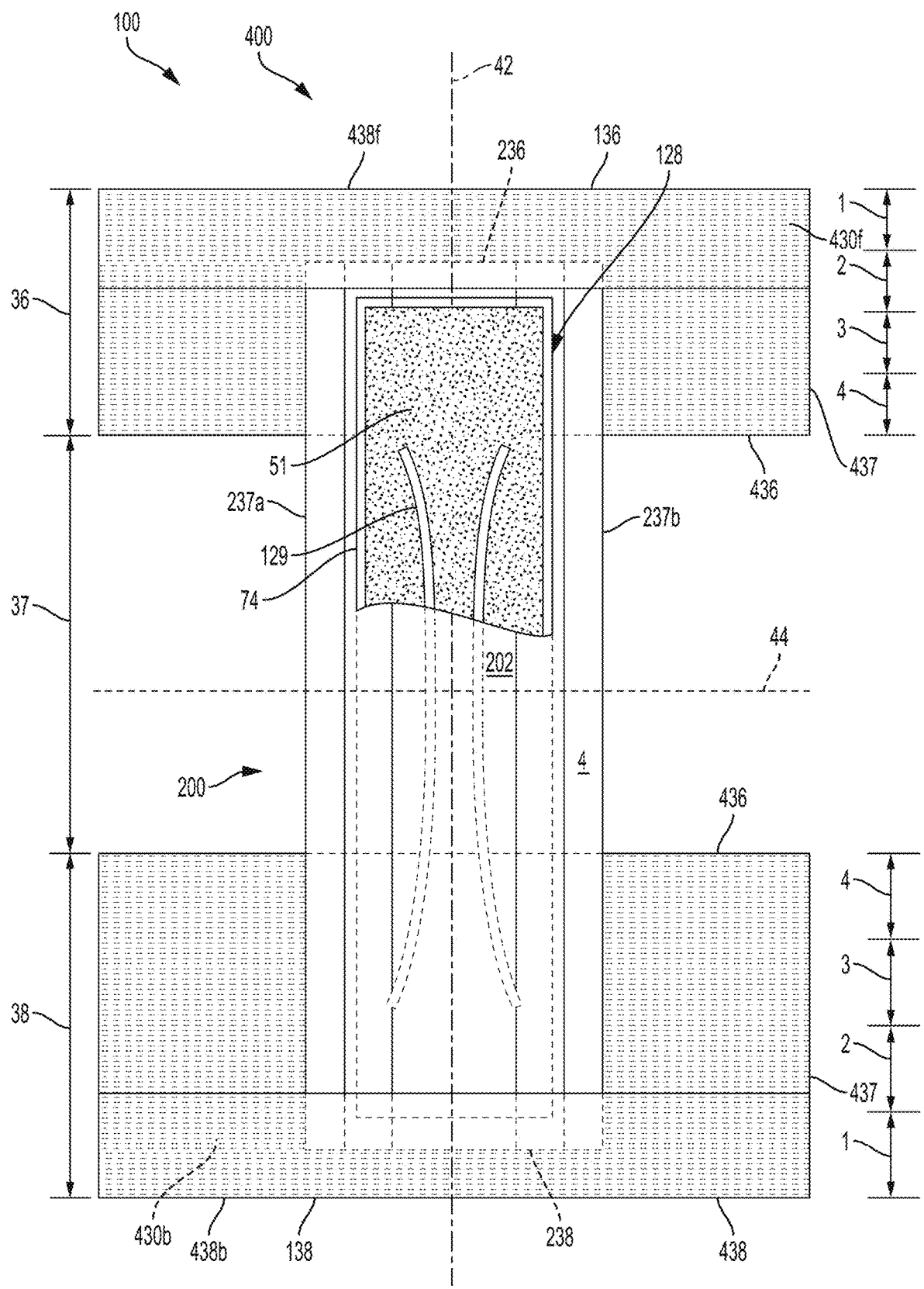
FIG. 7 is a plan view of the pant of FIG. 6, prior to joining side edges of the belt to form the waist and leg openings.

The chassis 200 of the absorbent article 100 may comprise a first longitudinally extending side edge 237*a* and a laterally opposing and second longitudinally extending side edge 237*b*. Both of the side edges 237 may extend longitudinally between the front waist end edge 136 and the back waist end edge 138. The chassis 200 may form a portion of the laterally extending front waist end edge 136 in the front waist region 36 and a portion of the longitudinally opposing and laterally extending back waist end edge 138 in the back waist region 38. Furthermore, the chassis 200 may comprise a chassis interior surface 202 (forming at least a portion of the wearer-facing surface 4), a chassis exterior surface 204 (forming at least a portion of the garment-facing surface 2), a longitudinal axis 42, and a lateral axis 44. The longitudinal axis 42 may extend through a midpoint of the front waist end edge 136 and through a midpoint of the back waist end edge 138, while the lateral axis 44 may extend through a midpoint of the first side edge 237a and through a midpoint of the second side edge 237b. Referring to FIG. 7, often true for belted absorbent articles, the chassis 200 may have a length measured along the longitudinal axis 42 that is less than the length of the absorbent article 100. Both of the side edges 237 of the chassis 200 may not extend longitudinally to one or both of the front waist end edge 136 and the back waist end edge 138. The chassis 200 may not form a portion of one or both of the laterally extending front waist end edge 136 in the front waist region 36 and the longitudinally opposing and laterally extending back waist end edge 138 in the back waist region 38.

Figure 7A:
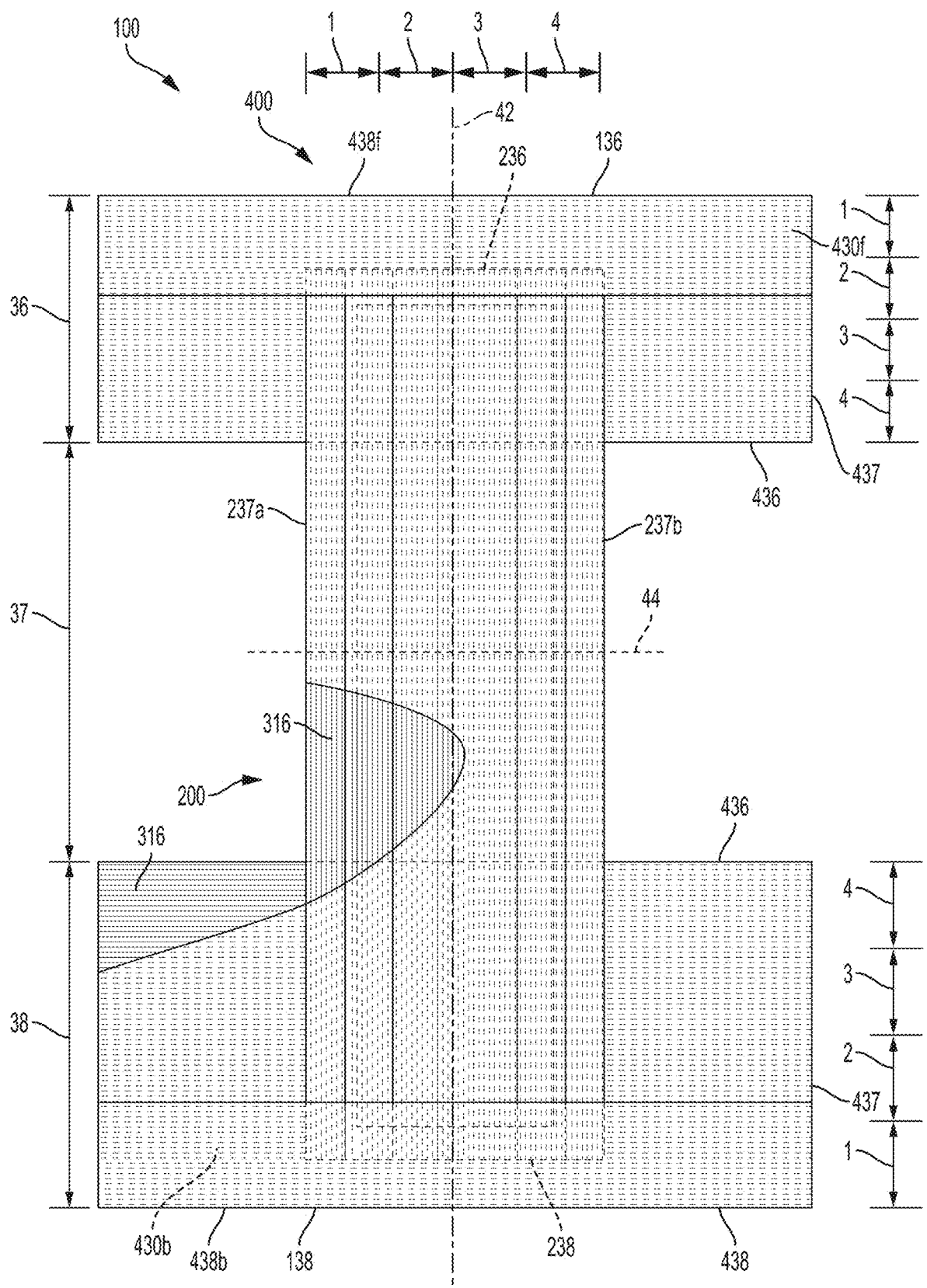
FIG. 7A is a plan view of an alternate embodiment of the belt pant of FIG. 7 illustrating an elasticized topsheet and an elasticized backsheet.
Figure 7B:
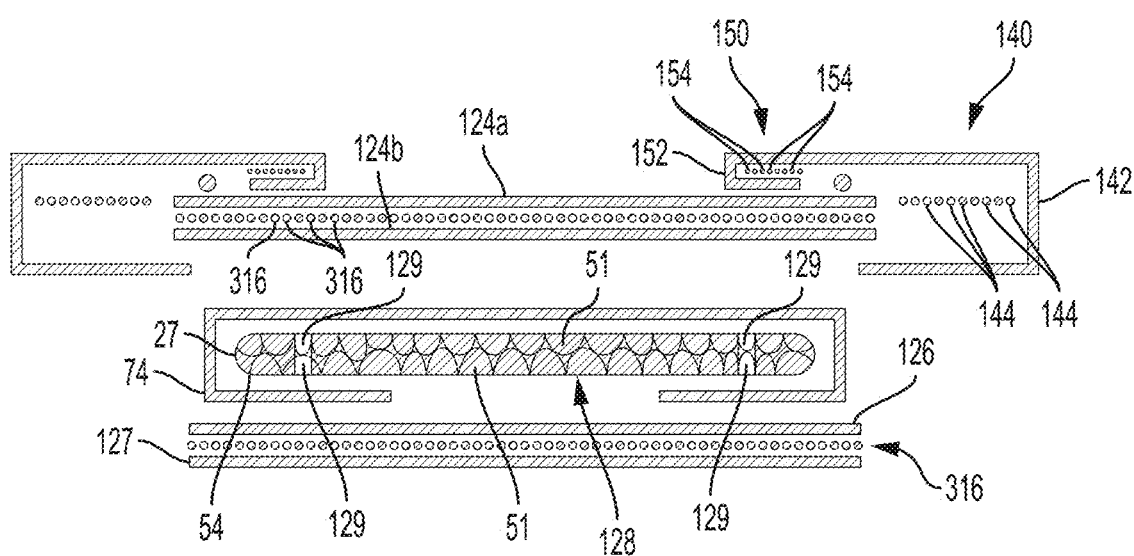
FIG. 7B is a cross section view of the pant of FIG. 7A taken along the transverse axis, illustrating the elasticized topsheet (showing a plurality of elastics 316 oriented parallel with the longitudinal axis 42) and the elasticized backsheet (showing a plurality of elastics 316 oriented parallel with the longitudinal axis 42).
Figure 7C:
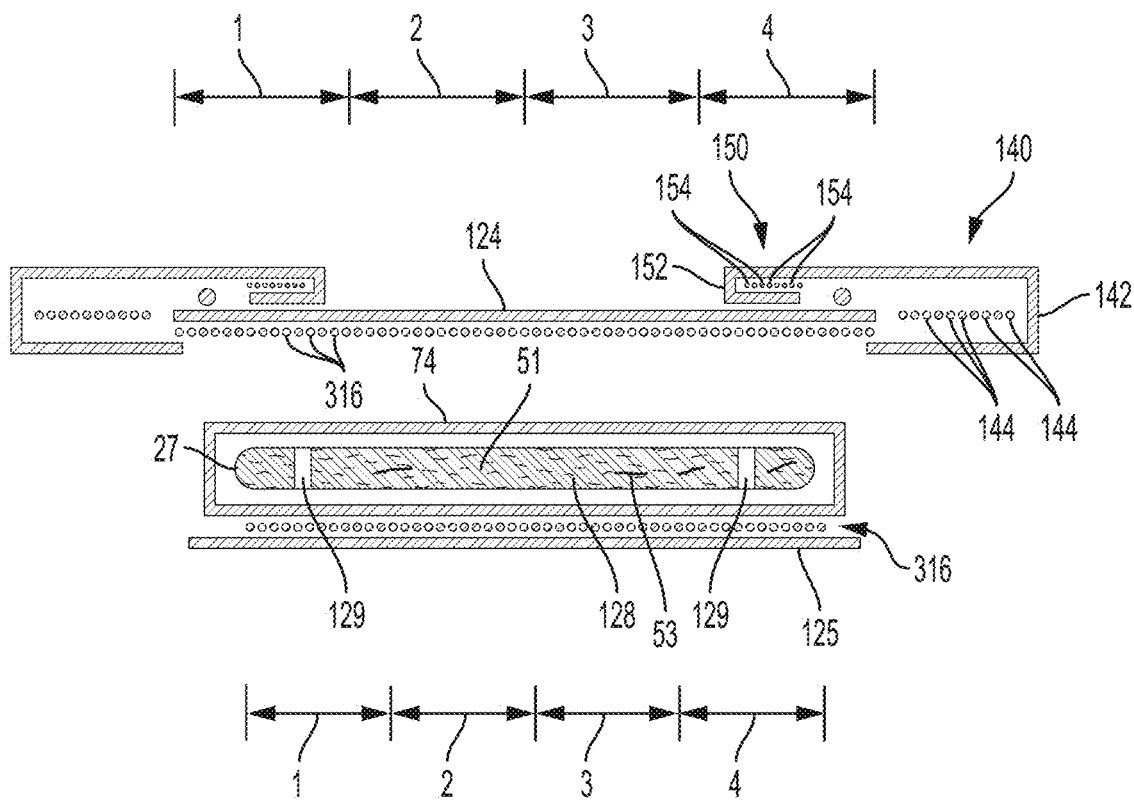
FIG. 7C is a cross section view of an alternate embodiment of the pant of FIG. 7A taken along the transverse axis, wherein the core wrap completely surrounds the core 128, wherein a plurality of elastics 316 are oriented parallel with the longitudinal axis 42 between the core wrap 74 and the backsheet 125 and oriented parallel with the longitudinal axis 42 between the core wrap 74 and the topsheet 124, and wherein the core 128 comprises AGM 51 mixed with pulp 53.

Referring to FIG. 7B, the chassis 200 may comprise a plurality of elastics 316 are oriented parallel with the longitudinal axis 42 between the backsheet nonwoven 127 and backsheet film 126. FIG. 7C shows an alternate embodiment than FIG. 7B, where the chassis 200 has a plurality of elastics 316 oriented parallel with the longitudinal axis 42 between the core wrap 74 and the backsheet 125. Still further, FIG. 7D shows another alternative embodiment where the chassis 200 comprises a plurality of elastics 316 oriented parallel with the lateral axis 44 between the backsheet film 126 and the backsheet nonwoven 127. FIG. 7B also shows a plurality of elastics 316 oriented parallel with the longitudinal axis 42 between a first topsheet layer 124a and a second topsheet layer 124b, whereas FIG. 7C shows an alternate embodiment where the plurality of elastics 316 are between the topsheet 124 and the core wrap 74. Still further, FIG. 7D shows a plurality of elastics 316 oriented parallel with the lateral axis 44 between the topsheet 124 and the core wrap 74.

Figure 12:
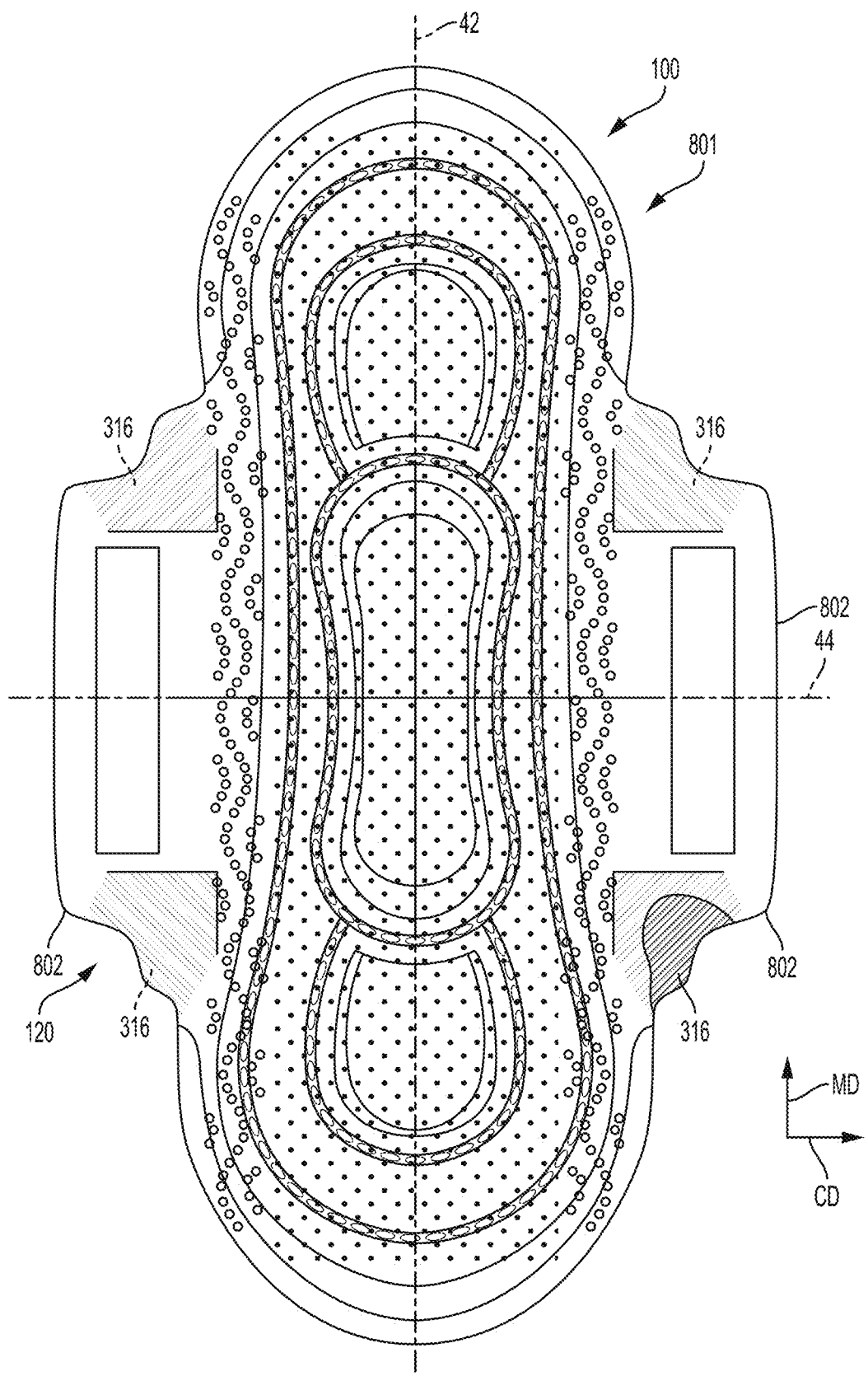
FIG. 12 is an interior plan view of a feminine hygiene article 801, specifically a pad, illustrating elasticized wings 802, where the plurality of elastics 316 are at approximately 45 degree angles relative to the longitudinal axis 42 and lateral axis 44.
Figure 12A:
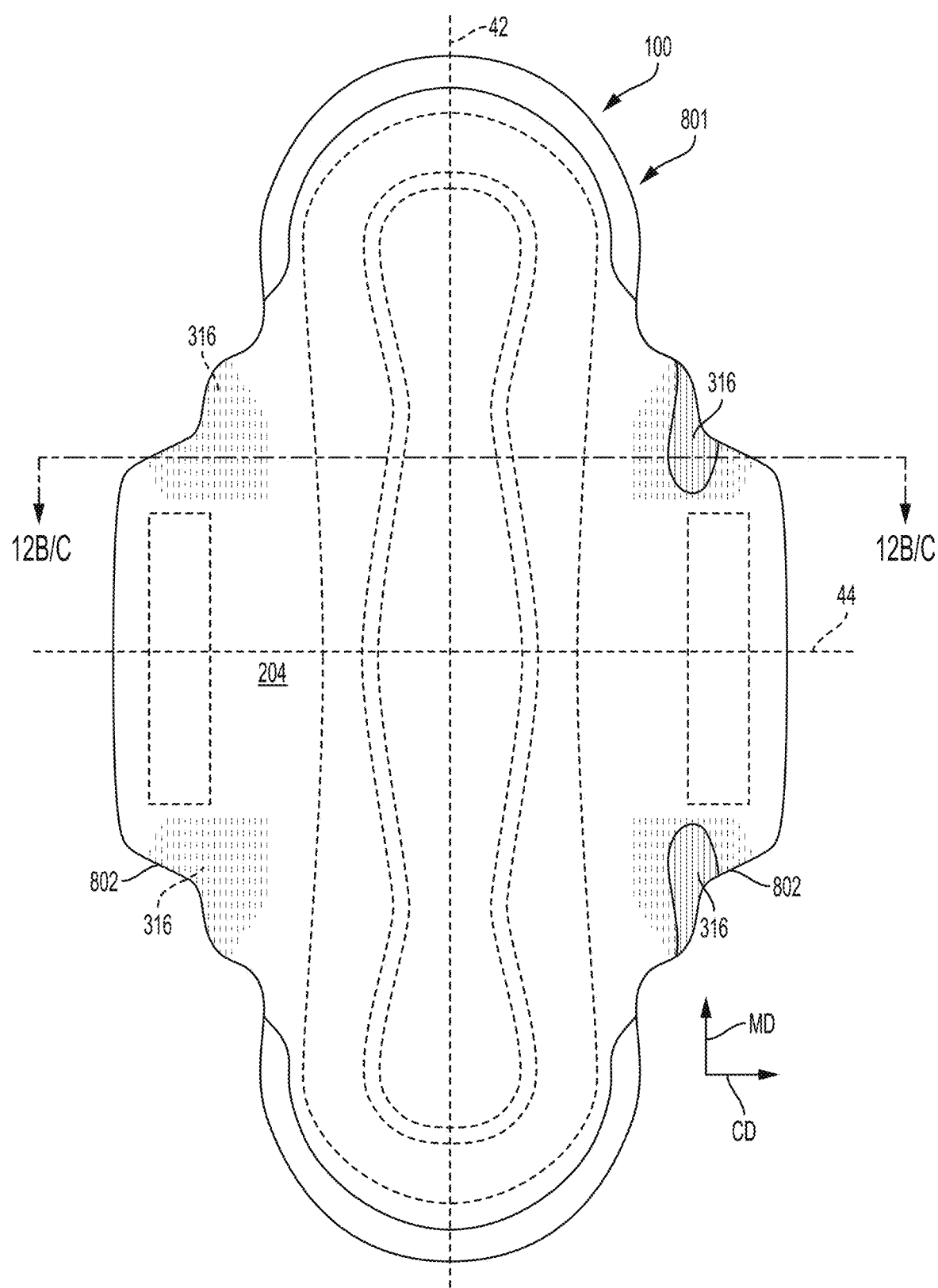
FIG. 12A is an exterior plan view of an alternative embodiment of the feminine hygiene article 801 of FIG. 12 illustrating elasticized wings 802, wherein the plurality of elastics 316 are oriented parallel with the longitudinal axis 42.
Figure 12B:
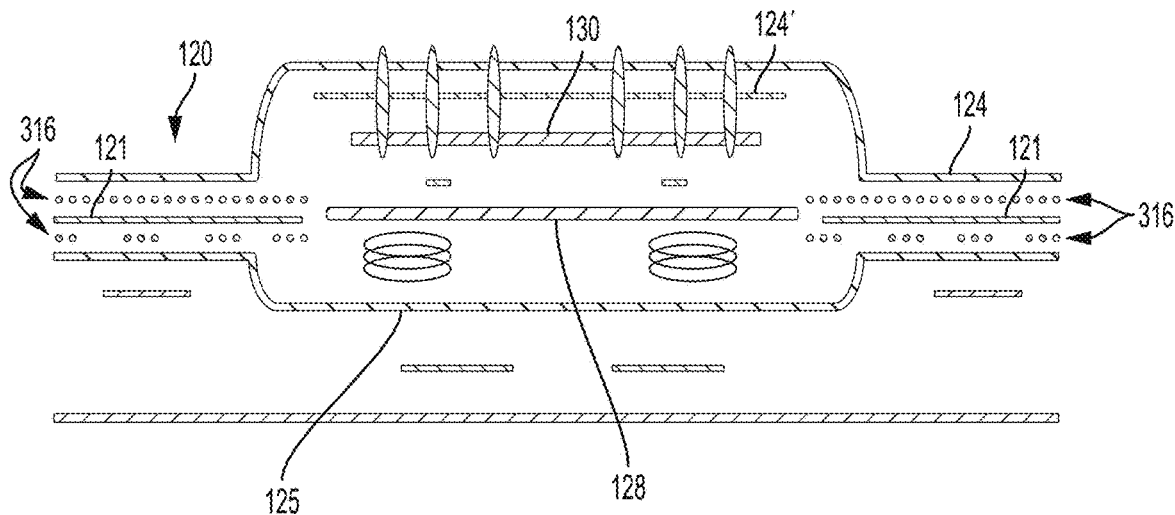
FIG. 12B is a cross section view of the feminine hygiene article 801, along line 12B/C-12B/C of the feminine hygiene article 801 of FIG. 12A, illustrating strands between the layers making up the wings.
Figure 12C:
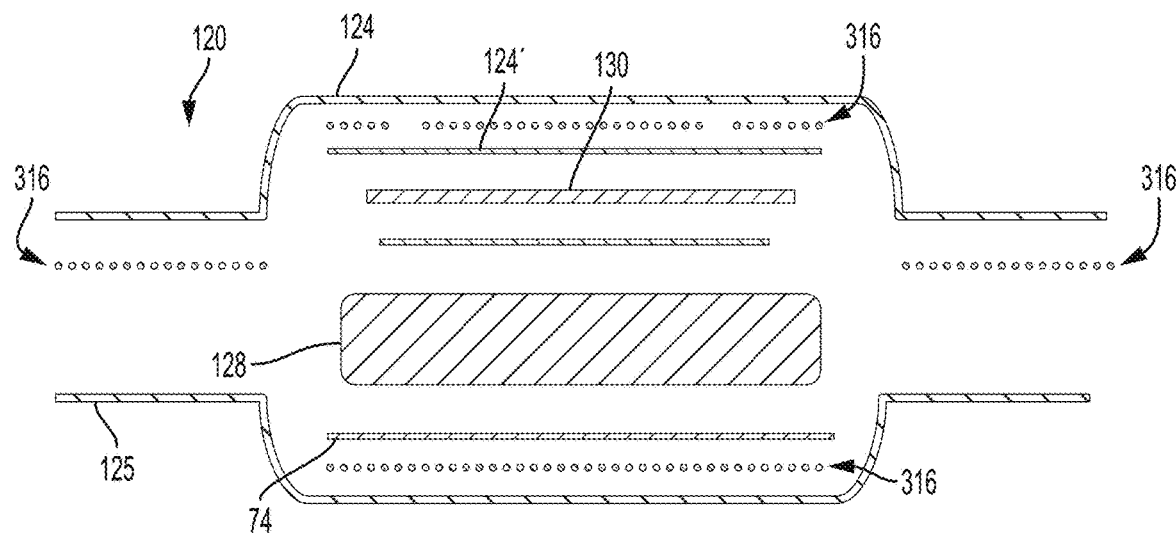
FIG. 12C is a cross section view of an alternative embodiment of the feminine hygiene article 801, along line 12B/C-12B/C of the feminine hygiene article 801 of FIG. 12A, illustrating only one layer of strands between the layers making up the wings, as well as strands underlying or forming a portion of the topsheet 124 and secondary topsheet 124'.

Still regarding an elasticized chassis 200, FIGS. 12A, B, and C show an elasticized chassis 200, where a plurality of elastics 316 are disposed between layers of the wings 120. FIG. 12 shows a plurality of elastics 316 oriented at about 45 degrees relative to the longitudinal axis 42 and the lateral axis 44. FIG. 12A is an alternate embodiment of FIG. 12, showing the plurality of elastics 316 oriented parallel with the longitudinal axis 42. FIG. 12B shows two layers of elastics 316 in the wings 120, both oriented parallel with the longitudinal axis 42, the lower layer of elastics 316 being spaced with gaps between groupings, and separated by a nonwoven wing layer 121. FIG. 12C is an alternate embodiment of FIG. 12B, where there is only one layer of elastics and no nonwoven wing layer 121. FIG. 12C also shows a plurality of elastics 316 oriented parallel with the longitudinal axis 42 between the topsheet 124 and secondary topsheet 124' (which may alternatively be oriented parallel with the lateral axis 44—not shown), and a plurality of elastics 316 oriented parallel with the longitudinal axis 42 between the backsheet film 126 and the backsheet nonwoven 127 (which may alternatively be oriented parallel with the lateral axis 44—not shown).

A portion or the entirety of the absorbent article 100 may be made to be laterally elastically extensible. The extensibility of the absorbent article 100 may be desirable in order to allow the absorbent article 100 to conform to a body of a wearer during movement by the wearer. The extensibility may also be desirable, for example, in order to allow the caregiver to extend the front waist region 36, the back waist region 38, the crotch region 37, and/or the chassis 200 to provide additional body coverage for wearers of differing size, i.e., to tailor the fit of the absorbent article 100 to the individual wearer and to aide in ease of application. Such extension may provide the absorbent article 100 with a generally hourglass shape, so long as the crotch region 37 is extended to a relatively lesser degree than the waist regions 36 and/or 38. This extension may also impart a tailored appearance to the absorbent article 100 during use.

Figure 9:
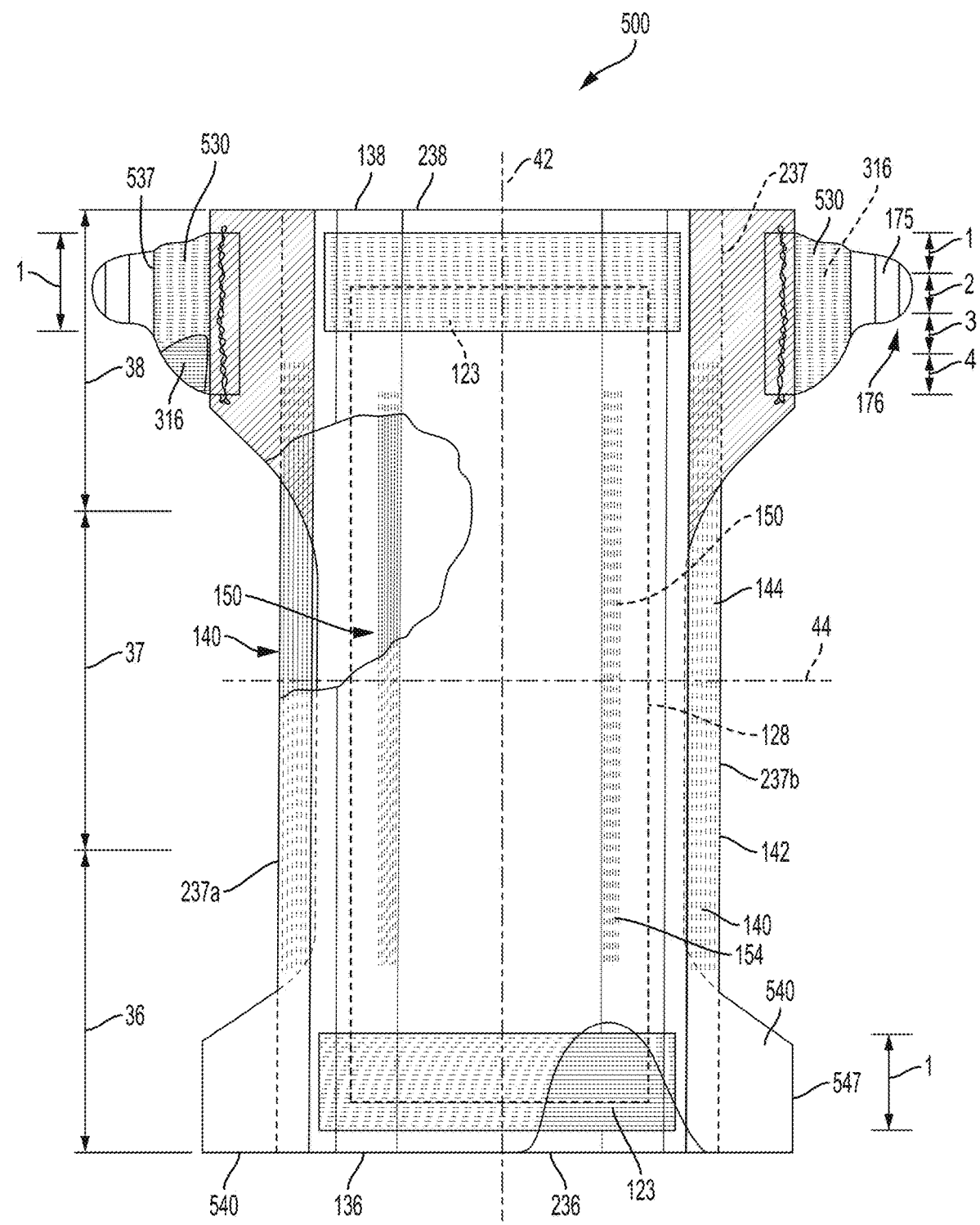
FIG. 9 is a plan view of a taped diaper comprising a pair of shaped discrete elastomeric ear panels 530 and a pair of non-elastomeric ear panels 540.
Figure 10:
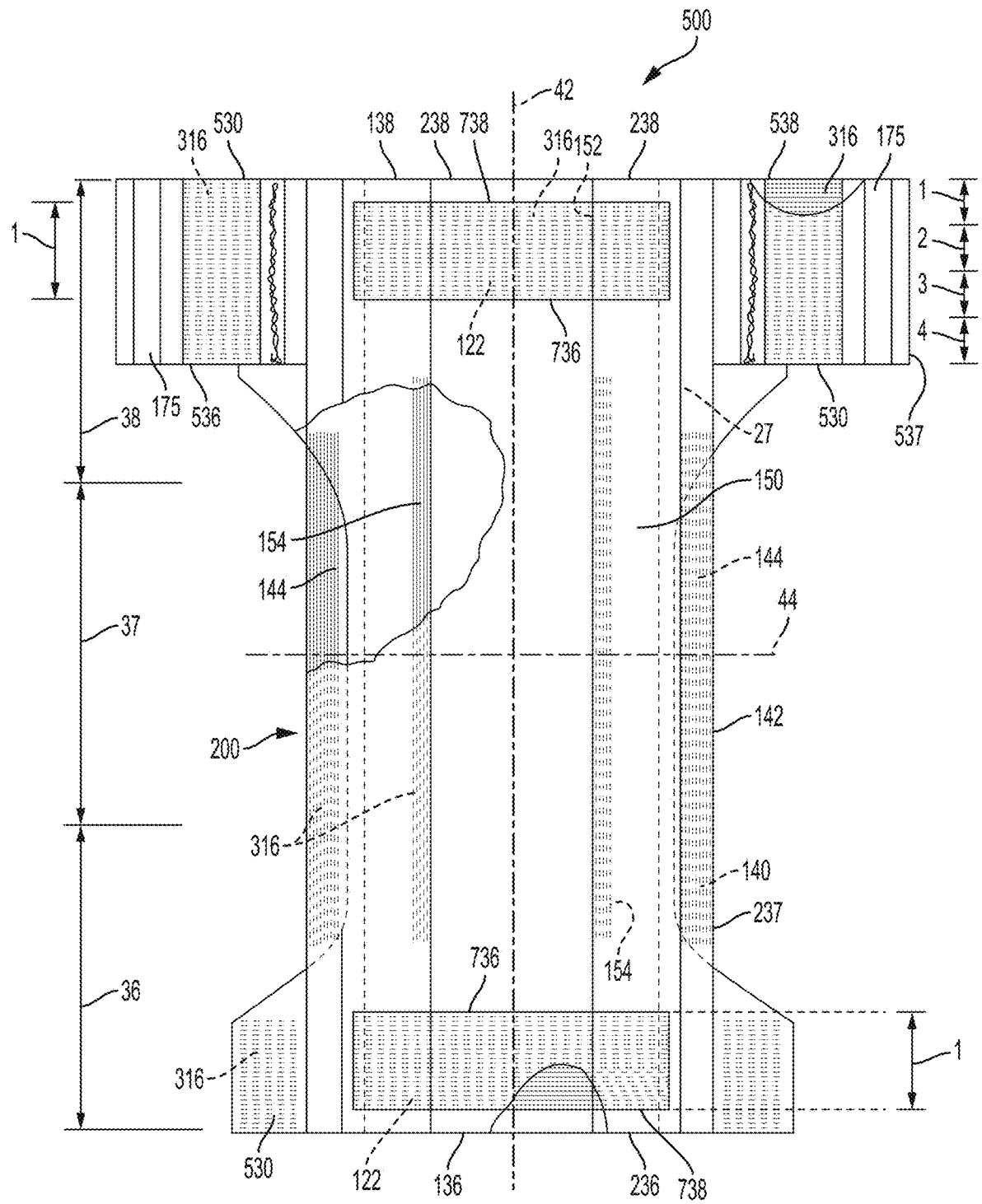
FIG. 10 is a plan view of a taped diaper comprising a pair of discrete elastomeric ear panels and a pair of non-elastomeric ear panels and a shaped backsheet.
Figure 11:
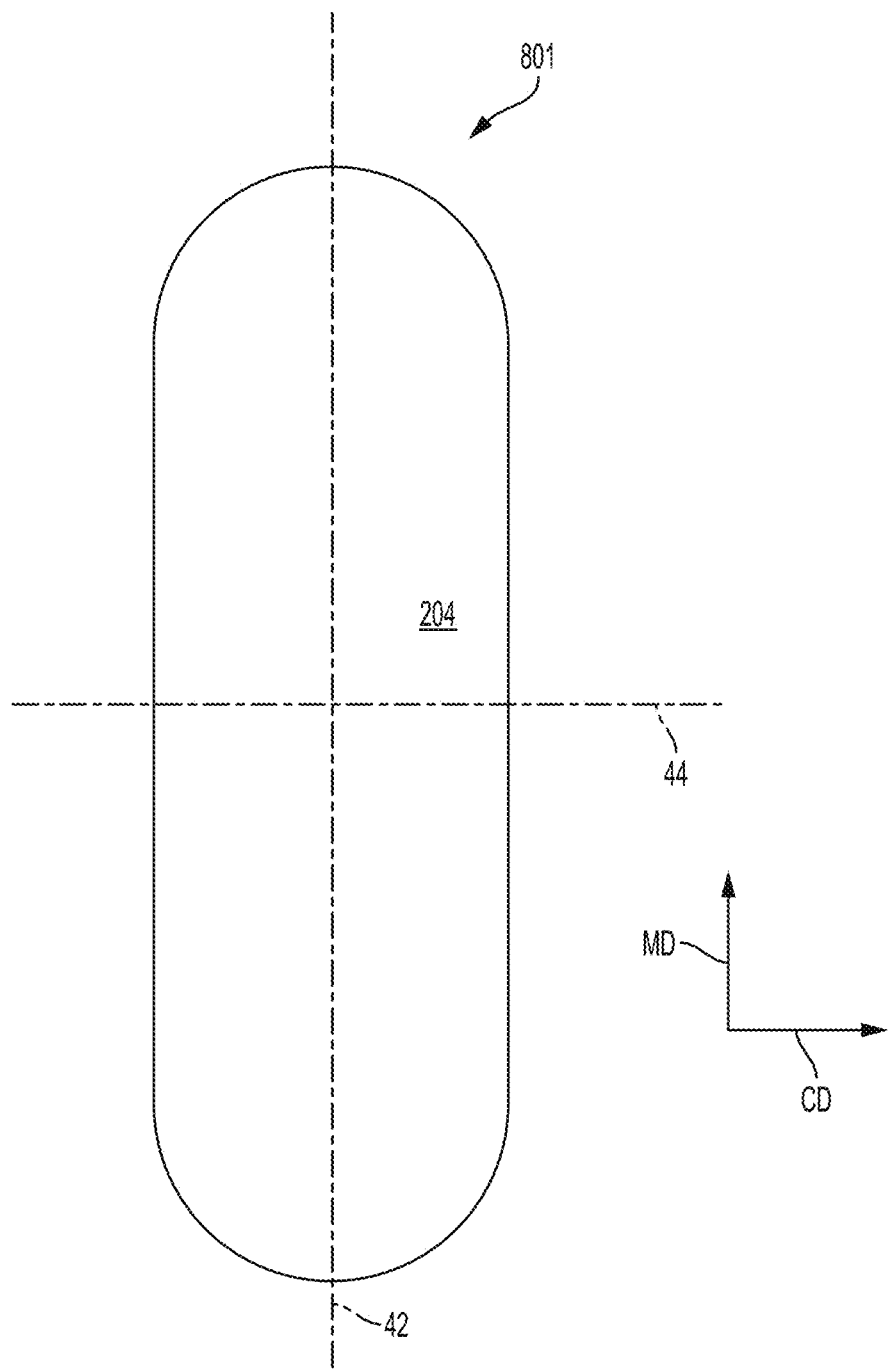
FIG. 11 is an exterior plan view of a feminine hygiene article 801, specifically a liner.
Figure 11A:
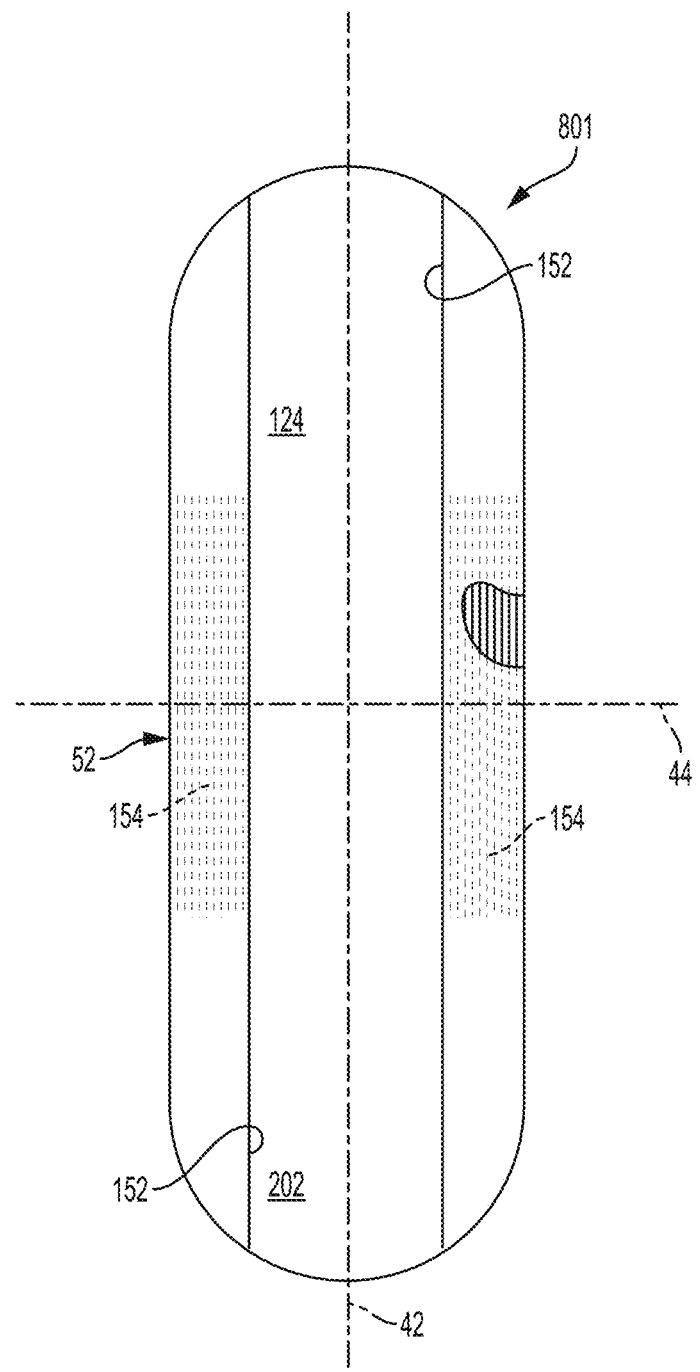
FIG. 11A is an interior plan view of the feminine hygiene article 801 of FIG. 11 illustrating leg cuffs 52.
Figure 11B:
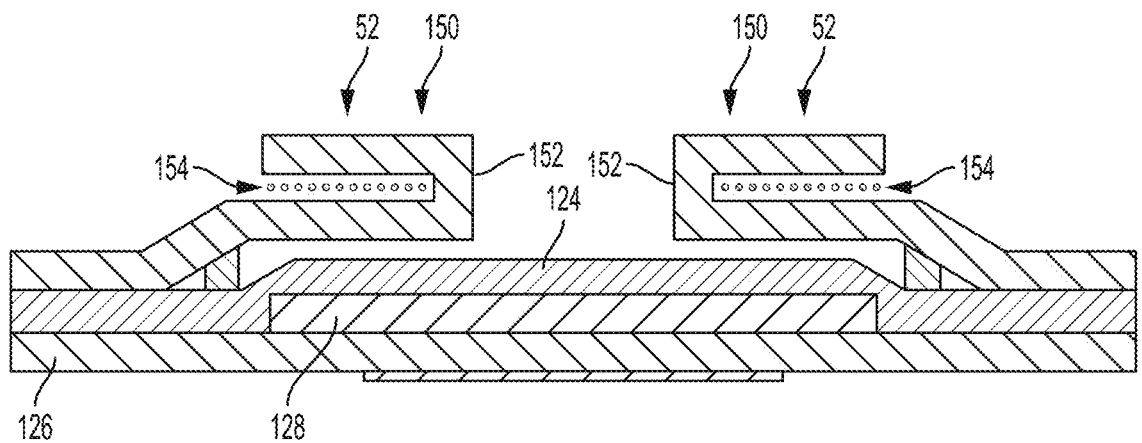
FIG. 11B is a cross section view of the feminine hygiene article 801, along the lateral axis 44 of the feminine hygiene article 801 of FIG. 9.

The chassis 200 may be substantially rectangular and may have discrete side panels 330 (FIG. 3B), extensible ear panels 530 (FIG. 9) and/or non-extensible ear panels 540 (FIG. 9) joined to the chassis 200 at or adjacent the chassis side edges 237 in one or both of the front waist region 36 and back waist region 38. Portions of one or more of the chassis side edges 237, the chassis front end edge 236 and the chassis back end edge 238 may be arcuate or curved either convexly or concavely as shown in FIGS. 11, 11A, and 10. The chassis 200 may comprise integral side panels 330 (see FIG. 4), integral extensible ear panels (see FIG. 10), integral belts 430 (see FIG. 8) or integral non-extensible ear panels 540 formed by one or more of the outer cover nonwoven, backsheet film, outer leg cuff material, topsheet or core wrap 74 disposed in one or both of the front and back waist regions (FIG. 9). Alternatively, the chassis 200 may comprise discrete side panels 330 (see FIG. 3B), discrete extensible ear panels 530 (see FIGS. 9, 9A, and 10), or discrete belts 430 (FIGS. 5-7D). The chassis may be shaped or non-rectangular, in one waist region and substantially rectangular in the opposing waist region. Alternatively, the chassis may be substantially rectangular in one or both of the waist regions and non-rectangular in the crotch region.

Absorbent articles of the present disclosure may comprise a plurality of laterally extending elastics wherein the elastics are present in a first waist region, the crotch region and in the opposing second waist region.

Closed-Form Pant Article

Figure 3:
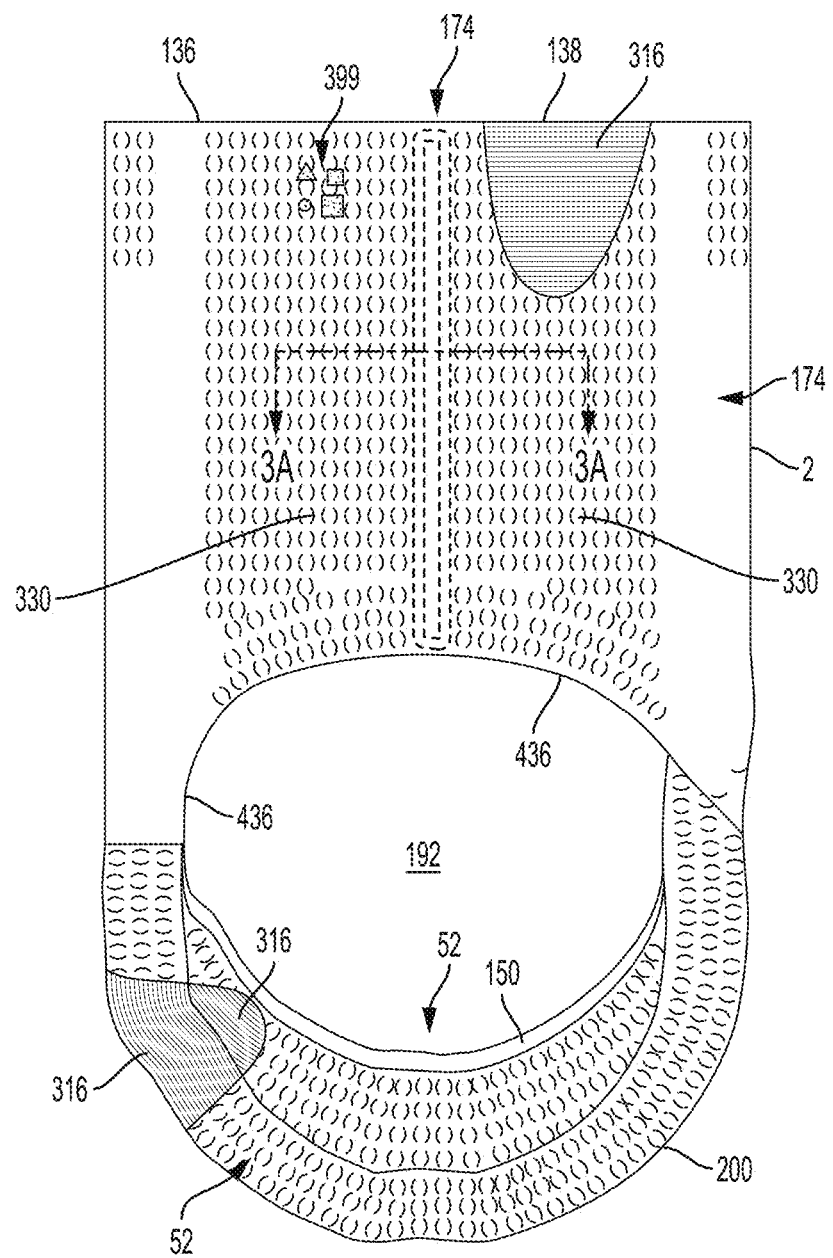
FIG. 3 is a side view of a pant comprising side panels with refastenable side seams.
Figure 3B:
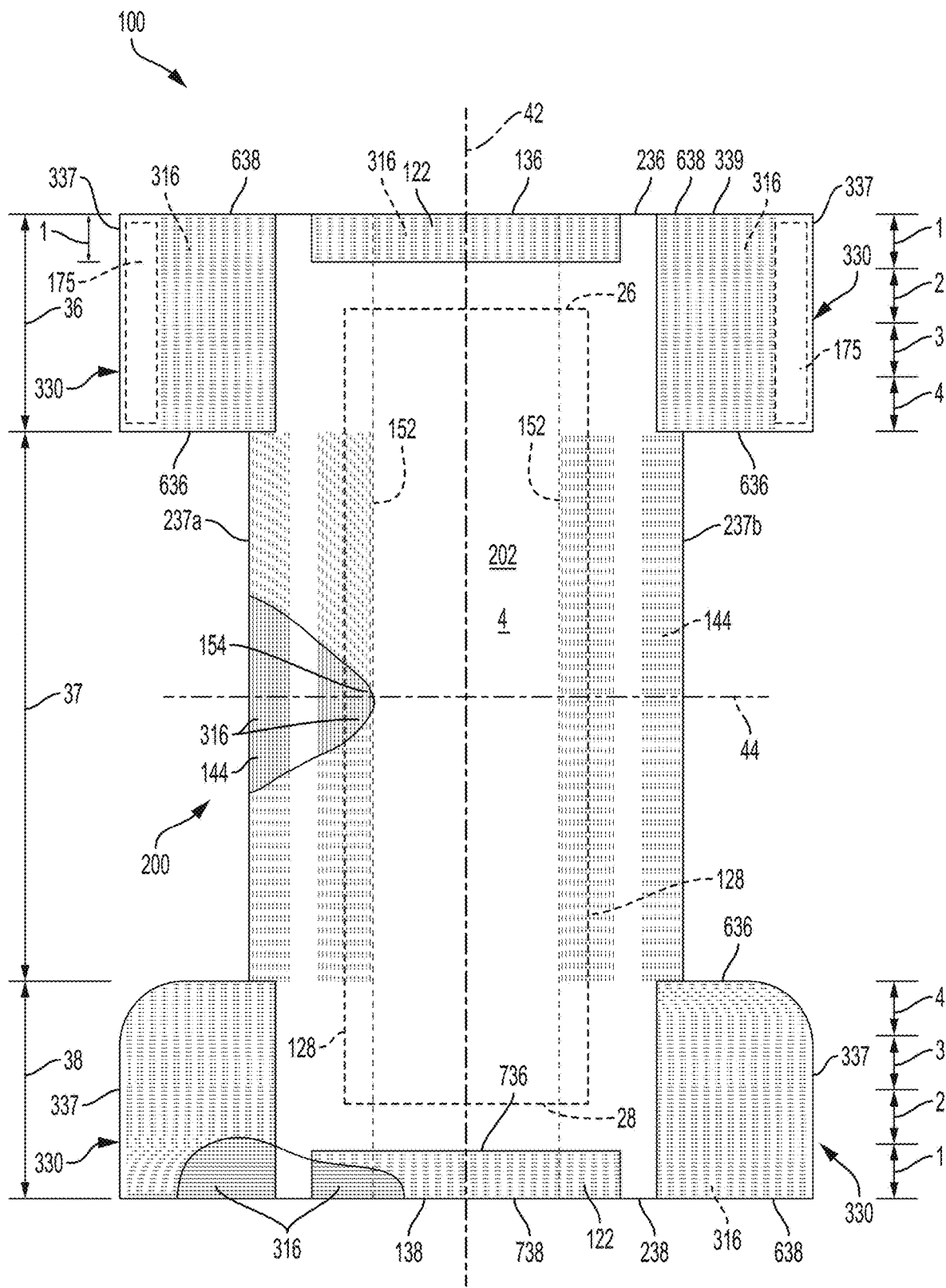
FIG. 3B is a plan view of the pant illustrated in FIG. 3, prior to joining the side panels to form the waist and leg openings.
Figure 4:
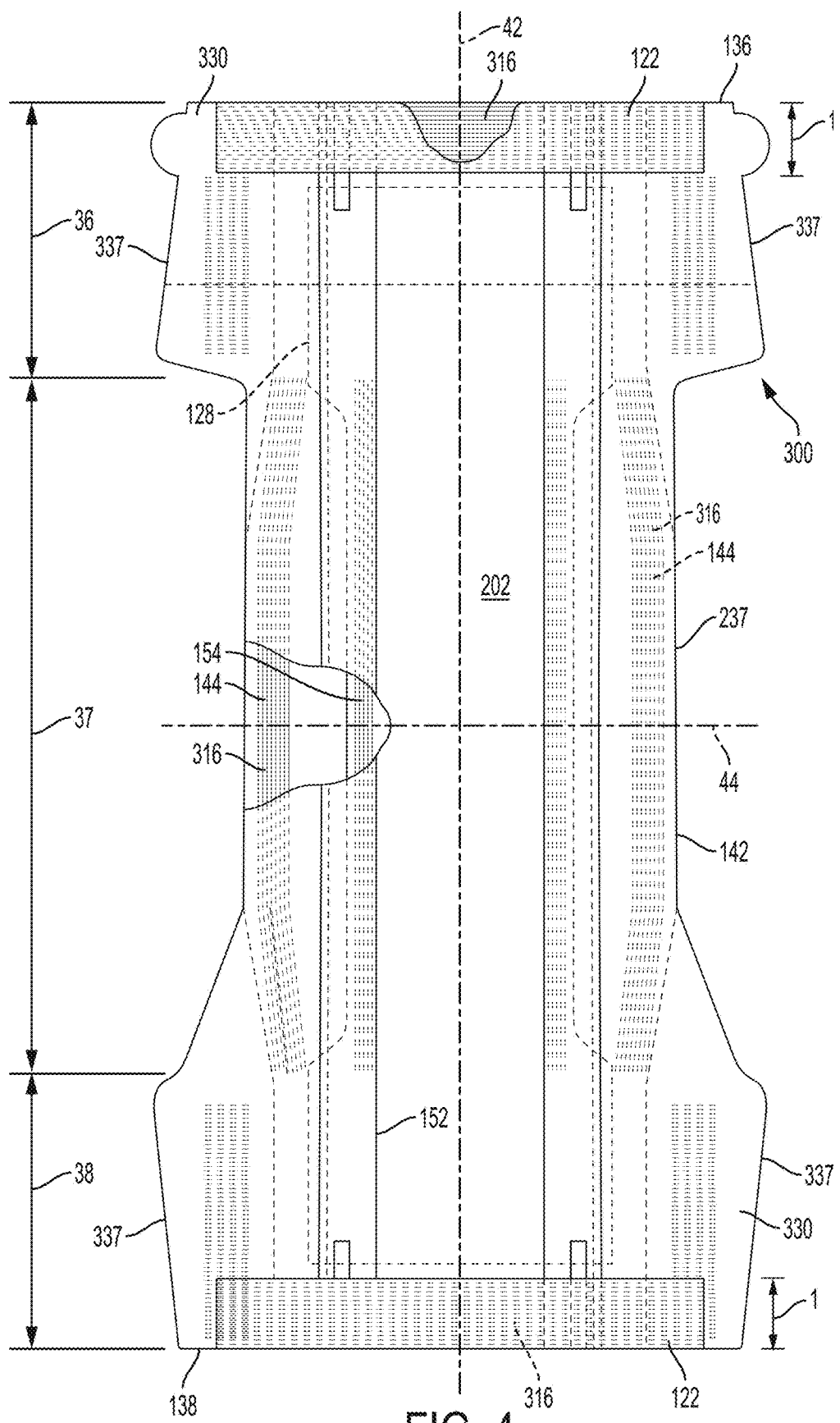
FIG. 4 is a plan view of a pant comprising integral side panels, prior to joining the side panels to form the waist and leg openings.
Figure 8:
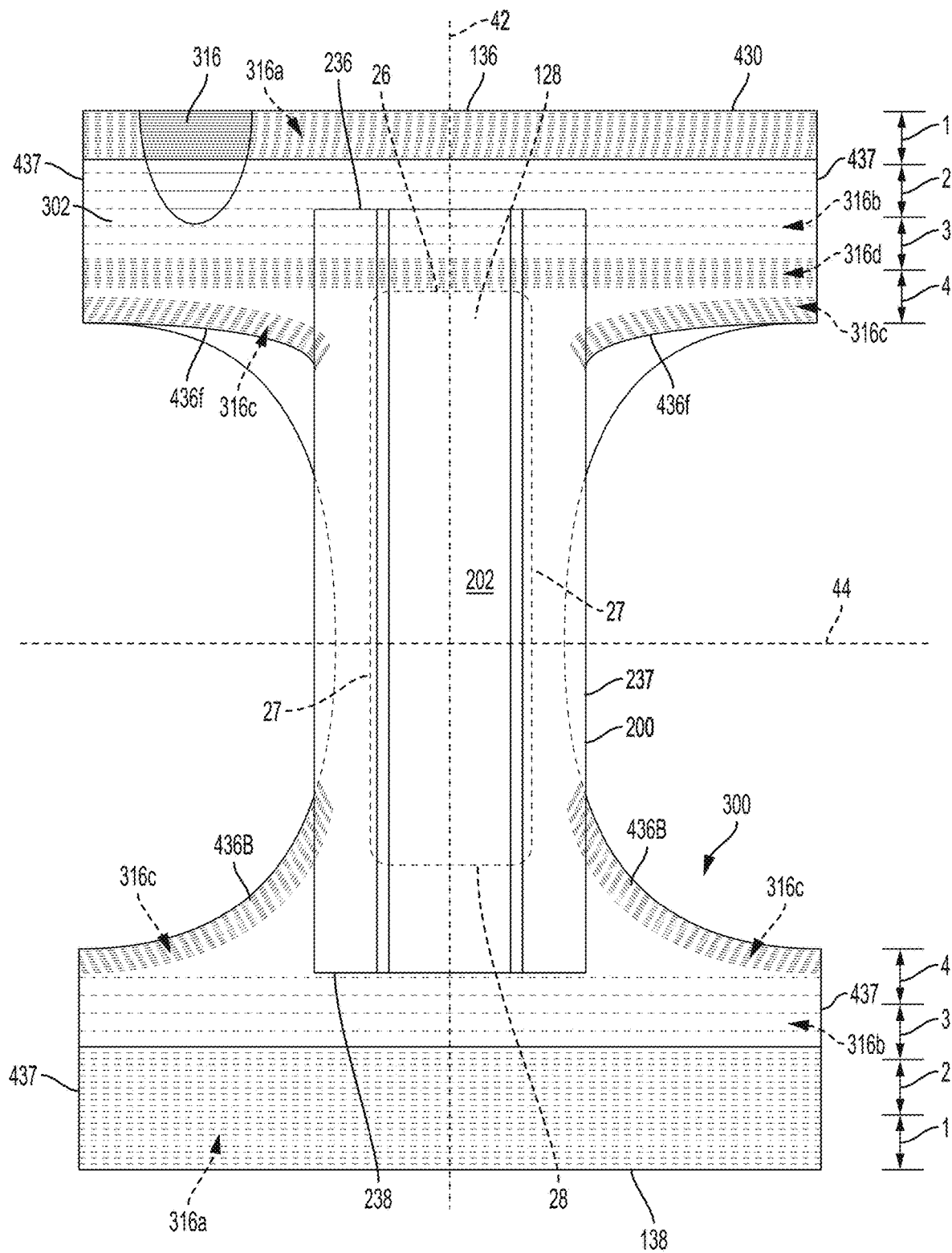
FIG. 8 is a plan view of a pant prior to joining side edges of the belts to form the waist and leg openings, illustrating multiple beamed elastic zones disposed in the low motion zones of a potential wearer.

Closed-form, pant-style, absorbent articles are generally disclosed in FIGS. 3-8, and are designed to be packaged in closed-form having a waist opening 190 and two leg openings 192, and designed to be donned onto the wearer like a pair of durable underwear. The pant may comprise discrete elastomeric side panels 330 (FIG. 3B) and/or discrete belts 430 (FIG. 7) in one or both of the front waist region 36 and back waist region 38. Alternatively, the side panels 330 and/or belts 430 may be formed integrally with other elements of the article such as the chassis 200 (FIGS. 4 and 8).

Figure 5:
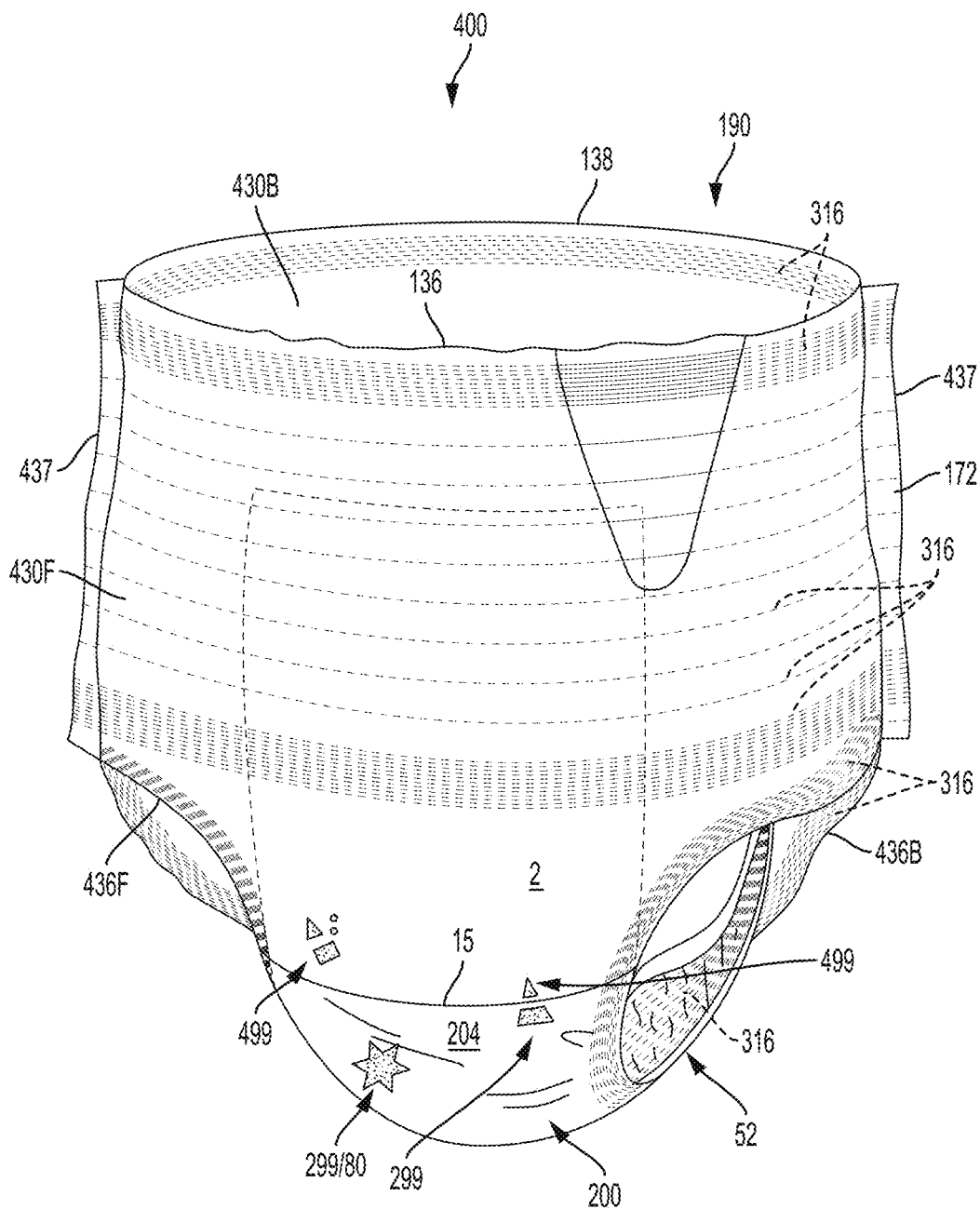
FIG. 5 is a perspective front view of a pant comprising belts comprising multiple elastics zones.
Figure 5A:
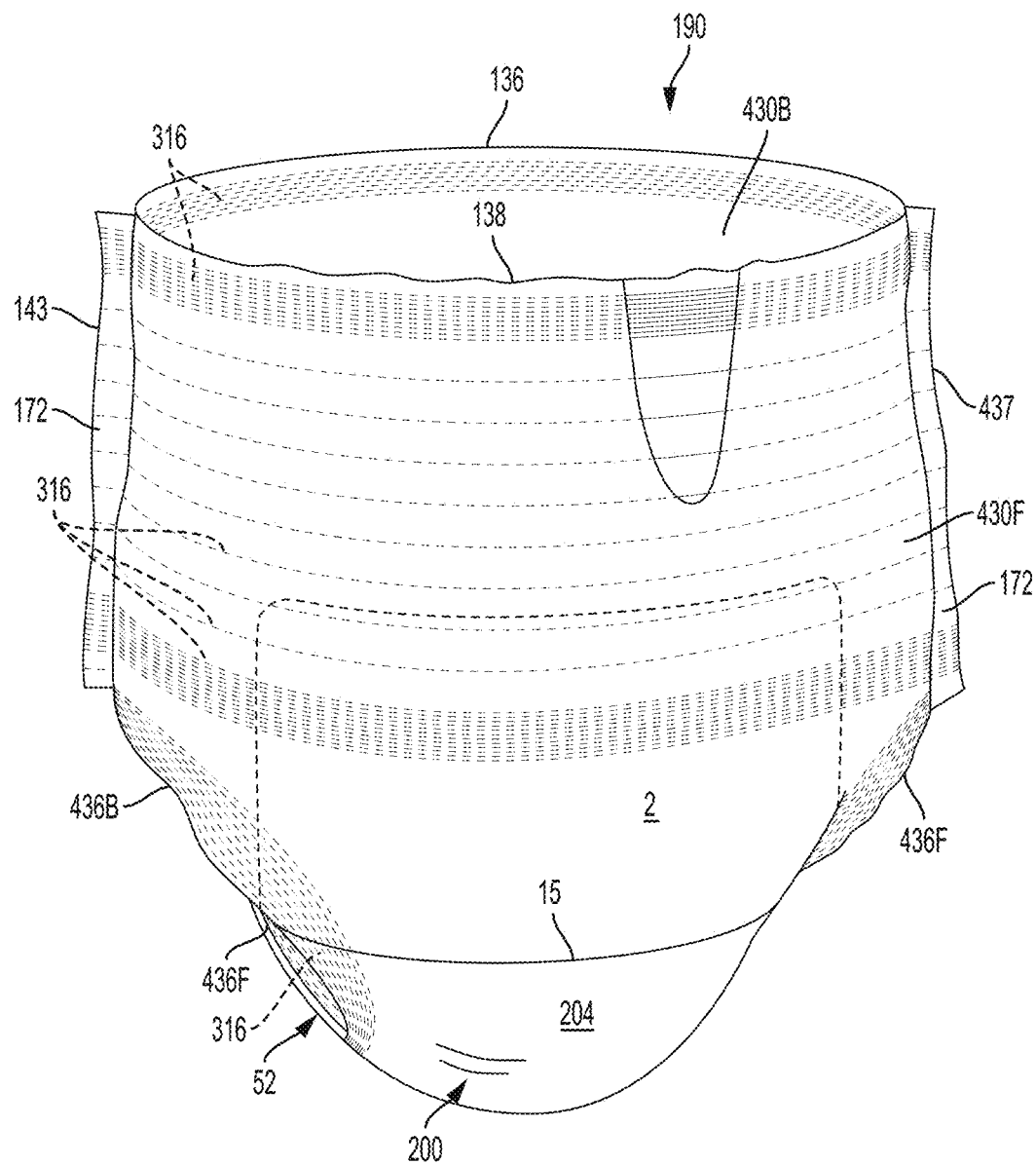
FIG. 5A is a perspective back view of the pant of FIG. 5
Figure 6:
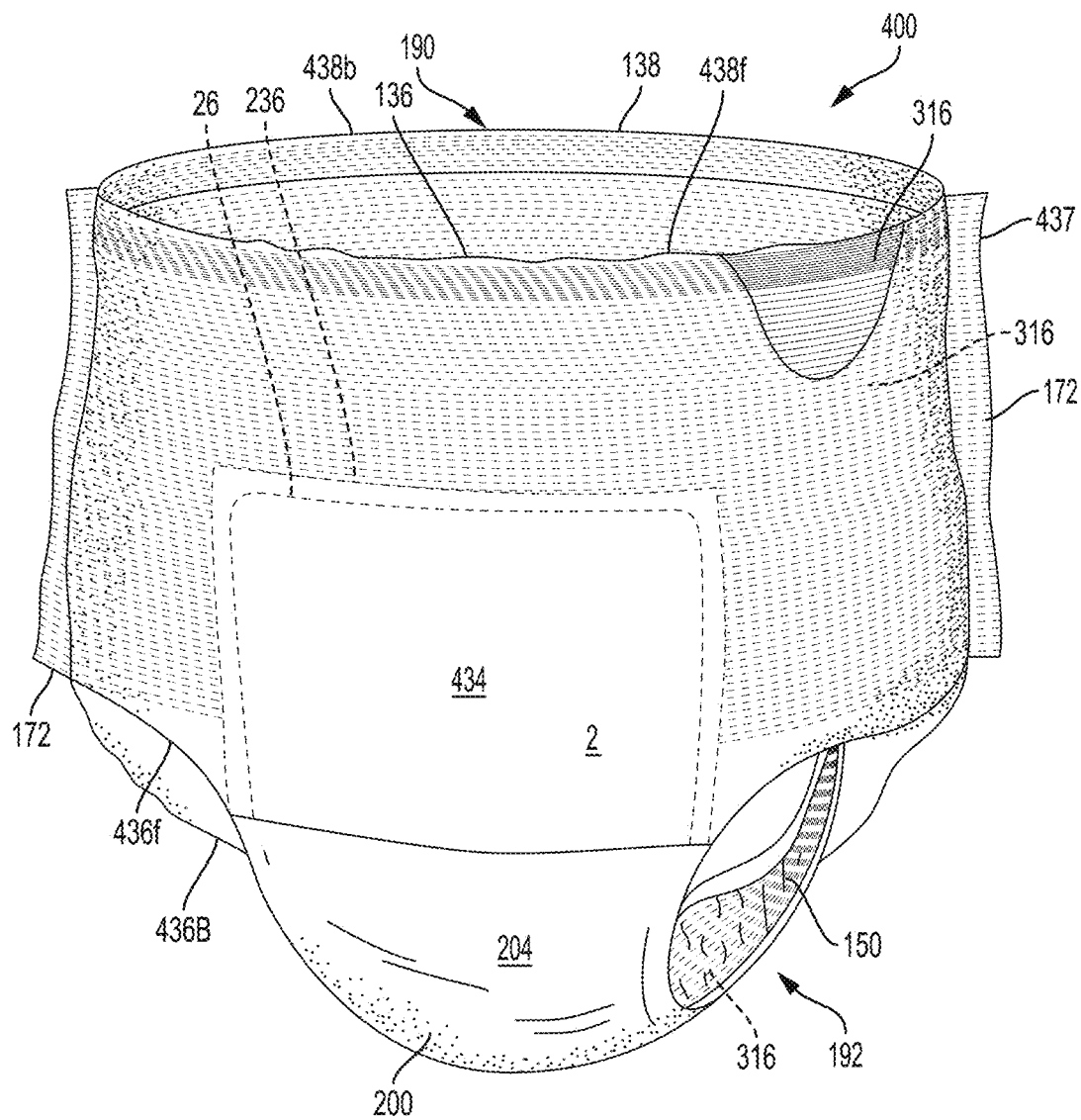
FIG. 6 is a perspective front view of a pant comprising discrete belts having both continuous and discontinuous elastics.

When the absorbent article comprises front and back belts 430, the sides of front and back belts 430 may be joined permanently or refastenably to each other and the front and back side panels on one side of the article may be joined permanently or refastenably to each other to create a waist opening 190 and a pair of leg openings 192 (FIGS. 5, 5A, and 6). The belts 430 provide an elastically extensible feature that provides a more comfortable and contouring fit by initially conformably fitting the article 100 to the wearer and sustaining this fit throughout the time of wear well past when the pant has been loaded with exudates since the elastomeric side panels allow the sides of the pant to expand and contract. Further, the elastomeric belts 430 provide ease of application and develop and maintain wearing forces and tensions to maintain the article 100 on the wearer and enhance the fit, especially when beamed elastomeric laminates are used to form the belts 430. The elastomeric side panels enable ease of application allowing the pant to be pulled conformably over the hips of the wearer and positioned at the waist where the belts 430 conform to the body and provide tension sufficient to maintain the articles position on the wearer. The tension created by the belts 430 is transmitted from the elastic belts 430 along the waist opening 190 and along at least a portion of the leg opening 192. Typically, particularly regarding discrete side panels 330, the chassis 200 is disposed between the side panels 330 and extends to form a portion of the waist edge 136 and/or 138 of the pant comprising side panels 330. In other words, a portion of the waist edge 136 and/or 138 in one or both of the front waist region 36 and back waist region 38 may be formed in part by the side panels 330 and in part by the chassis 200.

Figure 3A:
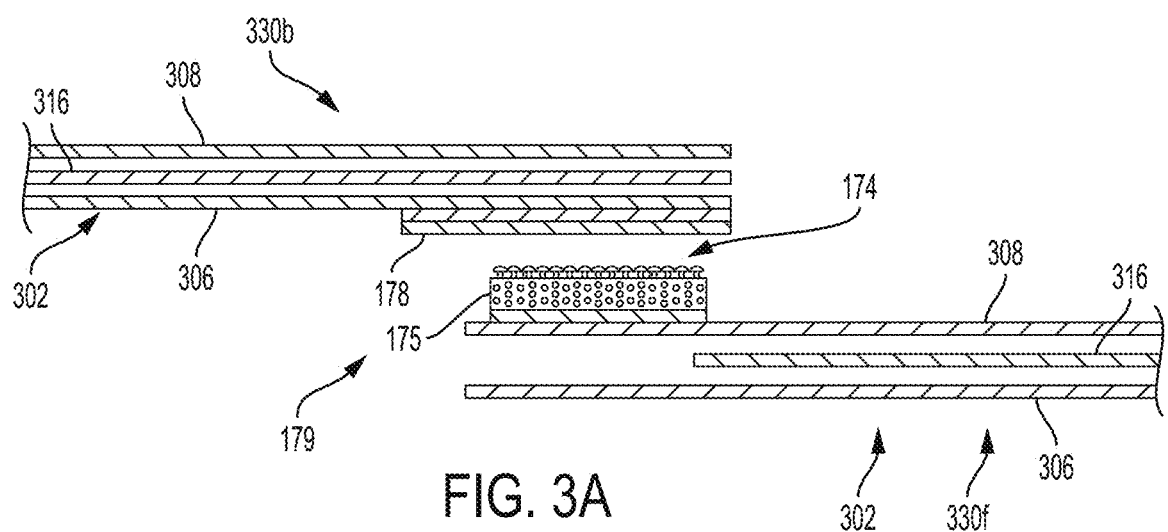
FIG. 3A is a cross section view of a refastenable seam taken along line 3A-3A of the pant of FIG. 3.

The pant comprising side panels 330 may also comprise a pair of laterally opposing refastenable seams 174 as illustrated in FIGS. 3 and 3A. The refastenable side seam 174 may be formed by refastenably joining an interior surface of a portion of the article, e.g. a side panel 330, to an exterior surface of another portion of the article 100, e.g., a longitudinally opposing side panel 330 or the chassis 200 to form the refastenable side seam 174. FIG. 3A illustrates a front side panel 330f comprising a fastener 175 comprising hooks facing away from a wearer (the fastener 175 disposed on an exterior surface of the front side panel 330f) that refastenably attaches to a mating fastener 178 (loops or a suitable nonwoven in FIG. 3A), the mating fastener 178 being disposed on an interior surface of the back side panel 330b. Observe that that FIG. 3A is an alternative embodiment of FIGS. 3 and 3B as the pant of FIGS. 3 and 3B do not comprise a mating fastener 178—rather, the fastener 175 in FIGS. 3 and 3B refastenably join directly to the back side panels 330.

The pant comprising belts 430 may also comprise a first permanent side seam 172 and a laterally opposing second permanent side seam 172 as illustrated, for example, in FIGS. 5, 5A, and 6. The permanent side seam 172 may be formed by joining an interior surface of a portion of the article 100, e.g. a belt 430, to an exterior surface of another portion of the article 100, e.g. a longitudinally opposing belt 430 or the chassis 200 to form the permanent side seam 172. Alternatively, the permanent side seam 172 may be formed by joining an interior surface of a portion of the article 100, e.g. a belt 430, to an interior surface of another portion of the article 100, e.g. a longitudinally opposing belt 430 to form the permanent side seam 172. Any pants comprising side panels 330 configurations described above may comprise a waistband 122 wherein at least a portion of the waistband 122 (as illustrated in FIG. 3B) is disposed at or immediately adjacent the waist edge 136 and/or 138 and overlaps a portion of the center chassis 200. The waistband 122 may extend laterally to overlap portions of the inner leg cuffs 150 and/or portions of the elastomeric side panels 330. The waistband 122 may be disposed on the interior surface 202 of the chassis 200 or alternatively between the topsheet 124 and the backsheet 125.

Particularly regarding belts 430, as illustrated in FIG. 7E, the inner belt layer 432 and/or the outer belt layer 434 of the first and second elastomeric belts 430 may be formed by a common belt layer as shown in FIG. 7E. When the first and second elastomeric belts 430 have a common belt layer, the common belt layer may extend from a first waist edge in a first waist region to a longitudinally opposing second waist edge in a second waist region, i.e. front waist edge 136 to back waist edge 138.

Also particularly regarding belted pants 400, as illustrated in FIGS. 7 and 7A, the belt pant 400 may have a first elastomeric belt 430 disposed in a first waist region having a first longitudinal length and a second elastomeric belt 430 disposed in a second waist region having a second longitudinal length wherein the longitudinal length of the first belt is greater than the longitudinal length of the second belt along the side edge of the belt at or adjacent the side seam. This length difference helps provide buttock coverage in the back of the pant providing a more underwear-like appearance. And, while this advantage is disclosed for belted pants 400, there is also an advantage in having longitudinally longer side panels 330 in the back waist region 38.

Open-Form Taped Article

Open-form, taped-style, absorbent articles are generally disclosed in FIGS. 9-10. The taped diaper 500, open-form article, as illustrated in FIGS. 9 and 10 may comprise elastomeric ear panels 530 in one or both of the front waist region 36 and back waist region 38. The elastomeric ear panels 530 may be unitary structurally with other elements of the article 100 or as a separate element joined to another element of the article 100. The elastomeric ear panels 530 provide an elastically extensible feature that provides a more comfortable and contouring fit by initially conformably fitting the article 100 to the wearer and sustaining this fit throughout the time of wear well past when the taped diaper 500 has been loaded with exudates since the elastomeric ear panels 530 allows the diaper to expand and contract to fit the wearer. Further, the elastomeric ear panels 530 develop and maintain wearing forces (tensions) and enhance the tensions developed and maintained by the fastening system 179 (including the fasteners 175 (e.g., hooks) that may be releasably engaged with a mating fasteners 178 (e.g., loops)), to maintain the article 100 on the wearer and enhance the fit. The elastomeric ear panels 530 especially assist in maintaining the primary line of tension formed by the fastening system 179 allowing the diaper to conformably fit over the hips of the wearer where there is dynamic motion, and initially pre-tensioning the waist opening 190 and leg opening 192 since the diaperer typically stretches the elastomeric ear panels 530 when applying the taped diaper 500 on the wearer so that when the elastomeric ear panels 530 contract, tension is transmitted from the elastomeric ear panels 530 along the waist opening 190 and along at least a portion of the leg opening 192. While the open-form article of the present disclosure may have the elastomeric ear panels 530 disposed in the back waist region 38, alternatively, the taped diaper 500 may be provided with elastomeric ear panels 530 disposed in the front waist region 36 or in both the front waist region 36 and the back waist region 38. The open-form article may also have elastomeric ear panels 530 disposed in a first waist region and elastomeric ear panels 530 or non-elastomeric ear panels 540 disposed in a second waist region.

In an alternative embodiment the open-form, taped-style, absorbent articles may comprise an elastomeric belt 430 disposed in one of the waist regions. The elastomeric belt 430 may be joined and/or positioned in a particular place or position and may be unitary structurally with other elements of the article 100 or as a separate element joined to another element of the article 100. A belted taped diaper the elastomeric belt 430 may be disposed in the back waist region 38. The elastomeric belt 430 may have fasteners disposed at or adjacent the laterally opposing ends of the belt. Fasteners 175 may be disposed on the interior surface of the belt 430 to engage with a discrete mating fastening component 178 or with the exterior surface 204 of the article (like the backsheet nonwoven 127) to fasten the article on the wearer.

Outer Cover Material

The backsheet 125 may comprise a backsheet film 126 and backsheet nonwoven 127. The backsheet nonwoven 127 may also be referred to as the outer cover material. The outer cover material forms at least a portion of the garment-facing surface of the absorbent article 100 and effectively "covers" the backsheet film 126 so that the film is not present on the garment-facing surface. The outer cover material may comprise a bond pattern, apertures, and/or three-dimensional features.

Absorbent Core

As used herein, the term "absorbent core" 128 refers to the component of the absorbent article 100 having the most absorbent capacity and that comprises an absorbent material. Referring to FIGS. 7, 7B, and 7C, in some instances, absorbent material (e.g., 51 and 53) may be positioned within a core bag or a core wrap 74. The absorbent material may be profiled or not profiled, depending on the specific absorbent article. The absorbent core 128 may comprise, consist essentially of, or consist of, a core wrap, absorbent material, and glue enclosed within the core wrap. The absorbent material may comprise superabsorbent polymers, a mixture of superabsorbent polymers and air felt, only air felt, and/or a foam. In some instances, the absorbent material may comprise at least 80%, at least 85%, at least 90%, at least 95%, at least 99%, or up to 100% superabsorbent polymers, by weight of the absorbent material. In such instances, the absorbent material may free of air felt, or at least mostly free of air felt—in such cases the AGM 51 may be held in place by an adhesive 54, such as a thermoplastic adhesive. And, for swim diapers, the article may be free of superabsorbent polymers. The absorbent core periphery, which may be the periphery of the core wrap, may define any suitable shape, such as rectangular, "T," "Y," "hour-glass," or "dog-bone" shaped, for example. An absorbent core periphery having a generally "dog bone" or "hour-glass" shape may taper along its width towards the crotch region 37 of the absorbent article 100.

Referring to FIGS. 7, 7B, and 7C, the absorbent core 128 may have areas having little or no absorbent material, where a wearer-facing surface of the core bag 74 may be joined to a garment-facing surface of the core bag 74. These areas having little or no absorbent material may be referred to as "channels" 129. These channels can embody any suitable shapes and any suitable number of channels may be provided. In other instances, the absorbent core may be embossed to create the impression of channels. The absorbent core in FIGS. 7, 7B, and 7C is merely an example absorbent core. Many other absorbent cores with or without channels are also within the scope of the present disclosure.

As used herein, a loaded absorbent core is one holding (or capable of holding) a load of at least 50, 100, or 200 milliliters (mls) for diapers, pants, and adult incontinence articles. The disposable absorbent articles of the present disclosure comprising an absorbent core are designed to fit the wearer with an empty absorbent core (i.e., one that is not loaded), as well as being capable of fitting the wear for an appreciable time (2 or more hours) even when the core is loaded.

Acquisition Materials

One or more acquisition materials (e.g., 130) may be present at least partially intermediate the topsheet 124 and the absorbent core 128. The acquisition materials are typically hydrophilic materials that provide significant wicking of bodily exudates. These materials may dewater the topsheet 124 and quickly move bodily exudates into the absorbent core 128. The acquisition materials 130 may comprise one or more nonwoven materials, foams, cellulosic materials, cross-linked cellulosic materials, air laid cellulosic nonwoven materials, spunlace materials, or combinations thereof, for example. In some instances, portions of the acquisition materials may extend through portions of the topsheet 124, portions of the topsheet 124 may extend through portions of the acquisition materials, and/or the topsheet 124 may be nested with the acquisition materials. Typically, an acquisition material or layer may have a width and length that are smaller than the width and length of the topsheet 124. The acquisition material may be a secondary topsheet in the feminine pad context. The acquisition material may have one or more channels as described in the absorbent core 128 section (including the embossed version). The channels in the acquisition material may align or not align with channels in the absorbent core 128. In an example, a first acquisition material may comprise a nonwoven material and as second acquisition material may comprise a cross-linked cellulosic material.

Landing Zone

Figure 9A:
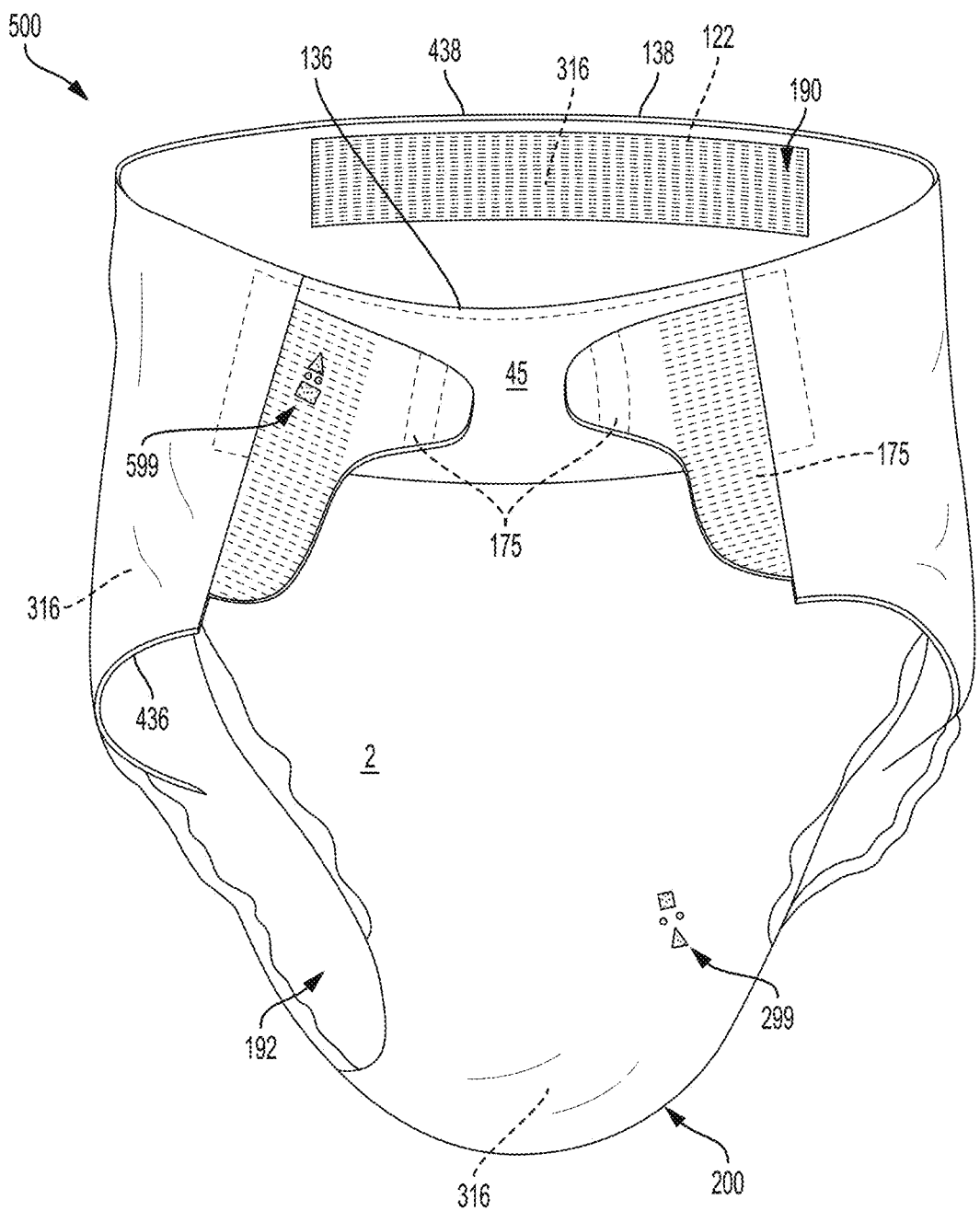
FIG. 9A is a perspective front view of the taped diaper of FIG. 9.

Referring to FIG. 9A, the absorbent article 100 may have a landing zone area 45 that is formed in a portion of the garment-facing surface 2 of the outer cover material. The landing zone area 45 may be in the back waist region 38 if the absorbent article 100 fastens from front to back or may be in the front waist region 36 if the absorbent article 100 fastens back to front. In some instances, the landing zone 45 may be or may comprise one or more discrete nonwoven materials that are attached to a portion of the outer cover material in the front waist region 36 or the back waist region 38 depending upon whether the absorbent article fastens in the front or the back. In essence, the landing zone 45 is configured to receive the fasteners 175 and may comprise, for example, a plurality of loops configured to be engaged with, a plurality of hooks on the fasteners 175, or vice versa.

Wetness Indicator/Graphics

The absorbent articles 100 of the present disclosure may comprise graphics (e.g., a chassis graphic 299, a side panel graphic 399, a belt graphic 499, or an ear panel graphic 599) and/or wetness indicators 80 that are visible from the garment-facing surface 2. The graphics may be printed on the landing zone 45, the backsheet 125, topsheet 124, belts 430, side panels 330, ear panels 530 and/or at other locations. The wetness indicators are typically applied to the absorbent core facing side of the backsheet film 126, so that they can be contacted by bodily exudates within the absorbent core 128. In some instances, the wetness indicators may form portions of the graphics e.g., 299. For example, a wetness indicator may appear or disappear and create/remove a character within some graphics. In other instances, the wetness indicators 80 may coordinate (e.g., same design, same pattern, same color) or not coordinate with the graphics. Alternatively, graphics and/or wetness indicators 80 may be disposed on, and/or visible from, the wearer-facing surface 204.

One or more of the side/ear panels 330, 530 may comprise a graphic disposed thereon. One or more of the elastomeric side/ear panels 330, 530 comprise a graphic (e.g., 399, 599) substantially aligned to a chassis graphic 299 to form a composite graphic element. Further, the front and back belts 430f and 430b may comprise graphics. The graphics may extend substantially around the entire circumference of the absorbent article 100 and may be disposed across side seams 172 and/or across proximal front and back belt edges 15 (see FIG. 5); or, alternatively, adjacent to the seams in the manner described in U.S. Pat. No. 9,498,389 to create a more underwear-like article. The graphics may also be discontinuous.

Topsheets

The absorbent articles 100 of the present disclosure may comprise a topsheet 124. The topsheet 124 is the part of the absorbent article 100 that is in contact with the wearer's skin. The topsheet 124 may be joined to portions of the backsheet 125, the absorbent core 128, the leg cuffs 52, and/or any other layers as is known to those of ordinary skill in the art. The topsheet 124 may be compliant, soft-feeling, and non-irritating to the wearer's skin. Further, at least a portion of, or all of, the topsheet may be liquid permeable, permitting liquid bodily exudates to readily penetrate through its thickness. A suitable topsheet may be manufactured from a wide range of materials, such as porous foams, reticulated foams, apertured plastic films, woven materials, nonwoven materials, woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. The topsheet may have one or more layers. The topsheet may be apertured, may have any suitable three-dimensional features, and/or may have a plurality of embossments (e.g., a bond pattern). The topsheet may be apertured by overbonding a material and then rupturing the overbonds through ring rolling, such as disclosed in U.S. Pat. No. 5,628,097, to Benson et al., issued on May 13, 1997 and disclosed in U.S. Pat. Appl. Publication No. US 2016/0136014 to Arora et al. Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet.

Backsheets

The absorbent article 100 of the present disclosure may comprise a backsheet 125. The backsheet 125 is generally that portion of the absorbent article 100 positioned proximate to the garment-facing surface of the absorbent core 128. The backsheet 125 may be joined to portions of the topsheet 124, the backsheet nonwoven 127, the absorbent core 128, and/or any other layers of the absorbent article by any attachment methods known to those of skill in the art. The backsheet film 126 prevents, or at least inhibits, the bodily exudates absorbed and contained in the absorbent core 128 from soiling articles such as bedsheets, undergarments, and/or clothing. The backsheet is typically liquid impermeable, or at least substantially liquid impermeable. The backsheet may, for example, be or comprise a thin plastic film, such as a thermoplastic film having a thickness of about 0.012 mm to about 0.051 mm. Other suitable backsheet materials may include breathable materials which permit vapors to escape from the absorbent article, while still preventing, or at least inhibiting, bodily exudates from passing through the backsheet.

Leg Cuffs

The absorbent articles 100 of the present disclosure may comprise leg cuffs 52, which include inner leg cuffs 150 and outer leg cuffs 140. The inner leg cuffs 150 may be positioned laterally inboard of outer leg cuffs 140. Each of the leg cuffs 52 may be formed by a piece of material which is bonded to the absorbent article 100 so it can extend upwards from a wearer-facing surface of the absorbent article 100 and provide improved containment of body exudates approximately at the junction of the torso and legs of the wearer. The inner leg cuffs 150 are delimited by an edge joined directly or indirectly to (or formed by) the topsheet and/or the backsheet and a free terminal edge, which is intended to contact and form a seal with the wearer's skin. The inner leg cuffs 150 may extend longitudinally at least partially (or fully) between the front end edge 136 and the back end edge 138 of the absorbent article 100 on opposite sides of the chassis and may be at least present in the crotch region 37. The inner leg cuffs 150 may each comprise one or more elastics 316 (e.g., elastic strands or strips) near or at the free terminal edge. These elastics 316 cause the inner leg cuffs 150 to help form a seal around the legs and torso of a wearer. The outer leg cuffs 140 extend at least partially between the front end edge 136 and the back end edge 138. The outer leg cuffs 140 essentially cause portions of the absorbent article 100 proximate to the chassis side edges 237a and 237b to help form a seal around the legs of the wearer. The outer leg cuffs 140 may extend at least within the crotch region 37.

Waistbands/Waistcaps

The absorbent articles 100 of the present disclosure may comprise one or more elastic waistbands 122. The elastic waistbands 122 may be positioned on the garment-facing surface or the wearer-facing surface, or may be formed therebetween. As an example, a first elastic waistband 122 may be present in the front waist region 36 near the front waist edge 136 and a second elastic waistband 122 may be present in the back waist region 38 near the back waist edge 138. The elastic waistbands 122 may aid in sealing the absorbent article 100 around a waist of a wearer and at least inhibiting bodily exudates from escaping the absorbent article 100 through the waist opening circumference. In some instances, an elastic waistband may fully surround the waist opening 190 of the absorbent article 100. A waist cap 123 may be formed by an extension of the waistband 122 and may remain unattached to the underlying structure in the central portion of the waist cap 123 to allow bodily exudates that flow along the topsheet 124 to be trapped between the topsheet 124 and the underside of the waist cap 123. In other words, the waist cap 123 may be joined to the underlying structure, e.g., center chassis 200 of the absorbent article 100 along the longitudinally distal edge of the waist cap 123 and/or along the laterally opposing side edges of the waist cap 123.

Belts

Beyond what was disclosed about belts in the OPEN-FORM TAPED ARTICLE and CLOSED-FORM PANT ARTICLE Sections above, the front and back belts 430f and 430b may comprise front and back inner belt layers 432 and front and back outer belt layers 434 having an elastomeric material (e.g., a plurality of elastics 316 or a film (which may be apertured)) disposed at least partially therebetween. The plurality of elastics 316 or the film may be relaxed (including being cut) to reduce elastic strain over the absorbent core 128 or, may alternatively, run continuously across the absorbent core 128. The plurality of elastics 316 may have uniform or variable spacing therebetween in any portion of the belts. The plurality of elastics 316 may also be pre-strained the same amount or different amounts. The front and/or back belts 430f and 430b may have one or more elastics free zones where the chassis 200 overlaps the belts 430f and 430b. In other instances, at least some of the plurality of elastics 316 may extend continuously across the chassis 200.

The front and back inner belt layers 432 and the front and back outer belt layers 434 may be joined using adhesives, heat bonds, pressure bonds, ultrasonic, or thermoplastic bonds. Various suitable belt layer configurations can be found in U.S. Pat. Appl. Pub. No. 2013/0211363.

Front and back belt end edges 438*f* and 438*b* may extend longitudinally beyond the front and back chassis end edges 236 and 238 or they may be co-terminus. The front and back belt side edges 437 may extend laterally beyond the chassis side edges 237*a* and 237*b*. The front and back belts 430*f* and 430*b* may be continuous (i.e., having at least one layer that is continuous (see 434 in FIG. 7E) from belt end edge 438*f* to the opposite belt end edge 438*b*). Alternatively, the front and back belts 430*f* and 430*b* may be discontinuous from belt end edge 438*f* to the opposite belt end edge 438*b* (see 432 and 434 in FIG. 7D), such that they are discrete.

As disclosed in U.S. Pat. No. 7,901,393, the longitudinal length (along the central longitudinal axis 42) of the back belt 430*b* may be greater than the longitudinal length of the front belt 430*f*, and this may be particularly useful for increased buttocks coverage when the back belt 430*b* has a greater longitudinal length versus the front belt 430*f* adjacent to or immediately adjacent to the side seams 172. Alternatively, the bottom corners of the longer back belt may be trimmed in diagonal lines or curves.

The front and back belts 430*f* and 430*b* may include slits, holes, and/or perforations providing increased breathability, softness, and a garment-like texture. Underwear-like appearance can be enhanced by substantially aligning the waist and leg edges at the side seams 172.

Arrays

"Array" means a display of packages comprising disposable absorbent articles of different article constructions (e.g., different elastomeric materials [compositionally and/or structurally] in the side panels, side flaps and/or belts flaps, different graphic elements, different product structures, fasteners or lack thereof, sizes, core capacities, etc.). The packages may have the same brand and/or sub-brand and/or the same trademark registration and/or having been manufactured by or for a common manufacturer and the packages may be available at a common point of sale (e.g. oriented in proximity to each other in a given area of a retail store). An array is marketed as a line-up of products normally having like packaging elements (e.g., packaging material type, film, paper, dominant color, design theme, etc.) that convey to consumers that the different individual packages are part of a larger line-up. Arrays often have the same brand, for example, "Huggies," and same sub-brand, for example, "Pull-Ups." A different product in the array may have the same brand "Huggies" and the sub-brand "Little Movers." The differences between the "Pull-Ups" product of the array and the "Little Movers" product in the array may include product form, application style, different fastening designs or other structural elements intended to address the differences in physiological or psychological development. Furthermore, the packaging is distinctly different in that "Pull-Ups" is packaged in a predominately blue or pink film bag and "Little Movers" is packaged in a predominately red film bag.

Further regarding "Arrays," as another example an array may be formed by different products having different product forms manufactured by the same manufacturer, for example, "Kimberly-Clark", and bearing a common trademark registration for example, one product may have the brand name "Huggies," and sub-brand, for example, "Pull-Ups." A different product in the array may have a brand/sub-brand "Good Nites" and both are registered trademarks of The Kimberly-Clark Corporation and/or are manufactured by Kimberly-Clark. Arrays also often have the same trademarks, including trademarks of the brand, sub-brand, and/or features and/or benefits across the line-up. "On-line Array" means an "Array" distributed by a common on-line source.

Transverse Barrier

Figure 13:
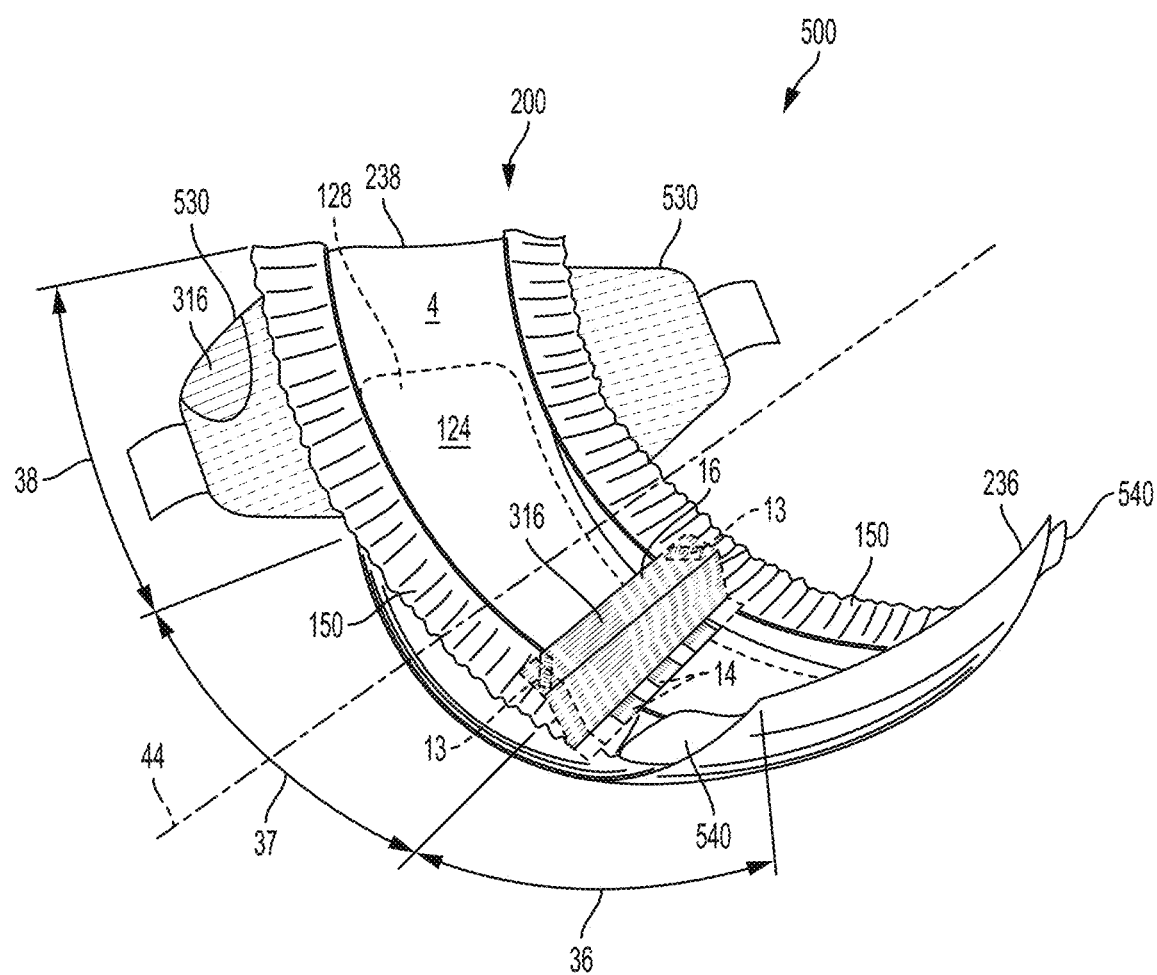
FIG. 13 is a perspective interior top view of a taped article comprising a transverse barrier.

As shown in FIG. 13, the transverse barrier 16 may extend parallel with the lateral axis 44 and may be joined via bonds 13 to the cuffs 150 and joined by bonds 14 to the topsheet 124 such that the transverse barrier extends in a Z direction away from the topsheet when the article (e.g., 500) is opened and worn. More particularly, the transverse barrier 16 may extend in a Z direction due in part to the cuffs standing upward in the Z direction as the article is opened for wear. The transverse barrier 16 may prevent fecal matter from migrating into the front waist region 36. Thus, the transverse barrier 16 may be oriented proximate to where the front waist region 36 and crotch region 37 meet, or may be disposed between the juncture of where the front waist region 36 and the crotch region 37 meet and the lateral axis 44. Offsetting the bond locations 13 and 14 will influence the angle of the transverse barrier 16 relative to the topsheet 124. The bond locations 13 and 14 may be oriented such that the transvers barrier extends in a Z direction that is approximately 90 degrees from the surface of the topsheet 124.

Feminine Hygiene Article

Referring to FIGS. 11-12C, absorbent articles of the present disclosure may be a feminine hygiene article 801 also referred to as a sanitary napkin, and includes feminine pads, and liners. The sanitary napkin 801 may comprise a liquid permeable topsheet 124, a liquid impermeable, or substantially liquid impermeable, backsheet 125 and an absorbent core 128. The liquid impermeable backsheet 125 may or may not be vapor permeable. The absorbent core 128 may have any or all of the features described herein with respect to the absorbent core 128 and, in some forms, may have a secondary topsheet 124' (STS) instead of the acquisition materials disclosed above. The STS 124' may comprise one or more channels, as described above (including the embossed version). In some forms, channels in the STS 124' may be aligned with channels in the absorbent core 128. The sanitary napkin 801 may also comprise wings 120 extending outwardly with respect to a longitudinal axis 42 of the sanitary napkin 801. The sanitary napkin 801 may also comprise a lateral axis 44. The wings 120 may be integral to TS, BS joined to the topsheet 124, the backsheet 125, and/or the absorbent core 128.

Process

Figure 14:
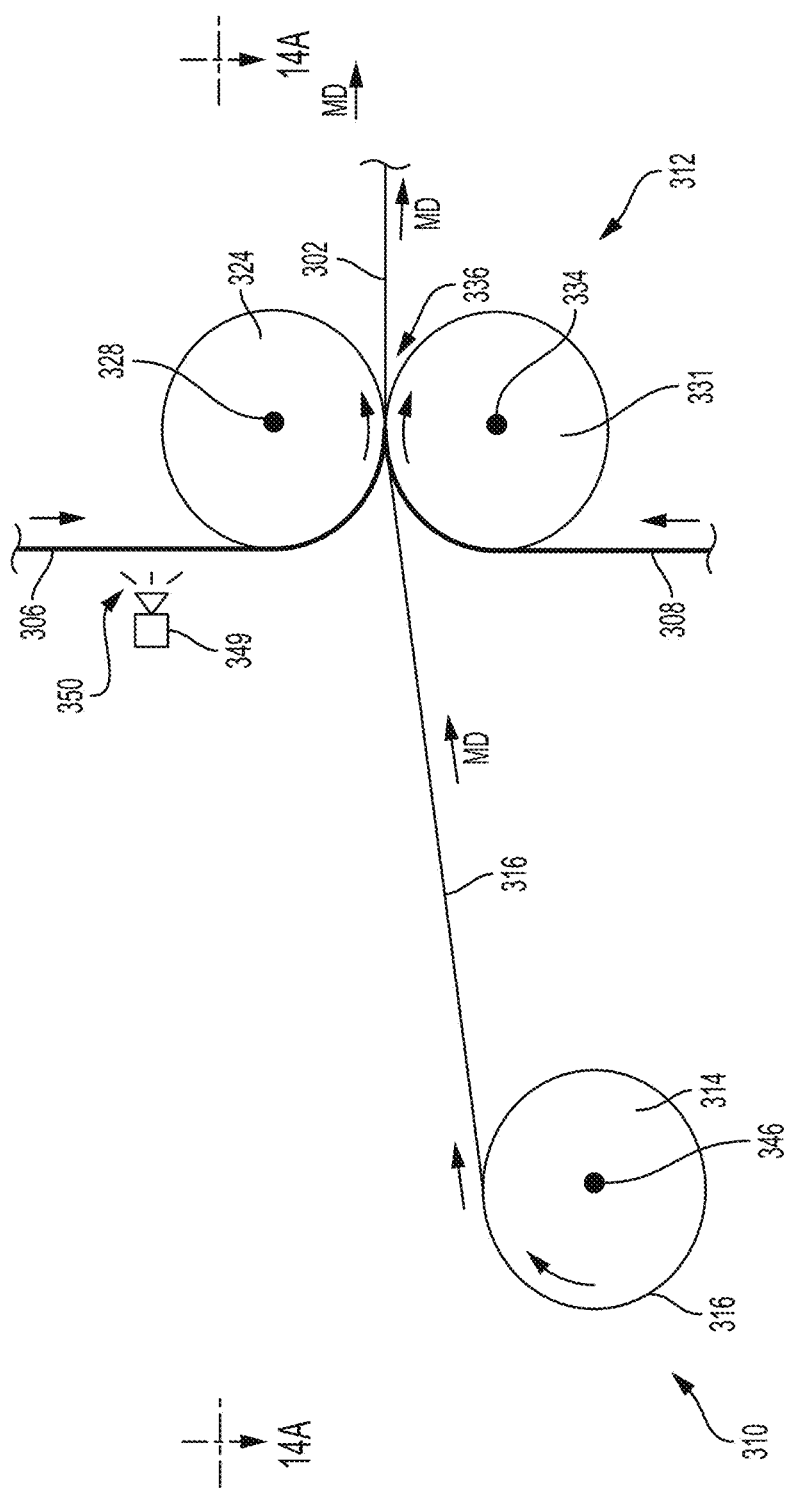
FIG. 14 is a schematic side view of a converting apparatus adapted to manufacture an elastomeric laminate including a first plurality of elastics positioned between a first substrate and a second substrate.

Referring to FIGS. 14 and 14A, a plurality of elastics 316 (from about 10 strands to about 1500 strands having a decitex from about 10 to about 500) unwind about a first axis of rotation 346 from a first beam 314 (which is a first metering device 310) in the machine direction MD and transfer the plurality of elastic strands 316 from the first beam 314 (e.g., a warp beam) to a second metering device 312 (which includes a first roller 324 having a second axis of rotation 328 and a second roller 331 having a third axis of rotation 334, which form a nip 336). The plurality of elastic strands 316 may be stretched along the machine direction MD between the first metering device 310 and the second metering device 312 to prestrain the plurality of elastics 316 (from about 50% to about 400%). The stretched elastic strands 316 may be joined via an adhesive 350 from an adhesive applicator 349 (or the plurality of elastics 316 may be joined via other suitable means) with a first substrate layer 306 and a second substrate layer 308 at the second metering device 312 to produce an elastomeric laminate 302, such that each of the strands are spaced (in the CD) in the elastomeric laminate from about 0.25 mm to about 4 mm. It is this process that forms the elastomeric laminate 302 of the present disclosure and that may be further incorporated into the various absorbent article components such as the belts, ear panels, side panels, transverse barriers, topsheets, backsheets, cuffs, waistbands, waistcaps, and/or chassis to offer the benefits described in this patent application. Further details of the process of creating beamed elastomeric laminate(s) for use in disposable absorbent articles are disclosed in U.S. Ser. No. 62/436,589, titled "METHODS AND APPARATUSES FOR MAKING ELASTOMERIC LAMINATES WITH ELASTIC STRANDS UNWOUND FROM BEAMS," first-named inventor being Schneider, filed on Dec. 20, 2016. The elastomeric laminate 302 may be produced as part of the absorbent article manufacturing line, or may be produced offline, and unwound as an elastomeric laminate that is fed into the absorbent article manufacturing line.

Elastomeric Laminate(s) of the Present Disclosure

An "elastomeric laminate 302" of the present disclosure may comprise a plurality of elastics 316 between a first substrate 306 and a second substrate layer 308, where the plurality of elastics 316 (often referred to as a "first plurality of elastics," a "second plurality of elastics," etc.) has an Average-Strand-Spacing from about 0.25 mm to about 4 mm, an Average-Dtex from about 10 to about 500, and an Pressure-Under-Strand from about 0.1 to about 1 psi. Said elastomeric laminate 302 may be used to form at least a portion of various absorbent article components. When the elastomeric laminate 302 forms at least a portion of at least one of the group consisting of a belt, a chassis, a side panel, a topsheet, a backsheet, and an ear panel, and combinations thereof, the plurality of elastics 316 of the elastomeric laminate 302 may comprise from about 40 to about 1000 elastic strands. And, when the elastomeric laminate 302 forms at least a portion of at least one of the group consisting of a waistband, a waistcap, an inner leg cuff, an outer leg cuff, and a transverse barrier, and combinations thereof, the first plurality of elastics 316 of the elastomeric laminate 302 may comprise from about 10 to about 400 elastic strands. Ultimately, "plurality of elastics" is a term of context, where certain properties (e.g., Average-Dtex, Average-Strand-Spacing, Pressure-Under-Strand, etc.), arrangements, attributes, characteristics, disposition, etc. of the elastics are referenced to define what a certain "plurality of elastics" is.

Further, the elastomeric laminate 302 may form at least a portion of one or more of the group of article components including a belt 430, a side panel 330, chassis 200, a topsheet 124, backsheet 125, and an ear panel 530, the elastomeric laminate 302 may comprise a plurality of elastics having from about 40 to about 1000 elastic strands with an Average-Strand-Spacing from about 0.25 mm to about 4 mm, a Average-Dtex from about 10 to about 500, an Average-Pre-Strain from about 50% to about 400%; and a first substrate 306 and a second substrate 308 each having a basis weight from about 6 grams per square meter to about 30 grams per square meter.

When the elastomeric laminate 302 may form at least a portion of one or more of the group of article components including a belt 430, a side panel 330, chassis 200, a topsheet 124, backsheet 125, and an ear panel 530, the elastomeric laminate 302 may comprise a plurality of elastics having from about 50 to about 825 elastic strands. Further, the plurality of elastics may comprise from about 100 to about 650 elastic strands. Still further, the plurality of elastics may comprise from about 150 to about 475 elastic strands.

When the elastomeric laminate 302 may form at least a portion of one or more of the group of article components including a belt 430, a side panel 330, chassis 200, a topsheet 124, backsheet 125, and an ear panel 530, the elastomeric laminate 302 may comprise a plurality of elastics having an Average-Strand-Spacing from about 0.5 mm to about 3.5 mm. Further, the plurality of elastics may have an Average-Strand-Spacing from about 0.75 mm to about 2.5 mm.

When the elastomeric laminate 302 may form at least a portion of one or more of the group of article components including a belt 430, a side panel 330, chassis 200, a topsheet 124, backsheet 125, and an ear panel 530, the elastomeric laminate 302 may comprise a plurality of elastics having an Average-Dtex from about 30 to about 400. Further, the elastomeric laminate 302 may have an Average-Dtex of the plurality of elastics from about 50 to about 250.

When the elastomeric laminate 302 may form at least a portion of one or more of the group of article components including a belt 430, a side panel 330, chassis 200, a topsheet 124, backsheet 125, and an ear panel 530, the elastomeric laminate 302 may comprise a plurality of elastics having an Average-Pre-Strain which may be from about 75% to about 300%. Further, the elastomeric laminate may comprise a plurality of elastics 316 with an Average-Pre-Strain of from about 100% to about 250%

The elastomeric laminate 302 may form at least a portion of one or more of the group of article components including a waistband 122, waistcap 123, inner leg cuff 150, outer leg cuff 140 and a transverse barrier 16, and may comprise a plurality of elastics having from about 10 to about 400 elastic strands with an Average-Strand-Spacing from about 0.25 mm to about 4 mm, a decitex from about 10 to about 500, an Average-Pre-Strain from about 50% to about 400% and a first substrate 306 and/or second substrate 308 each having a basis weight from about 6 grams per square meter to about 30 grams per square meter.

The elastomeric laminate 302 may form at least a portion of one or more of the group of article components including a waistband 122, waistcap 123, inner leg cuff 150, outer leg cuff 140 and a transverse barrier 16, and may comprise a plurality of elastics having from about 15 to about 300 elastic strands. Further, the plurality of elastics may comprise from about 20 to about 225 elastic strands. Further, the plurality of elastics may comprise from about 25 to about 150 elastic strands.

The elastomeric laminate 302 may form at least a portion of one or more of the group of article components including a waistband 122, waistcap 123, inner leg cuff 150, outer leg cuff 140 and a transverse barrier 16, and may comprise a plurality of elastics having an Average-Strand-Spacing from about 0.5 mm to about 3.0 mm. Further, the plurality of elastics 316 may have an Average-Strand-Spacing from about 0.75 mm to about 2.5 mm.

The elastomeric laminate 302 may form at least a portion of one or more of the group of article components including a waistband 122, waistcap 123, inner leg cuff 150, outer leg cuff 140 and a transverse barrier 16, and may comprise a plurality of elastics having an Average-Dtex from about 30 to about 400. Alternatively, the plurality of elastics 316 of the elastomeric laminate 302 may have an Average-Dtex from about 50 to about 250.

The elastomeric laminate 302 may form at least a portion of one or more of the group of article components including a waistband 122, waistcap 123, inner leg cuff 150, outer leg cuff 140 and a transverse barrier 16, and may comprise a plurality of elastics having an Average-Pre-Strain from about 75% to about 300%. Alternatively, the elastomeric laminate may comprise a plurality of elastics with an Average-Pre-Strain of from about 100% to about 250%.

Any one of the belt 430, side panel 330, ear panel 530, chassis 200, topsheet 124, backsheet 125, waistband 122, waistcap 123, inner leg cuff 150, outer leg cuff 140 or transverse barrier may comprise an elastomeric laminate 302 comprising a plurality of elastics 316 having an Pressure-Under-Strand from about 0.1 psi to about 1 psi, or from about 0.2 psi to about 0.8 psi.

An absorbent article of the present disclosure may have an elastomeric laminate 302 forming a portion of one or more of a belt 430, side panel 330, ear panel 530, waistband 122, chassis 200, topsheet 124 and backsheet 125. The elastomeric laminate 302 may comprise a plurality of elastics having a specific elastic decitex, nonwoven type, nonwoven basis weight, elastic spacing and elastic strain. And, the article may comprise two or more absorbent article components (including a belt 430, side panel 330, ear panel 530, waistband 122, chassis 200, topsheet 124 and backsheet 125) comprising an elastomeric laminate 302 having one or more identical or substantially identical elastomeric laminate elements (including elastic decitex, nonwoven type, nonwoven basis weight, elastic spacing and elastic strain).

Beyond the beamed elastic strands 316 that may be used in each of the absorbent article components, other elastic components such as elastic nonwovens, elastomeric films, elastomeric foams, elastomeric scrims, and elastomeric ribbons, or combinations thereof, may be used with the beamed elastics 316.

The elastomeric laminate 302 may comprise a plurality of elastics 316 that may be the same color as one or both of the first substrate layer 306 and second substrate layer 308 so the elastic material may be more hidden, i.e. masked or may be of a different color so the elastic material is visible in the elastomeric laminate 302. Furthermore, the plurality of elastic 316 may be transparent or translucent such that it is virtually invisible. Transparency or translucency combined with the very low decitex of the elastic 316 may render the elastic 316 visibly and tactilely unnoticeable by users of absorbent articles comprising elastomeric laminate 302 comprising such elastics 316.

In one embodiment, an absorbent article 100 may comprise a chassis 200 having a topsheet 124, a backsheet 125 and an absorbent core 128 disposed between the topsheet 124 and the backsheet 125. The absorbent article 100 may also comprise a back belt 430B joined to the back waist region 38 of the chassis 200 and extending outboard of the back waist region 38 of the chassis 200. The article also comprising a front belt 430F joined to the front waist region 36 of the chassis 200 and extending outboard of the front waist region 36 of the chassis 200. The front belt 430F may be joined to the back belt 430B at or adjacent the laterally opposing belt side edges 437 to form leg openings 192 and a waist 190 opening to form a closed-form pant 400. The back belt 430B having a first plurality of elastics 316a comprising greater than about 40 elastic strands and the front belt 430F having a second plurality of elastics 316b comprising greater than about 40 elastics strands. The first plurality of elastics 316a having an Average-Strand-Spacing of less than about 4 mm. The second plurality of elastics 316b having an Average-Strand-Spacing of less than about 4 mm. One or both of the first plurality of elastics 316a and second plurality of elastics 316b having a portion that overlaps with the absorbent core 128. The absorbent article 100 having a Product Hip-to-Waist Silhouette from about 0.8 to about 1.1, alternatively from about 0.9 to about 1.0. The absorbent article 100 may have a Product Waist-to-Crotch Silhouette is from about 0.8 to about 2.0, alternatively from about 0.9 to about 1.5, in another embodiment the Product Waist-to-Crotch Silhouette may be from about 1.2 to about 1.35. The absorbent article may also have a Relaxed Product Waist Width from about 80 mm to about 270 mm, alternatively from about 170 mm to about 270 mm and in other embodiments from about 80 mm to about 180 mm. The absorbent article may also have a Relaxed Product Hip Width from about 80 mm to about 300 mm, alternatively from about 80 mm to about 200 mm. The absorbent article may also have a Relaxed Product length from about 200 mm to about 300 mm. The back belt 430B may be divided into 4 equal sections, the first section, Section 1, including the distal most elastic, the fourth section, Section 4, including the proximal most elastic, the second section, Section 2, is disposed adjacent the first section and the third section, Section 3, is disposed between the second section and the fourth section, Section 4. The front belt 430F may also be divided into 4 equal sections, the first section, Section 1, including the distal most elastic, the fourth section, Section 4, including the proximal most elastic, the second section, Section 2, is disposed adjacent the first section and the third section, Section 3, is disposed between the second section and the fourth section, Section 4. One or more of the sections forming the front belt 430F may have a different Section-Modulus from the remaining sections of the front belt 430F. One or more of the sections forming the back belt 430B may have a different Section-Modulus from the remaining sections of the front belt 430B. Alternatively, one or more of the sections forming the front belt 430F may have a different Section-Modulus from one or more of the sections forming the back belt 430B. The back belt 430B and front belt 430F may both be formed at least in part by an elastomeric laminate 302 comprising a first substrate layer 306 and a second substrate layer 308 and a plurality of elastics disposed between the first and second substrate layers 306 and 308. One or both of the first and second substrate 306 and 308 forming at least a portion of the back belt 430B and one or both of the first and second substrate 306 and 308 forming at least a portion of the front belt 43F are separate and spaced apart from each other. Alternatively, one or both of the first and second substrate 306 and 308 forming at least a portion of the back belt 430B and one or both of the first and second substrate 306 and 308 forming at least a portion of the front belt 43F are continuous and extends from the first waist edge to the longitudinally opposing second waist edge. The elastomeric laminate may also comprise an adhesive joining the first substrate layer 306 and/or second substrate layer 308 to the plurality of elastics 316. The adhesive may be selected from the group consisting of Styrenic block copolymers, Polyolefins, Ethylene-vinyl Acetates, Polyurethanes, Ethylene-propylene copolymers, Propylene-ethylene copolymers, Polyolefin block polymers, Polyolefin homopolymers, Polyesters, Polyamides, Silicones, Cyanoacrylics, Acrylics, butyl rubber, and combinations thereof. In certain embodiments, one of the sections in the front belt 430F may comprise more elastics that one or more of the remaining sections of the front belt 430F and one of the sections in the back belt 430B may comprise more elastics that one or more of the remaining sections of the back belt 430B. The front belt 430F may have at least one section that comprises greater than 10 elastics and the back belt 430B may have at least two sections that comprise greater than 10 elastics. The front belt 430F may have at least two sections having an Average-Strand-Spacing of less than about 3 mm and the back belt 430B may have at least three sections having an Average-Strand-Spacing of less than about 3 mm.

In another embodiment, an absorbent article 100 may comprise a chassis 200 having a topsheet 124, a backsheet 125 and an absorbent core 128 disposed between the topsheet 124 and the backsheet 125. The absorbent article 100 may also comprise a back belt 430B joined to the back waist region 38 of the chassis 200 and extending outboard of the back waist region 38 of the chassis 200. The article also comprising a front belt 430F joined to the front waist region 36 of the chassis 200 and extending outboard of the front waist region 36 of the chassis 200. The front belt 430F may be joined to the back belt 430B at or adjacent the laterally opposing belt side edges 437 to form leg openings 192 and a waist 190 opening to form a closed-form pant 400. The back belt 430B having a first plurality of elastics 316a comprising greater than about 40 elastic strands and the front belt 430F having a second plurality of elastics 316b comprising greater than about 40 elastics strands. The first plurality of elastics 316a having an Average-Strand-Spacing of less than about 4 mm. The second plurality of elastics 316b having an Average-Strand-Spacing of less than about 4 mm. One or both of the first plurality of elastics 316a and second plurality of elastics 316b having a portion that overlaps with the absorbent core 128. The absorbent article 100 having a Product Hip-to-Waist Silhouette from about 0.8 to about 1.1, alternatively from about 0.9 to about 1.1. The absorbent article 100 may have a Product Waist-to-Crotch Silhouette is from about 0.8 to about 2.8, alternatively from about 0.8 to about 2.5, in another embodiment the Product Waist-to-Crotch Silhouette may be from about 0.8 to about 2.0. The absorbent article may also have a Relaxed Product Waist Width from about 200 mm to about 400 mm alternatively from about 225 mm to about 375 mm and in other embodiments from about 250 mm to about 350 mm. The absorbent article may also have a Relaxed Product Hip Width from about 200 mm to about 450 mm, alternatively from about 225 mm to about 425 mm, in other embodiments the Relaxed Product Hip Width may be from about 250 mm to about 400 mm. The absorbent article may also have a Relaxed Product length from about 250 mm to about 450 mm, alternatively from about 275 to about 425, in yet another embodiment the Relaxed Product Length may be from about 300 mm to about 400 mm. The back belt 430B may be divided into 4 equal sections, the first section, Section 1, including the distal most elastic, the fourth section, Section 4, including the proximal most elastic, the second section, Section 2, is disposed adjacent the first section and the third section, Section 3, is disposed between the second section and the fourth section, Section 4. The front belt 430F may also be divided into 4 equal sections, the first section, Section 1, including the distal most elastic, the fourth section, Section 4, including the proximal most elastic, the second section, Section 2, is disposed adjacent the first section and the third section, Section 3, is disposed between the second section and the fourth section, Section 4. One or more of the sections forming the front belt 430F may have a different Section-Modulus from the remaining sections of the front belt 430F. One or more of the sections forming the back belt 430B may have a different Section-Modulus from the remaining sections of the front belt 430B. Alternatively, one or more of the sections forming the front belt 430F may have a different Section-Modulus from one or more of the sections forming the back belt 430B. The back belt 430B and front belt 430F may both be formed at least in part by an elastomeric laminate 302 comprising a first substrate layer 306 and a second substrate layer 308 and a plurality of elastics disposed between the first and second substrate layers 306 and 308. One or both of the first and second substrate 306 and 308 forming at least a portion of the back belt 430B and one or both of the first and second substrate 306 and 308 forming at least a portion of the front belt 43F are separate and spaced apart from each other. Alternatively, one or both of the first and second substrate 306 and 308 forming at least a portion of the back belt 430B and one or both of the first and second substrate 306 and 308 forming at least a portion of the front belt 43F are continuous and extends from the first waist edge to the longitudinally opposing second waist edge. The elastomeric laminate may also comprise an adhesive joining the first substrate layer 306 and/or second substrate layer 308 to the plurality of elastics 316. The adhesive may be selected from the group consisting of Styrenic block copolymers, Polyolefins, Ethylene-vinyl Acetates, Polyurethanes, Ethylene-propylene copolymers, Propylene-ethylene copolymers, Polyolefin block polymers, Polyolefin homo-polymers, Polyesters, Polyamides, Silicones, Cyanoacrylics, Acrylics, butyl rubber, and combinations thereof. In certain embodiments, one of the sections in the front belt 430F may comprise more elastics that one or more of the remaining sections of the front belt 430F and one of the sections in the back belt 430B may comprise more elastics that one or more of the remaining sections of the back belt 430B. The front belt 430F may have at least one section that comprises greater than 20 elastics, alternatively greater than 40 elastics and the back belt 430B may have at least two sections that comprise greater than 20 elastics, alternatively greater than 40 elastics. The front belt 430F may have at least two sections having an Average-Strand-Spacing of less than about 3 mm and the back belt 430B may have at least three sections having an Average-Strand-Spacing of less than about 3 mm.

Multiple Beams

It should be appreciated that one or more of a waistband 122, waistcap 123, inner leg cuff 150, outer leg cuff 140 and/or a transverse barrier may be formed from multiple beams of elastic. For example, one beam may form a first portion of one or more of a waistband 122, waistcap 123, inner leg cuff 150, outer leg cuff 140 and/or a transverse barrier and a second beam may form a second portion of one or more of a waistband 122, waistcap 123, inner leg cuff 150, outer leg cuff 140 and/or a transverse barrier, where the separate beams may comprise a different number of elastics, and/or the beams may have elastics having different decitex, and/or the elastics of the two beams may be disposed at different spacing, and/or the separate beams may deliver elastics having different pre-strain, and/or the different beams may deliver elastics having different orientations in the product, e.g. liner, arcuate, angled, etc. The resultant portions of the waistband 122, waistcap 123, inner leg cuff 150, outer leg cuff 140 and/or transverse barrier created from such a multi-beam approach may have different texture, garment-like appearance, modulus and/or different force.

It is also to be appreciated that one or more of the absorbent article components including a belt 430, side panel 330, ear panel 530, waistband 122, chassis 200, topsheet 124 and backsheet 125, may comprise an elastomeric laminate 302 formed from multiple beams of elastic. For example, one beam may form a first portion of one or more absorbent article components including a belt 430, side panel 330, ear panel 530, waistband 122, chassis 200, topsheet 124 and backsheet 125, and a second beam may form a second portion of an absorbent article component including a belt 430, side panel 330, ear panel 530, waistband 122, chassis 200, topsheet 124 and backsheet 125. The separate beams may comprise a different number of elastics and the beams may have a plurality of elastics 316 having different decitex. The elastics of the two beams may be disposed at different spacing and/or the separate beams may deliver elastics having different pre-strain and/or the different beams may deliver elastics having different orientations in the product, e.g. liner, arcuate, angled, etc. The resultant portions of the absorbent article components including a belt 430, side panel 330, ear panel 530, waistband 122, chassis 200, topsheet 124 and/or backsheet 125 created from such a multi-beam approach may have different texture, garment-like appearance, modulus and/or different force.

Laterally Extending Elastics

A wearable article of the present disclosure may comprise one or more elastomeric laminates 302 having a plurality of laterally extending elastics, where the one or more elastomeric laminates may be present in a first waist region, the crotch region and/or in the opposing second waist region, and where the plurality of elastics 316 may be disposed in one or both of the first and second waist regions may have one or more of a higher elastic decitex, higher percent strain, and smaller Average-Strand-Spacing than some or all of the laterally extending a plurality of elastics disposed in the crotch region. Such a wearable article may comprise one or more elastomeric laminates 302 having a plurality of elastics 316 having from about 100 to about 1500 elastic strands with an Average-Strand-Spacing from about 0.25 mm to about 4 mm, a decitex from about 10 to about 500, an elastic Average-Pre-Strain from about 50% to about 400%, and a first substrate 306 and/or second substrate 308 each having a basis weight from about 6 grams per square meter to about 30 grams per square meter.

Chemistry (Spandex Vs. Extruded Strands) and Structure

Beamed elastic uses Spandex fibers. One type of Spandex fiber is "PolyUrethane Urea" elastomer or the "high hard segment level PolyUrethane" elastomer, which must be formed into fibers using a solution (solvent) spinning process (as opposed to being processable in the molten state.) The Urea linkages in PolyUrethane Urea provides strong mutual chemical interactions crucial for providing "anchoring" that enables good stress relaxation performance at temperatures near body temperature on timescales corresponding to diaper wear, including overnight. This type of anchoring enables better force relaxation (i.e. little force decay with time when held in stretched condition at body temperature) over many thermoplastic polyurethane (PolyUrethane with hard segment melting below 200 deg. C.) or thermoplastic Styrenic block copolymers.

Figure 23:
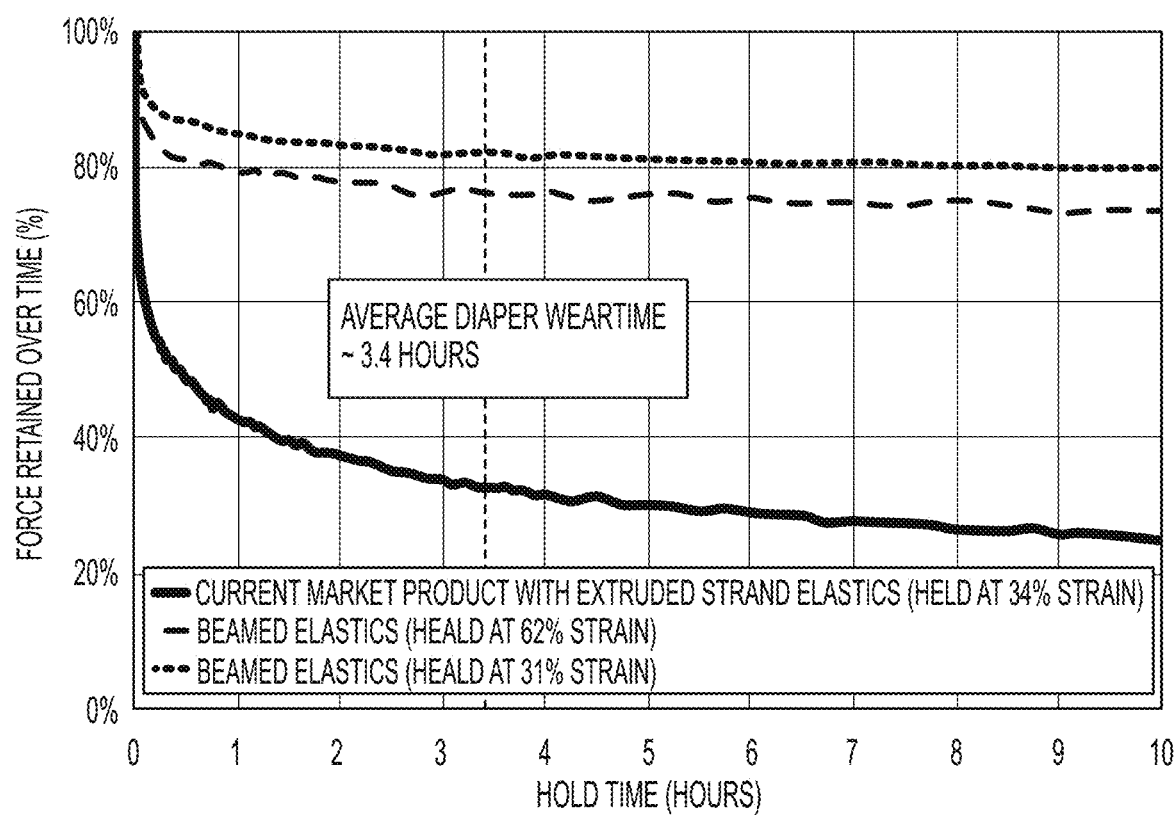
FIG. 23 is a chart showing force relaxation over time for various elastomeric laminates.

In contrast, extruded strands and scrims are typically made of Styrenic block copolymers or thermoplastic elastomers that can be formed in the molten state by conventional extrusion processes. Thermoplastic elastomers include compositions like polyolefin, polyurethane (PolyUrethane with hard segment melting below 200 deg. C.) elastomers, etc. Because these thermoplastic elastomers like Polyurethane (PolyUrethane with hard segment melting below 200 deg. C.) can be melted/remelted, and extruded it makes them susceptible to higher stress relaxation in use, which is a major negative. The styrenic block copolymers used in extruded strands comprise a comparatively long rubbery midblock situated between comparatively short end blocks. End blocks sufficiently short to enable good flow conventional extrusion processes often have a greater propensity to stress relax and undergo force relaxation over time see FIG. 23.

The Urea linkage present in Spandex requires it to be made by spinning process. Spandex can't be melted/remelted or extruded like Styrenic block copolymers. Spandex pre-polymer is combined with solvent and additives, and the solution is spun to make solid spandex fiber. Multiple fibers are then formed together to make one spandex strand. The Spandex strands may have surface finish to avoid blocking and wound onto spools. The one spandex fiber may have a decitex of about 15, so a 500 decitex strand may have nominally 33 fibers wound together to make one strand. Depending on the decitex we use for beam approach, we may have 15 fibers (or filaments), 8 fibers, 5 fibers, 3 fibers or even as low as 2 fibers. Spandex fiber can be mono-component or bi-component (as disclosed in WO201045637A2).

Further related to the chemistry of beamed elastics, it may be desirable to coat the beamed elastics with an oil, such as a silicone oil, including about 10%, about 7%, about 5%, about 3%, or about 1% silicone oil. Treating the beamed elastics with silicone oil helps to prevent blocking (cross-linking) when the strands are wound to a spool or a beam and it also lowers the COF for the strand in textile machinery (for weaving, knitting and warping processes).

Commercially available Spandex strands may also be known as Lycra, Creora, Roica, or Dorlastan. Spandex is often referred as Elastan fiber or Polyurethane fiber.

LYCRA HYFIT strands, a product of Invista, Wichita, Kans., are a suitable for making the strands that make up the plurality of elastics 316 that make up the elastomeric laminate 302. Some strands, for example, the aforementioned LYCRA HYFIT, may comprise a number of individual fibers wound together to form the strand. With regard to elastic strands formed of a number of individual fibers it has been discovered that the individual fibers can move relative to each other changing the cross sectional shape of the strand as well as becoming unraveled which can lead to poor control of the strands as well as poor bonding/adhering/joining of the elastic strands to one or both of the first substrate layer 306 and second substrate layer 308 of the elastomeric laminate 302. In order to minimize the negatives with regard to strands comprising a plurality of fibers it would be advantageous to minimize the number of fibers in a given strand. It would therefore be desirable to have less than about 40 fibers per strand, less than about 30 fibers per strand, less than about 20 fibers per strand, less than about 10 fibers per strand, less than about 5 fibers per strand and 1 fiber forming the strand. In the case of a single fiber forming the strand which can deliver comparable performance to the multi-fiber strands of the prior art it would be desirable for the fiber to have a fiber decitex from about 22 to about 300 and a fiber diameter from about 50 micrometers to about 185 micrometers.

Beamed Elastomeric Laminate Examples

Consumer interactions and research has shown that a longstanding unmet consumer need exists to provide absorbent articles which have the right balance of modulus for application and removal ease and freedom of movement while providing an article with low elastic pressure (relative to today's stranded products) to provide a comfortable wearing experience free from skin marks. It has been found that elastomeric laminate structures having a modulus of from about 2 gf/mm to about 15 gf/mm, alternatively from about 3 gf/mm to about 12 gf/mm, in other alternative embodiments from about 4 gf/mm to about 10 gf/mm are desirable for ease of application, ease of removal, conforming fit and freedom of movement. Depending on the elastic configuration in these structures they may exhibit very high Pressure-Under-Strand, e.g., elastic strands, leading to increased skin marking and reduced comfort. One approach to reduce the pressure of the elastic on the skin is to increase the number of elastics for a given area. Increasing the number of elastics within a given area alone may reduce the Pressure-Under-Strand, however, if that is the only change it can also significantly increase the overall modulus of the elastomeric laminate structure. In order to achieve the right balance of modulus and pressure on the skin it is necessary to reduce the elastic decitex and/or the elastic strain as the spacing between the elastics is reduced thereby increasing the elastic number in order to balance the modulus and pressure on the skin and maintain these parameters within the consumer preferred range. This breakthrough has been enabled through delivery of very low decitex elastic at very low strain levels and with very tight elastic spacing that have never before been seen in disposable absorbent articles. Delivery of such low decitex elastic at low strain and tight spacing is enabled via a new to absorbent article technology created from the textile warp beam technology approach. The examples below are some embodiments of such elastomeric structures.

TABLE 1

Inventive Belt Elastic Profiles

| Section | Number of Elastics | Average-Dtex | Average-Pre-Strain | Average-Strand-Spacing (mm) | Open Area (%) | Section-Modulus (gf/mm) | Pressure-Under-Strand (psi) |
|---|---|---|---|---|---|---|---|
| A |
| Front Belt |
| 1 | 40 | 140 | 100% | 0.6 | 79.2% | 10.9 | 0.328 |
| 2 | 40 | 70 | 150% | 0.6 | 85.3% | 5.5 | 0.463 |
| 3 | 40 | 70 | 150% | 0.6 | 85.3% | 5.5 | 0.463 |
| 4 | 40 | 140 | 100% | 0.6 | 79.2% | 10.9 | 0.328 |
| Back Belt |
| 4 | 40 | 140 | 100% | 0.6 | 79.2% | 10.9 | 0.328 |
| 3 | 40 | 70 | 150% | 0.6 | 85.3% | 5.5 | 0.463 |
| 2 | 40 | 70 | 150% | 0.6 | 85.3% | 5.5 | 0.463 |
| 1 | 40 | 140 | 100% | 0.6 | 79.2% | 10.9 | 0.328 |
| B |
| Front Belt |
| 1 | 50 | 70 | 175% | 0.5 | 82.4% | 6.6 | 0.386 |
| 2 | 50 | 70 | 175% | 0.5 | 82.4% | 6.6 | 0.386 |
| 3 | 50 | 70 | 175% | 0.5 | 82.4% | 6.6 | 0.386 |
| 4 | 50 | 70 | 175% | 0.5 | 82.4% | 6.6 | 0.386 |
| Back Belt |
| 4 | 50 | 70 | 175% | 0.5 | 82.4% | 6.6 | 0.386 |
| 3 | 50 | 70 | 175% | 0.5 | 82.4% | 6.6 | 0.386 |
| 2 | 50 | 70 | 175% | 0.5 | 82.4% | 6.6 | 0.386 |
| 1 | 50 | 70 | 175% | 0.5 | 82.4% | 6.6 | 0.386 |
| C |
| Front Belt |
| 1 | 30 | 70 | 200% | 0.8 | 89.0% | 4.1 | 0.618 |
| 2 | 20 | 210 | 150% | 1.1 | 86.1% | 8.9 | 0.490 |
| 3 | 30 | 70 | 200% | 0.8 | 89.0% | 4.1 | 0.618 |
| 4 | 30 | 70 | 200% | 0.8 | 89.0% | 4.1 | 0.618 |
| Back Belt |
| 4 | 30 | 70 | 200% | 0.8 | 89.0% | 4.1 | 0.618 |
| 3 | 30 | 70 | 200% | 0.8 | 89.0% | 4.1 | 0.618 |
| 2 | 30 | 70 | 200% | 0.8 | 89.0% | 4.1 | 0.618 |
| 1 | 30 | 210 | 150% | 1.1 | 86.1% | 8.9 | 0.490 |

TABLE 2

Inventive Ear/Side Panel Elastic Profiles

| Section | Number of Elastics | Average-Dtex | Average-Pre-Strain | Average-Strand-Spacing (mm) | Open Area (%) | Section-Modulus (gf/mm) | Pressure-Under-Strand (psi) |
|---|---|---|---|---|---|---|---|
| A |
| 1 | 30 | 140 | 125% | 1.0 | 87.5% | 6.6 | 0.546 |
| 2 | 30 | 140 | 125% | 0.8 | 84.4% | 8.2 | 0.437 |
| 3 | 30 | 140 | 125% | 1.0 | 87.5% | 6.6 | 0.546 |
| 4 | 30 | 140 | 125% | 1.0 | 87.5% | 6.6 | 0.546 |
| B |
| 1 | 60 | 70 | 125% | 0.5 | 82.4% | 6.6 | 0.386 |
| 2 | 60 | 70 | 125% | 0.5 | 82.4% | 6.6 | 0.386 |

TABLE 2-continued

Inventive Ear/Side Panel Elastic Profiles

| Section | Number of Elastics | Average-Dtex | Average-Pre-Strain | Average-Strand-Spacing (mm) | Open Area (%) | Section-Modulus (gf/mm) | Pressure-Under-Strand (psi) |
|---|---|---|---|---|---|---|---|
| 3 | 60 | 70 | 125% | 0.5 | 82.4% | 6.6 | 0.386 |
| 4 | 60 | 70 | 125% | 0.5 | 82.4% | 6.6 | 0.386 |
| C |  |  |  |  |  |  |  |
| 1 | 15 | 210 | 165% | 2.0 | 92.4% | 4.9 | 0.892 |
| 2 | 15 | 210 | 165% | 1.1 | 86.1% | 8.9 | 0.490 |
| 3 | 15 | 210 | 165% | 2.0 | 92.4% | 4.9 | 0.892 |
| 4 | 15 | 210 | 165% | 2.0 | 92.4% | 4.9 | 0.892 |

TABLE 3

Inventive Waistband Elastic Profiles

| Section | Number of Elastics | Average-Dtex | Average-Pre-Strain | Average-Strand-Spacing (mm) | Open Area (%) | Section-Modulus (gf/mm) | Pressure-Under-Strand (psi) |
|---|---|---|---|---|---|---|---|
| A |  |  |  |  |  |  |  |
| 1 | 40 | 111 | 100% | 0.6 | 81.5% | 8.7 | 0.368 |
| B |  |  |  |  |  |  |  |
| 1 | 50 | 90 | 110% | 0.5 | 80.0% | 8.4 | 0.341 |
| C |  |  |  |  |  |  |  |
| 1 | 35 | 120 | 200% | 0.7 | 83.5% | 8.0 | 0.413 |

TABLE 4

Inventive Cuff Elastic Profiles

| Section | Number of Elastics | Average-Dtex | Average-Pre-Strain | Average-Strand-Spacing (mm) | Open Area (%) | Section-Modulus (gf/mm) | Pressure-Under-Strand (psi) |
|---|---|---|---|---|---|---|---|
| A |  |  |  |  |  |  |  |
| Inner | 50 | 30 | 200% | 0.5 | 88.5% | 2.8 | 0.590 |
| Outer | 50 | 70 | 200% | 0.5 | 82.4% | 6.6 | 0.386 |
| B |  |  |  |  |  |  |  |
| Inner | 25 | 70 | 170% | 0.5 | 82.4% | 6.6 | 0.386 |
| Outer | 25 | 140 | 200% | 1.0 | 87.5% | 6.6 | 0.546 |
| C |  |  |  |  |  |  |  |
| Inner | 25 | 140 | 85% | 0.5 | 75.1% | 13.1 | 0.273 |
| Outer | 25 | 140 | 200% | 1.0 | 87.5% | 6.6 | 0.546 |

Example 1—Belt Pant Article (See, for Example, FIGS. 5, 5A, 6, 7, 7A, and 8)

Example 1 is a belted pant absorbent article. The pant comprises a belt laminate disposed in both the waist regions and the following materials and construction.
Outer Belt Layer (first substrate layer 306): 13 gsm spunbond nonwoven
Inner Belt Layer (second substrate layer 308): 13 gsm spunbond nonwoven
Backsheet Film 126: 12 gsm liquid impermeable polyethylene film
Core Wrap: 10 gsm hydrophilic spunbond nonwoven
AGM: absorbent gelling material
Distribution Layer: crosslinked cellulosic fiber
Acquisition Layer: 43 gsm synthetic acquisition layer
Topsheet 124: 12 gsm hydrophilic spunbond nonwoven
Belt Elastic Profile: Table 1, col B
Cuff Elastic Profile: Table 4, col C

Example 2—Taped Article (See, for Example, FIGS. 9, 9A, and 10)

Example 2 is a side panel taped absorbent article. The taped article comprises a pair of side panels disposed in a first waist region and the following materials and construction.
Elastomeric Ear Panel Outer Layer (first substrate layer 306): 17 gsm carded nonwoven
Elastomeric Ear Panel Inner Layer (second substrate layer 308): 17 gsm spunbond nonwoven
Backsheet Film 126: 12 gsm liquid impermeable polyethylene film
Core Wrap: 10 gsm hydrophilic spunbond nonwoven
AGM: absorbent gelling material
Distribution Layer: crosslinked cellulosic fiber
Acquisition Layer: 43 gsm synthetic acquisition layer
Topsheet 124: 12 gsm hydrophilic spunbond nonwoven
Side Panel Elastic Profile: Table 2, col A
Cuff Elastic Profile: Table 4, col B
Front Waistband: Table 3, col A
Back Waistband: Table 3, col A

Example 3—Side Panel Pant Article (See, for Example, FIGS. 3 and 3B)

Example 3 is a side panel pant absorbent article. The pant article has a pair of side panels disposed in each waist region and comprises the following materials and construction.
Side Panel Outer Layer (first substrate layer 306): 17 gsm carded nonwoven
Side Panel Inner Layer (second substrate layer 308): 17 gsm spunbond nonwoven
Backsheet Film 126: 12 gsm liquid impermeable polyethylene film
Core Wrap: 10 gsm hydrophilic spunbond nonwoven
AGM: absorbent gelling material
Distribution Layer: crosslinked cellulosic fiber
Acquisition Layer: 43 gsm synthetic acquisition layer
Topsheet 124: 12 gsm hydrophilic spunbond nonwoven
Front Side Panel Elastic Profile: Table 2, col B
BackSide Panel Elastic Profile: Table 2, col B
Cuff Elastic Profile: Table 4, col A
Front Waistband: Table 3, col C
Back Waistband: Table 3, col C

TABLE 5

Performance Characteristics of Existing and Inventive Belt Sections
Table 5. Performance Characteristics of Existing and Inventive Belt Sections

| Example Belt Sections | Average-Dtex | Average-Strand-Spacing (mm) | Open Area (%) | Section-Modulus (gf/mm) | Pressure-Under-Strand (psi) |
|---|---|---|---|---|---|
| Currently Marketed Product A (example section 1 of 4) | 1100 | 9.0 | 96.1% | 5.7 | 1.753 |
| Currently Marketed Product A (example section 2 of 4) | 940 | 9.0 | 96.4% | 7.3 | 1.897 |
| Currently Marketed Product A (example section 3 of 4) | 680 | 9.0 | 97.0% | 3.5 | 2.230 |
| Currently Marketed Product B (example section 1 of 4) | 800 | 7.0 | 95.7% | 5.4 | 1.599 |
| Currently Marketed Product B (example section 2 of 4) | 680 | 7.0 | 96.1% | 4.6 | 1.734 |
| Currently Marketed Product C (example section 1 of 4) | 470 | 4.0 | 94.3% | 5.5 | 1.192 |
| Currently Marketed Product C (example section 2 of 4) | 680 | 4.0 | 93.1% | 8.0 | 0.991 |
| Inventive Example (example section 1 of 4) | 160 | 0.5 | 73.4% | 15.0 | 0.255 |
| Inventive Example (example section 2 of 4) | 140 | 0.5 | 75.1% | 13.1 | 0.273 |
| Inventive Example (example section 3 of 4) | 250 | 0.8 | 79.2% | 14.6 | 0.327 |

Figure 19:
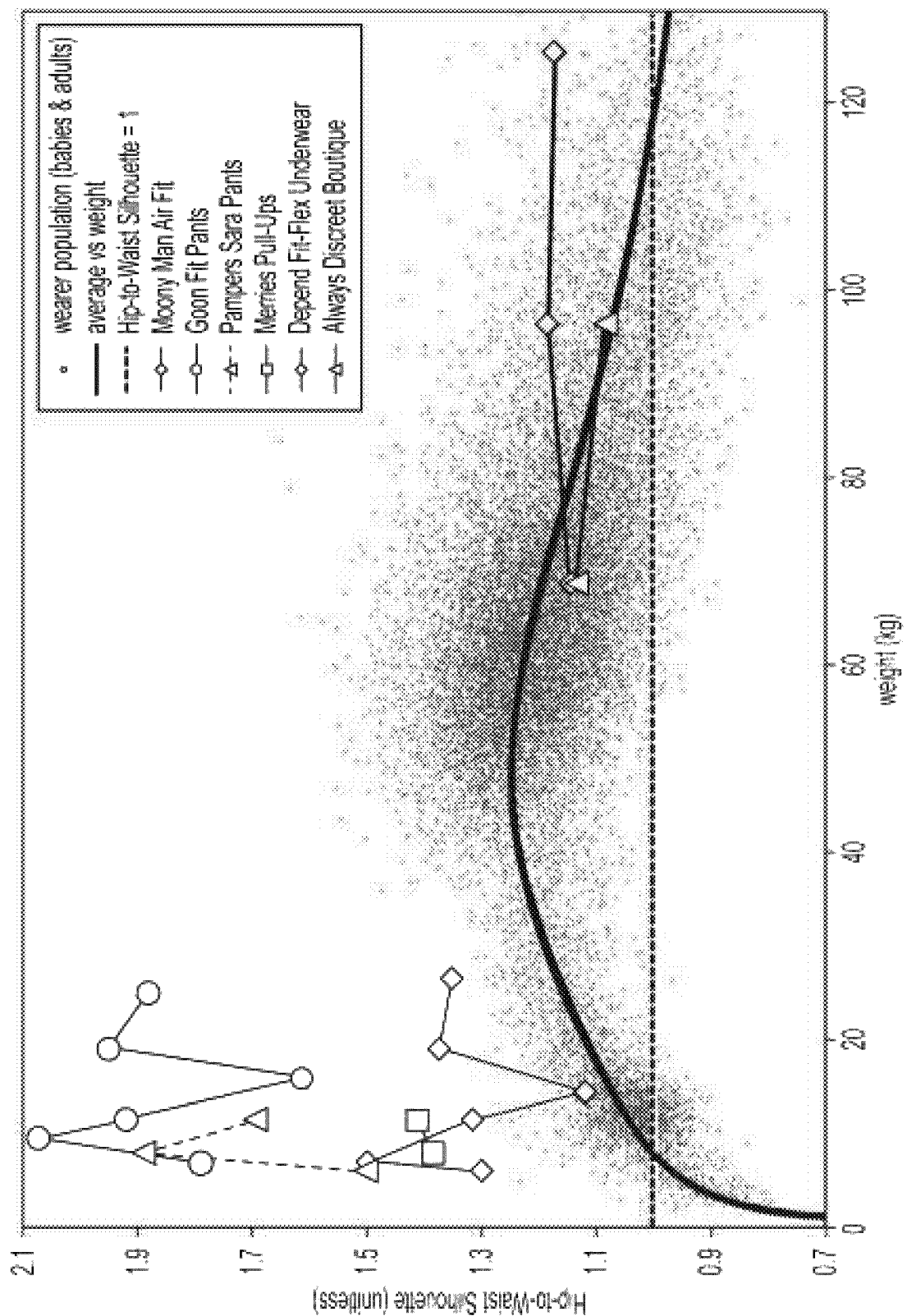
FIG. 19 is a chart which shows examples of existing product arrays and how their Product Hip-to-Waist Silhouettes compare to the Body Hip-to-Waist Silhouettes for the weight range each product is targeted to fit.

A product's "rectangular" nature can be assessed by the Product Hip-to-Waist Silhouette and the Product Waist-to-Crotch Silhouette, as illustrated in FIG. 1. Product Hip-to-Waist Silhouettes from about 0.8 to about 1.1 are more rectangular and are also not possible with today's stranded products as shown in FIG. 19 and in Table 6. Additionally, having a Product Waist-to-Crotch Silhouette from about 0.8 to about 2.0 further enhance this rectangular nature.

TABLE 6

Examples of Product Hip-to-Waist & Waist-to-Crotch Silhouette for Existing Stranded Products

|  | Relaxed Product Waist Width (mm) | Relaxed Product Hip Width (mm) | Relaxed Product Crotch Width (mm) | Product Hip-to-Waist Silhouette | Product Waist-to-Crotch Silhouette |
|---|---|---|---|---|---|
| Moony Man Air Fit | | | | | |
| size S | 122 | 159 | 120 | 1.30 | 1.02 |
| size M | 111 | 166 | 117 | 1.50 | 0.95 |
| size LG | 129 | 170 | 114 | 1.32 | 1.13 |
| size BIG | 146 | 163 | 122 | 1.12 | 1.20 |
| size BIGGER THAN BIG | 139 | 190 | 117 | 1.37 | 1.19 |
| size SUPER | 152 | 206 | 117 | 1.35 | 1.30 |
| Goo.N Yawaraka Fit Pants | | | | | |
| size S | 93 | 166 | 127 | 1.79 | 0.73 |
| size M | 84 | 175 | 122 | 2.07 | 0.69 |
| size LG | 92 | 177 | 117 | 1.92 | 0.79 |
| size BIG | 105 | 170 | 137 | 1.61 | 0.77 |
| size BIGGER THAN BIG | 96 | 186 | 127 | 1.95 | 0.75 |
| size SUPER | 117 | 220 | 178 | 1.88 | 0.66 |
| Pampers Sara Sara Pants | | | | | |
| size S | 111 | 167 | 81 | 1.50 | 1.37 |
| size M | 89 | 168 | 85 | 1.89 | 1.04 |
| size L | 102 | 173 | 84 | 1.69 | 1.22 |
| Merries Pull-Ups | | | | | |
| size M | 125 | 173 | 122 | 1.38 | 1.03 |
| size L | 131 | 185 | 125 | 1.41 | 1.05 |
| Depend Fit-Flex Underwear for Women - Moderate | | | | | |
| size S/M | 230 | 263 | 114 | 1.14 | 2.02 |
| size L | 231 | 274 | 118 | 1.18 | 1.96 |
| size XL | 249 | 291 | 120 | 1.17 | 2.07 |
| Always Discreet Boutique | | | | | |
| size S/M | 286 | 325 | 102 | 1.14 | 2.80 |
| size L | 304 | 330 | 107 | 1.08 | 2.84 |

Table 7 below illustrates inventive stranded products, whose Product Hip-to-Waist Silhouettes and Product Waist-to-Crotch Silhouettes provide for a more uniform package. These inventive products are provided simply as non-limiting examples.

TABLE 7

Examples of Product Hip-to-Waist & Waist-to-Crotch Silhouette for Inventive Stranded Products

| Inventive Beamed Product | Relaxed Product Waist Width (mm) | Relaxed Product Hip Width (mm) | Relaxed Product Crotch Width (mm) | Product Hip-to-Waist Silhouette | Product Waist-to-Crotch Silhouette |
|---|---|---|---|---|---|
| size M | 145 | 155 | 102 | 1.07 | 1.42 |
| size L | 170 | 175 | 105 | 1.03 | 1.62 |
| size S/M | 300 | 320 | 120 | 1.07 | 2.50 |
| size L | 360 | 380 | 130 | 1.06 | 2.77 |

Absorbent Article Sections

Components of absorbent articles comprising elastomeric laminates 302 may be sectioned to enable measurement and detailed characterization of the structure. Waistband 122 (see FIGS. 3B, 4, and 10), waistcap 123 (see FIG. 9), inner leg cuff 150, outer leg cuff 140, and transverse barrier 165 all comprise 1 section. With regard to the waistband 122, waistcap 123, inner leg cuff 150, outer leg cuff 140 and transverse barrier 165 the section is defined as the region disposed between and including the distal most elastic and the proximal most elastic.

Other components such as the chassis 200, topsheet 124 (see FIGS. 7A and 7C), backsheet 125 (see FIGS. 7C and 7D), side panel 330 (see FIG. 3B), ear panel 530 (FIGS. 9 and 10), and belt panel 430 (see FIGS. 7 and 7A) all comprise multiple sections as described herein. With regard to the side panel 330, ear panel 530 and belt panel 430 the portion of the component to be sectioned is defined as the region disposed between and including the distal most elastic of the elastomeric laminate 302 and the proximal most elastic of the elastomeric laminate 302. The region is defined by a first line extending parallel to the lateral axis 44 and passing through the distal most point of the distal most elastic and a second line extending parallel to the lateral axis and passing through the proximal most point of the proximal most elastic. For each of these elements, the region is then divided into 4 equal sections, defined by three lines disposed parallel to the lateral axis 44 and disposed at 25%, 50% and 75% of the distance between the first line and second line. The region comprises a first section which includes the distal most elastic, a fourth section which includes the proximal most elastic, a second section disposed adjacent the first section and a third section disposed between the second section and the fourth section.

With regard to the chassis 200, topsheet 124 (see FIGS. 7A and 7C), and backsheet 125 (see FIG. 7C) wherein the elastics 316 of the elastomeric laminate 302 extend in a substantially longitudinal orientation, the portion of the component to be sectioned is defined as the region disposed between and including the distal most elastic of the elastomeric laminate 302 on a first side of the longitudinal axis 42 and the distal most elastic of the elastomeric laminate 302 on a second side of the longitudinal axis 42. The region is defined by a first line extending parallel to the longitudinal axis 42 and passing through the distal most point of the distal most elastic on a first side of the longitudinal axis 42 and a second line extending parallel to the longitudinal axis 42 and passing through the distal most point of the distal most elastic on a second side of the longitudinal axis 42. For each of these elements, the region is then divided into 4 equal sections, defined by three lines disposed parallel to the longitudinal axis 42 and disposed at 25%, 50% and 75% of the distance between the first line and second line. The region comprises a first section which includes the distal most elastic on the first side of the longitudinal axis, a fourth section which includes the distal most elastic on the second side of the longitudinal axis, a second section disposed adjacent the first section and a third section disposed between the second section and the fourth section.

With regard to the chassis 200, topsheet 124, and backsheet 125 (see FIG. 7D) wherein the elastics 316 of the elastomeric laminate 302 extend in a substantially lateral orientation, the portion of the component to be sectioned is defined as the region disposed between and including the distal most elastic of the elastomeric laminate 302 on a first side of the lateral axis 44 and the distal most elastic of the elastomeric laminate 302 on a second side of the lateral axis 44. The region is defined by a first line extending parallel to the lateral axis 44 and passing through the distal most point of the distal most elastic on a first side of the lateral axis 44 and a second line extending parallel to the lateral axis 44 and passing through the distal most point of the distal most elastic on a second side of the lateral axis 44. For each of these elements, the region is then divided into 4 equal sections, defined by three lines disposed parallel to the lateral axis 44 and disposed at 25%, 50% and 75% of the distance between the first line and second line. The region comprises a first section which includes the distal most elastic on the first side of the lateral axis, a fourth section which includes the distal most elastic on the second side of the lateral axis, a second section disposed adjacent the first section and a third section disposed between the second section and the fourth section.

Absorbent Article Packaging and Package Indicia

Figure 17:
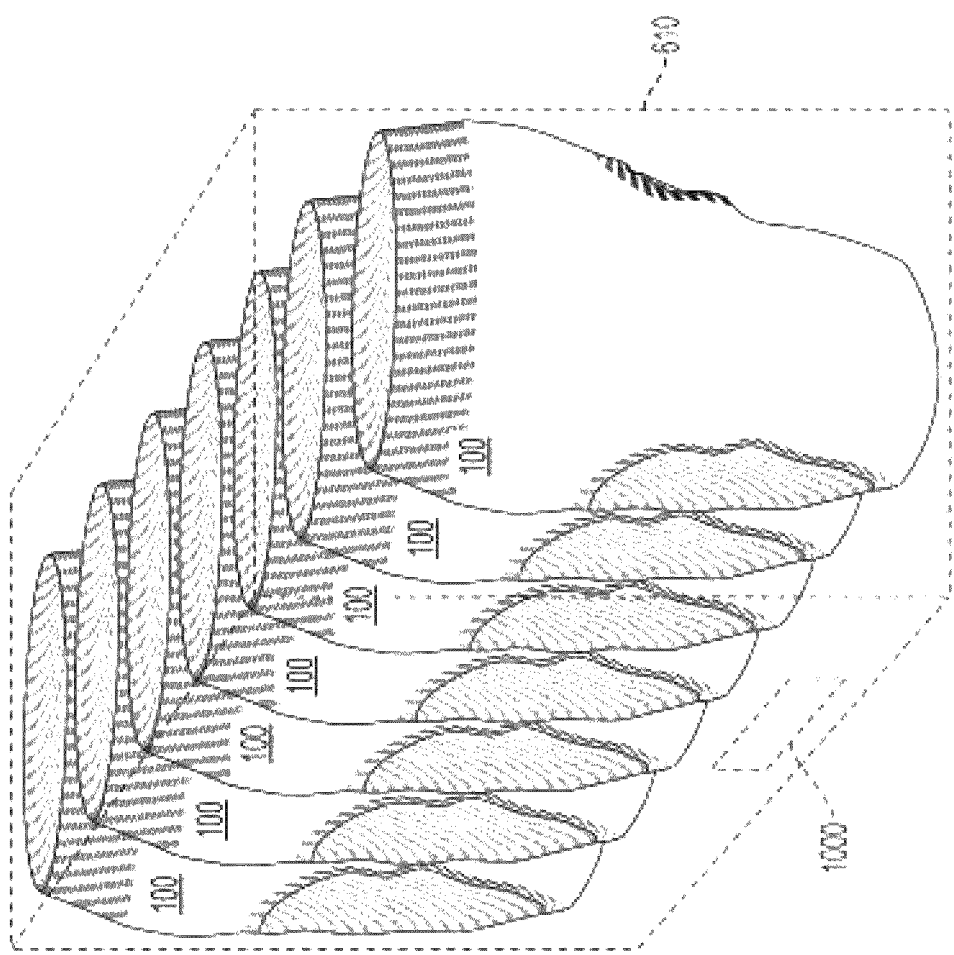
FIG. 17 illustrates packaged articles with a sizing indicia and with a Product Hip-to-Waist Silhouette of from about 0.8 to about 1.1, and a Product Waist-to-Crotch Silhouette of from about 0.8 to about 2.0.
Figure 18:
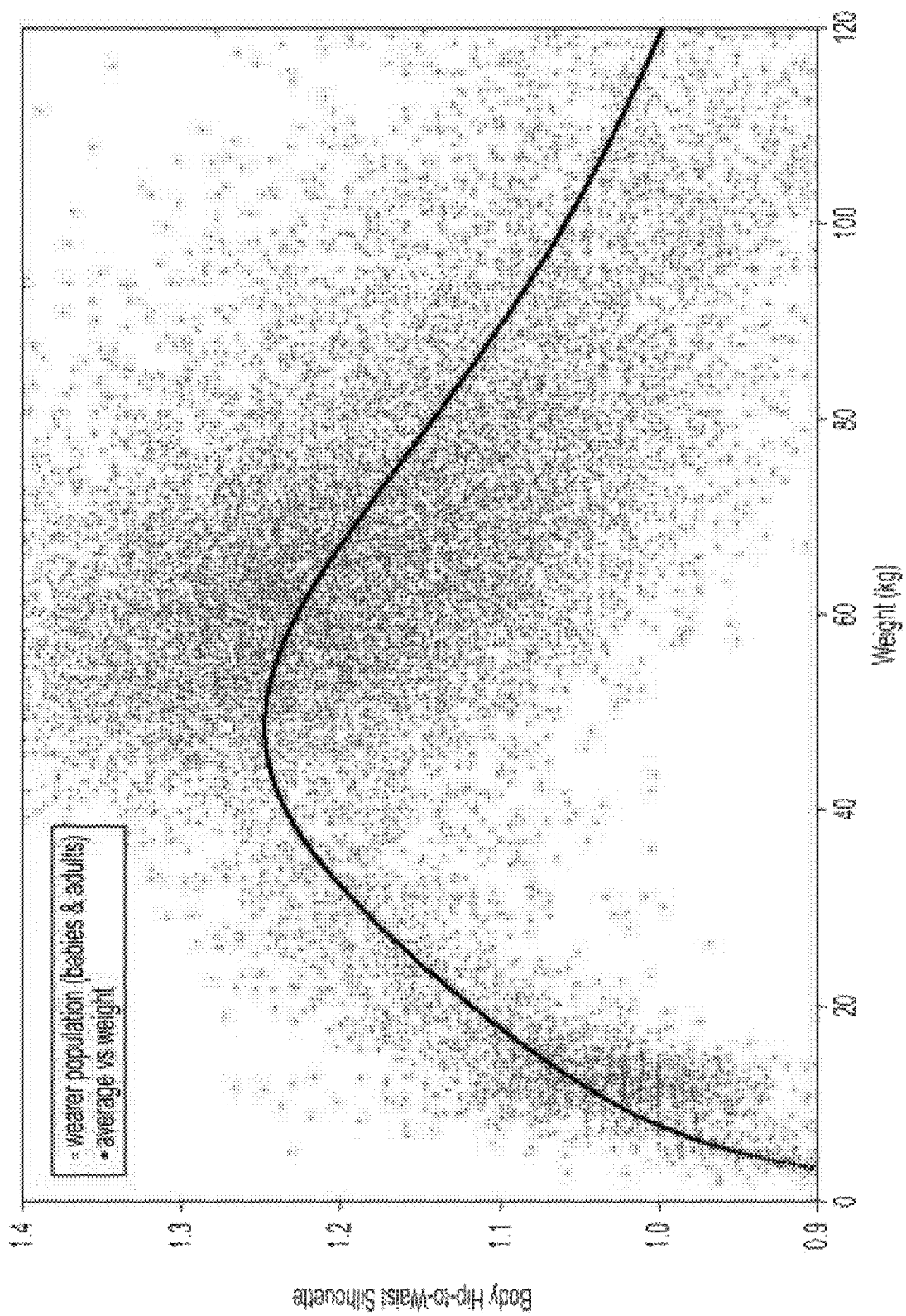
FIG. 18 is a chart which shows how the Body Hip-to-Waist Silhouette and Average Body Hip-to-Waist Silhouette changes as body weight increases.

Referring to FIG. 17, the absorbent articles 100 of the present disclosure may be placed into packages 610 (shown as dotted lines so the absorbent articles 100 may be seen). The packages may comprise polymeric films and/or other materials. Graphics and/or indicia 1000 relating to properties of the absorbent articles may be formed on, printed on, positioned on, and/or placed on outer portions of the packages. Each package may comprise a plurality of absorbent articles 100. The absorbent articles 100 may be packed under compression so as to reduce the size of the packages, while still providing an adequate amount of absorbent articles per package. By packaging the absorbent articles under compression, caregivers can easily handle and store the packages 610, while also providing distribution savings to manufacturers owing to the size of the packages. Accordingly, packages 610 of the absorbent articles 100 of the present disclosure may have an In-Bag Stack Height as disclosed in U.S. Publication No. 2014/0052088 to Weisman, titled ABSORBENT PRODUCTS HAVING IMPROVED PACKAGING EFFICIENCY.

Desirably, the package 610 has parallel sides and a package top that is parallel to the package bottom, making the package ideal for stacking on a shelf for storage or for display in a store for purchase by consumers. Typically packages 610 of absorbent articles 100 are labeled sizing information that may include a recommended wearer's weight range (typically for babies, infants, and toddlers) and/or a recommended wearer's waist circumference (typically for adult absorbent article products) that the packaged article is intended to fit. As a result, the weight and/or the waist circumference information is most often placed on the package 610 as part of the indicia 1000 to identify the appropriate size of the article needed by the consumer.

Further, the indicia 1000 may illustrate the wearer wearing the article and/or a separate indicia may illustrate the article component or feature. Regarding absorbent articles for babies, descriptions of suitable stages of development indicia and methods of displaying packages comprising absorbent articles may be found in U.S. Pat. No. 7,222,732 to Ronn, titled MERCHANDISE DISPLAY SYSTEM FOR IDENTIFYING DISPOSABLE ABSORBENT ARTICLE CONFIGURATIONS FOR WEARERS.

Desirably, the package 610 has parallel sides and a package top that is parallel to the package bottom, making the package ideal for stacking on a shelf for storage or for display in a store for purchase by consumers. Typically packages 610 of absorbent articles 100 are labeled with a recommended wearer weight range (typically for babies, infants, and toddlers) and/or by waist circumference (typically for adult absorbent article products) that the packaged article is intended to fit. As a result, the weight and/or the waist circumference information is most often placed on the package 610 as part of the indicia 1000 to identify the appropriate size of the article needed by the consumer.

Further, the indicia 1000 may illustrate the wearer wearing the article and/or a separate indicia may illustrate the article component or feature. Regarding absorbent articles for babies, descriptions of suitable stages of development indicia and methods of displaying packages comprising absorbent articles may be found in U.S. Pat. No. 7,222,732 to Ronn, titled MERCHANDISE DISPLAY SYSTEM FOR IDENTIFYING DISPOSABLE ABSORBENT ARTICLE CONFIGURATIONS FOR WEARERS.

Example Claim Combinations

Example Claim Set 1

1. An absorbent article, comprising:
a front waist region, a back waist region, and a crotch region therebetween;
a chassis comprising a topsheet, a backsheet and an absorbent core disposed between the topsheet and the backsheet, wherein the chassis comprises a front end edge, a back end edge, and a pair of laterally opposing side edges;
a back belt joined to the back waist region of the chassis and extending outboard of the back waist region of the chassis;
a front belt joined to the front waist region of the chassis and extending outboard of the front waist region of the chassis;
wherein the front belt is joined to the back belt at or adjacent the laterally opposing belt side edges to form leg openings and a waist opening to form a closed-form pant;
a longitudinal axis extending from the midpoint of the front waist edge to the midpoint of the back waist edge;
a lateral axis extending perpendicular to the longitudinal axis through the midpoint of the longitudinal axis;
wherein the back belt comprises a first plurality of elastics comprising greater than about 40 elastic strands, and wherein the front belt comprises a second plurality of elastics comprising greater than about 40 elastic strands;
wherein the first plurality of elastics has an Average-Strand-Spacing of less than 4 mm, and wherein the second plurality of elastics has an Average-Strand-Spacing of less than 4 mm;
wherein the Product Hip-to-Waist Silhouette is from about 0.8 to about 1.1;
wherein the Product Waist-to-Crotch Silhouette is from about 0.8 to about 2.0; and
wherein the absorbent article has a Relaxed Product Waist Width from about 80 mm to about 270 mm and a Relaxed Product Hip Width from about 80 mm to about 300 mm.

2. The absorbent article according to claim 1, wherein the back belt is divided into 4 equal sections, wherein Section 4 comprises a proximal end edge of the back belt, Section 1 comprises a distal end edge of the back belt, Section 2 is proximate to Section 1 and Section 3 is proximate to Section 4, and wherein the front belt is divided into 4 equal sections, wherein Section 4 comprises a proximal end edge of the front belt, Section 1 comprises a distal end edge of the front belt, Section 2 is proximate to Section 1 and Section 3 is proximate to Section 4.

3. The absorbent article according to any of the preceding claims, wherein the front belt comprises a front inner (wearer-facing) nonwoven and a front outer (garment facing) nonwoven, and wherein the back belt comprises a back inner (wearer-facing) nonwoven and a back outer (garment facing) nonwoven.

4. The absorbent article of claim 3, wherein the front inner nonwoven and the back inner nonwoven are separate and longitudinally spaced from each other.

5. The absorbent article according to any of claims 3 and 4, wherein the front outer nonwoven and the back outer nonwoven are separate and longitudinally spaced from each other.

6. The absorbent article of claim 4, wherein the front outer nonwoven and the back outer nonwoven are formed from the same outer cover nonwoven layer, such that the outer cover nonwoven layer continuously extends from the front waist region to the back waist region.

7. The absorbent article of claim 2, wherein section 1 of at the front belt comprises more elastics than sections 2, 3, or 4 of the front belt, and wherein section 1 of at the back belt comprises more elastics than sections 2, 3, or 4 of the back belt.

8. The absorbent article according to any one of claims 2 and 7, wherein at least one of the sections of the front belt comprise greater than 10 elastic strands, and wherein at least two of the sections of the back belt comprise greater than 10 elastic strands.

9. The absorbent article according to any one of claims 2, 7 and 8, wherein at least two of the sections of the front belt have an Average-Strand-Spacing of less than about 3 mm, and wherein at least three of the sections of the back belt have an Average-Strand-Spacing of less than about 3 mm.

10. The absorbent article according to any one of claims 2, 7, 8 and 9, wherein the sum of sections 1 and 2 of at the front belt comprises greater than 20 elastic strands, and wherein the sum of sections 1 and 2 of at the front belt comprises greater than 20 elastic strands.

11. The absorbent article according to any of the preceding claims, wherein at least a portion of the first plurality of elastics overlap the absorbent core, and wherein at least a portion of the second plurality of elastics overlap the absorbent core.

12. The absorbent article according to any one of claims 3, 4, 5, and 6, wherein the back inner and outer nonwovens are different in composition, polymer type, fiber diameter, fiber shape, bond pattern, color, nonwoven type (e.g. spunbond, carded, etc.) and/or basis weight.

13. The absorbent article according to any one of claims 2, 7, 8, 9, and 10, wherein sections 1 and 2 of the first plurality of elastics have a different section modulus than sections 1 and 2 of the second plurality of elastics.

14. The absorbent article according to any one of claims 2, 7, 8, 9, 10, and 13, wherein each of the sections of the first plurality of elastics and the sections of the second plurality of elastics have a different section modulus.

15. The absorbent article according to any of the preceding claims, wherein the back belt has a greater longitudinal distance than the front belt along the longitudinal axis, wherein the front and back belts are substantially co-terminus at the waist opening.

16. The absorbent article according to any of the preceding claims, wherein the absorbent article has a Relaxed Product Waist Width from about 170 mm to about 270 mm.

17. The absorbent article according to any one of claims 1-15, wherein the absorbent article has a Relaxed Product Waist Width from about 80 mm to about 180 mm.

18. The absorbent article according to any of the preceding claims, wherein the Relaxed Product Hip Width is from about 80 mm to about 200 mm.

19. The absorbent article according to any of the preceding claims, wherein the Relaxed Product Length is from about 200 mm to about 300 mm.

20. The absorbent article according to any of the preceding claims, wherein the Product Hip-to-Waist Silhouette is from about 0.9 to about 1, and the Product Waist-to-Crotch Silhouette is from about 0.9 to about 1.5.

21. The absorbent article according to any of the preceding claims, wherein the Product Hip-to-Waist Silhouette is from about 0.95 to about 1, and the Product Waist-to-Crotch Silhouette is from about 1.2 to about 1.35.

22. The absorbent article according to any of the preceding claims, wherein the Product Waist-to-Crotch Silhouette is from about 1.25 to about 1.35.

23. The absorbent article according to any of the preceding claims, wherein the first plurality and the second plurality of elastics comprise PolyUrethane Urea.

24. The absorbent article according to any of the preceding claims, wherein the first plurality and the second plurality of elastics comprise a silicone oil coating.

25. The absorbent article according to any of the preceding claims, wherein the back belt comprises a first substrate layer and a second substrate layer and the first plurality of elastics is disposed between and joined to the first and second substrate layers via an adhesive.

26. The absorbent article according to claim 25, wherein the adhesive is selected from the group consisting of Styrenic block copolymers, Polyolefins, Ethylene-vinyl Acetates, Polyurethanes, Ethylene-propylene copolymers, Propylene-ethylene copolymers, Polyolefin block polymers, Polyolefin homo-polymers, Polyesters, Polyamides, Silicones, Cyanoacrylics, Acrylics, butyl rubber, and combinations thereof.

27. The absorbent article according to any of the preceding claims, wherein the first plurality and the second plurality of elastics consists essentially of PolyUrethane Urea.

28. The absorbent article according to any of the preceding claims, wherein the first plurality and the second plurality of elastics consists of PolyUrethane Urea.

29. The absorbent article according to any one of claims 25 and 26, wherein the front belt comprises a third substrate layer and a fourth substrate layer and the second plurality of elastics is disposed between and joined to the first and second substrate layers via the adhesive.

30. The absorbent article according to any one of claims 25 and 26, wherein the front belt comprises a third substrate layer, and wherein the second plurality of elastics is disposed between and joined to the second and third substrate layers via the adhesive.

31. The absorbent article according to any one of claims 25 and 26, wherein the second plurality of elastics is disposed between and joined to the first and second substrate layers via the adhesive.

32. The absorbent article according to claim 25, wherein the adhesive is selected from the group consisting of thermoplastic, thermoset, hot-melt, pressure sensitive, solvent-based, and reactive thermoset.

33. A method for producing the absorbent article(s) of any of the preceding claims, comprising the step of unwinding the first plurality of elastics are unwound from a single beam to form the elastomeric laminate.

34. A method for producing the absorbent article(s) of any of the preceding claims, comprising the step of unwinding the first plurality of elastics and the second plurality of elastics from a single beam to form the elastomeric laminate.

35. A method for producing the absorbent article(s) of any one of claims 1-32, comprising the first step of unwinding the first plurality of elastics from a first beam and comprising the second step of unwinding the second plurality of elastics from a second beam, the second beam separate from the first beam, to form the elastomeric laminate.

Example Claim Set 2

1. An absorbent article, comprising:
a front waist region, a back waist region, and a crotch region therebetween;
a chassis comprising a topsheet, a backsheet and an absorbent core disposed between the topsheet and the backsheet, wherein the chassis comprises a front end edge, a back end edge, and a pair of laterally opposing side edges;
a back belt joined to the back waist region of the chassis and extending outboard of the back waist region of the chassis;
a front belt joined to the front waist region of the chassis and extending outboard of the front waist region of the chassis;
wherein the front belt is joined to the back belt at or adjacent the laterally opposing belt side edges to form leg openings and a waist opening to form a closed-form pant;
a longitudinal axis extending from the midpoint of the front waist edge to the midpoint of the back waist edge;
a lateral axis extending perpendicular to the longitudinal axis through the midpoint of the longitudinal axis;
wherein the back belt comprises a first plurality of elastics comprising greater than about 40 elastic strands, and wherein the front belt comprises a second plurality of elastics comprising greater than about 40 elastic strands;
wherein the first plurality of elastics has an Average-Strand-Spacing of less than 4 mm, and wherein the second plurality of elastics has an Average-Strand-Spacing of less than 4 mm;
wherein the Product Hip-to-Waist Silhouette is from about 0.8 to about 1.1;
wherein the Product Waist-to-Crotch Silhouette is from about 0.8 to about 2.8; and
wherein the article comprises at least one of the following:
(a) Relaxed Product Waist Width is from about 200 mm to about 400 mm;
(b) Relaxed Product Length from about 250 mm to about 450 mm; and
(c) Relaxed Product Hip Width from about 200 to about 450 mm.

2. The absorbent article of claim 1, wherein the back belt is divided into 4 equal sections, wherein Section 4 comprises a proximal end edge of the back belt, Section 1 comprises a distal end edge of the back belt, Section 2 is proximate to Section 1 and Section 3 is proximate to Section 4, and wherein the front belt is divided into 4 equal sections, wherein Section 4 comprises a proximal end edge of the front belt, Section 1 comprises a distal end edge of the front belt, Section 2 is proximate to Section 1 and Section 3 is proximate to Section 4.

3. The absorbent article of claim 1, wherein the front belt comprises a front inner (wearer-facing) nonwoven and a front outer (garment facing) nonwoven, and wherein the back belt comprises a back inner (wearer-facing) nonwoven and a back outer (garment facing) nonwoven.

4. The absorbent article of claim 3, wherein the front inner nonwoven and the back inner nonwoven are separate and longitudinally spaced from each other.

5. The absorbent article according to any one of claims 3 and 4, wherein the front outer nonwoven and the back outer nonwoven are separate and longitudinally spaced from each other.

6. The absorbent article of claim 4, wherein the front outer nonwoven and the back outer nonwoven are formed from the same outer cover nonwoven layer, such that the outer cover nonwoven layer continuously extends from the front waist region to the back waist region.

7. The absorbent article according to any of the preceding claims, wherein the article comprises at least two of the following:
(a) Relaxed Product Waist Width is from about 225 mm to about 375 mm;
(b) Relaxed Product Length is from about 275 mm to about 425; and
(c) Relaxed Product Hip Width is from about 225 mm to about 425 mm.

8. The absorbent article of claim 2, wherein at least one of the sections of the front belt comprise at least 20 elastic strands, and wherein at least two of the sections of the back belt comprise at least 20 elastic strands.

9. The absorbent article according to any one of claims 2 and 8, wherein at least one of the sections of the front belt have an Average-Strand-Spacing of less than about 3 mm, and wherein at least two of the sections of the back belt have an Average-Strand-Spacing of less than about 3 mm.

10. The absorbent article according to any one of claims 2, 8, and 9, wherein the sum of sections 1 and 2 of at the back belt comprises greater than 40 elastic strands; and wherein the sum of sections 1 and 2 of at the front belt comprises greater than 40 elastic strands.

11. The absorbent article according to any of the preceding claims, wherein at least a portion of the first plurality of elastics overlap the absorbent core, and wherein at least a portion of the second plurality of elastics overlap the absorbent core.

12. The absorbent article according to any of the preceding claims, wherein the article comprises at least three of the following:
(a) Relaxed Product Waist Width is from about 250 mm to about 350 mm;
(b) Relaxed Product Length is from about 300 mm to about 400; and
(c) Relaxed Product Hip Width is from about 250 mm to about 400 mm.

13. The absorbent article according to any of the preceding claims, wherein the Relaxed Product Waist Width is from about 275 mm to about 325 mm.

14. The absorbent article according to any of the preceding claims, wherein the Relaxed Product Waist Width is from about 285 mm to about 315 mm.

15. The absorbent article according to any of the preceding claims, wherein the Relaxed Product Length is from about 325 mm to about 375 mm.

16. The absorbent article according to any of the preceding claims, wherein the Relaxed Product Length is from about 335 mm to about 365 mm.

17. The absorbent article according to any of the preceding claims, wherein the Product Hip-to-Waist Silhouette is from about 0.9 to about 1.1, and the Product Waist-to-Crotch Silhouette is from about 0.8 to about 2.5.

18. The absorbent article according to any of the preceding claims, wherein the Product Hip-to-Waist Silhouette is from about 1 to about 1.1, and the Product Waist-to-Crotch Silhouette is from about 0.8 to about 2.

19. The absorbent article according to any of the preceding claims, wherein the Product Hip-to-Waist Silhouette is from about 1.05 to about 1.1, and the Product Waist-to-Crotch Silhouette is from about 1 to about 2.

20. The absorbent article according to any of the preceding claims, wherein the first plurality and the second plurality of elastics comprise PolyUrethane Urea.

21. The absorbent article according to any of the preceding claims, wherein the first plurality and the second plurality of elastics comprise a silicone oil coating.

22. The absorbent article according to any of the preceding claims, wherein the back belt comprises a first substrate layer and a second substrate layer and the first plurality of elastics is disposed between and joined to the first and second substrate layers via an adhesive.

23. The absorbent article according to claim 22, wherein the adhesive is selected from the group consisting of Styrenic block copolymers, Polyolefins, Ethylene-vinyl Acetates, Polyurethanes, Ethylene-propylene copolymers, Propylene-ethylene copolymers, Polyolefin block polymers, Polyolefin homo-polymers, Polyesters, Polyamides, Silicones, Cyanoacrylics, Acrylics, butyl rubber etc.

24. The absorbent article according to any of the preceding claims, wherein the first plurality and the second plurality of elastics consists essentially of PolyUrethane Urea.

25. The absorbent article according to any of the preceding claims, wherein the first plurality and the second plurality of elastics consists of PolyUrethane Urea.

26. The absorbent article according to any one of claim 22 or 23, wherein the front belt comprises a third substrate layer and a fourth substrate layer and the second plurality of elastics is disposed between and joined to the third and fourth substrate layers via the adhesive.

27. The absorbent article according to any one of claim 22 or 23, wherein the front belt comprises a third substrate layer, and wherein the second plurality of elastics is disposed between and joined to the second and third substrate layers via the adhesive.

28. The absorbent article according to any one of claim 22 or 23, wherein the second plurality of elastics is disposed between and joined to the first and second substrate layers via the adhesive.

29. The absorbent article according to claim 22, wherein the adhesive is selected from the group consisting of thermoplastic, thermoset, hot-melt, pressure sensitive, solvent based, reactive thermoset, and combinations thereof.

30. A method for producing the absorbent article(s) of any of the preceding claims, comprising the step of unwinding the first plurality of elastics are unwound from a single beam to form the elastomeric laminate.

31. A method for producing the absorbent article(s) of any of the preceding claims, comprising the step of unwinding the first plurality of elastics and the second plurality of elastics from a single beam to form the elastomeric laminate.

32. A method for producing the absorbent article(s) of any one of claims 1-29, comprising the first step of unwinding the first plurality of elastics from a first beam and comprising the second step of unwinding the second plurality of elastics from a second beam, the second beam separate from the first beam, to form the elastomeric laminate.

Methods

General Sample Preparation

The General Sample Preparation is intended to be used for methods that do not have specific sample preparation instructions within the method itself.

The When collecting a specimen for testing, the specimen must contain a plurality of elastic strands and/or an elastic material; film, elastic scrim, elastic foam, elastic ribbons, elastic strips, etc. In situations where the elastic material and/or elastic strands is not fully secured within the sample, the test specimen must be obtained in a way that elastic material and/or elastic strands within the test region of the specimen are as they were intended and not altered as a result of collection of the specimen. If the elastic material or any elastic strands release, creep or become separated within or from the laminate, the specimen is discarded and a new specimen prepared.

For pants, remove the side panels where they are attached to the chassis and separate the side panels at the side seams. Identify the elastic material that transverses the entire width of the panel. Identify the longitudinally distal most edge of the elastic material or elastic strand (closest to the waist edge) and the longitudinally proximal most edge of the elastic material or elastic strand (closest to the leg edge) determine the midpoint between the distal most elastic strand or elastic material edge and the proximal most elastic strand or elastic material edge. Cut a 40 mm wide strip laterally across the entire panel centered at the midpoint. Repeat for each front and rear side panel that contains elastic material and/or elastic strands.

For taped, remove ear panels where they are attached to the chassis. Identify the elastic material that transverses the entire width of the panel. Identify the distal most elastic material edge or elastic strand (closest to the waist edge) and the proximal most elastic material edge or elastic strand (closest to the leg edge) determine the midpoint between the distal most elastic strand or elastic material edge and the proximal most elastic strand or elastic material edge. Cut a 40 mm wide strip laterally across the entire ear panel centered at the midpoint. Repeat for each front and rear ear panel that contains elastic material and/or elastic strands.

For a belted article, mark the product on the front and back by extending a line from along the side of the core to the waist edge. Remove the belt from the article, using an appropriate means (e.g. freeze spray), taking care not to delaminate the belt or release the elastics. Separate the front belt from the back belt along any seams. Identify the distal most elastic material edge or elastic strand (closest to the waist edge) and the proximal most elastic material edge or strand (closest to the leg edge) determine the midpoint between the distal most elastic strand or elastic material edge and the proximal most elastic strand or elastic material edge. Cut a 40 mm wide strip parallel to the waist edge if linear or to the elastic strands if linear and centered at the midpoint, across the entire belt portion. If the strip has a region that does not contain elastic strands or elastic material (e.g., a portion that overlapped the core, etc.) cut along the ends of the elastic strands/elastic material, to remove the non-elastic region and treat as two specimens.

For waistbands, they are tested as a single piece of material. Remove the belt from the article, using an appropriate means (e.g. freeze spray), taking care not to delaminate the belt or release the elastics.

For the leg cuffs, each of the leg cuffs are tested as a single piece of material. The inner leg cuff sample is considered to be the portion of the inner leg cuff that extends from the proximal most edge of the inner leg cuff to and including the distal most elastic of the inner leg cuff and extending longitudinally to the front and back waist edges of the chassis. The outer leg cuff sample is considered to be the portion of the outer leg cuff that extends from the distal most edge of the outer leg cuff to and including the proximal most elastic of the outer leg cuff and extending longitudinally to the front and back waist edges of the chassis.

For all specimen strips calculate a Span Corrected Width (SCW) is calculated as:

$$\text{Span Corrected Width} = d\left(\frac{n}{n-1}\right)$$

where d is the distance (mm) between the two distal strands, and n is the number of strands, when n>1. Clamp the strip at each end and measure the length between the clamps to the nearest 1 mm. Apply a weight equal to 3 g/mm SCW. After 10 seconds measure the final weight to the nearest 1 mm. Calculate the elongation as (Final Length–Initial Length)/Initial length.

Product Measurement Preparation for Donning-Ratio, Product Length-to-Waist Silhouette and Product Hip-to-Waist Silhouette All measurements are conducted at 22° C.+/−2° and 50% RH+/−20%.

Purpose

This method is used to prepare pant type products for subsequent dimensional measurement. The method provides a consistent means of opening a product that has been removed from a bag. This method is applicable to all forms of pant products. A constant rate of extension tensile testing machine with computer interface is used.

A load cell is chosen so that the load cell capacity ensures accuracy of a 5N load to within 0.1N.

Sample Holder Apparatus

Figure 20:
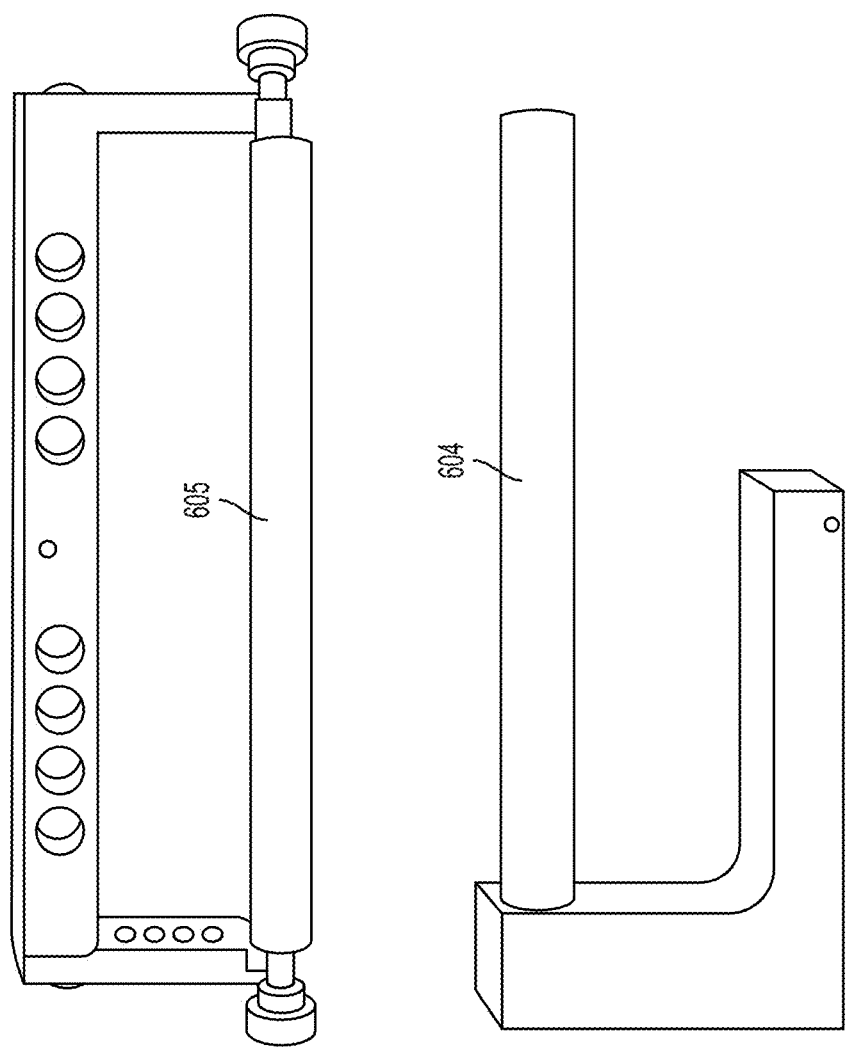
FIG. 20 shows Bar C (604) and Bar O (605) of the Sample Holder Apparatus.

"C" (604) and "O" (605) Bar attachments each with a rod radius of 9.50 mm that extend longer than the length of the longest side seam. Refer to FIG. 20. The bars are mounted horizontally in the tensile tester with their longitudinal axes in the same vertical plane and with upper bar mounted directly above the lower bar.

Equipment Set Up

Calibrate tensile tester equipment according to the instrument manufacturer's recommendations.

Figure 21:
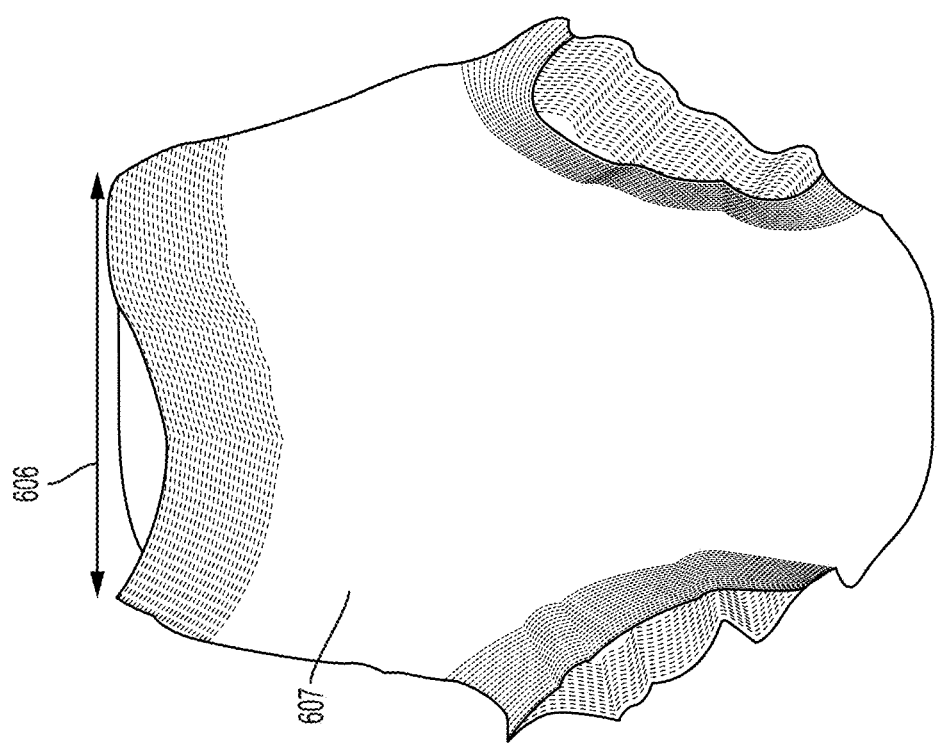
FIG. 21 shows a flat, unfolded closed-form pant.

The initial gauge length is determined by removing 10 sample products from the bag, unfolding the pant products (607) and laying them flat as illustrated in FIG. 21, below and measuring the distance between the sides of the pant at the waist as shown (606). The average of the waist measurement will be used as the initial gauge length for the specific set of specimens. The initial gauge length is the distance from the uppermost edge of the upper bar to the lowermost edge of the lower bar.

Figure 22:
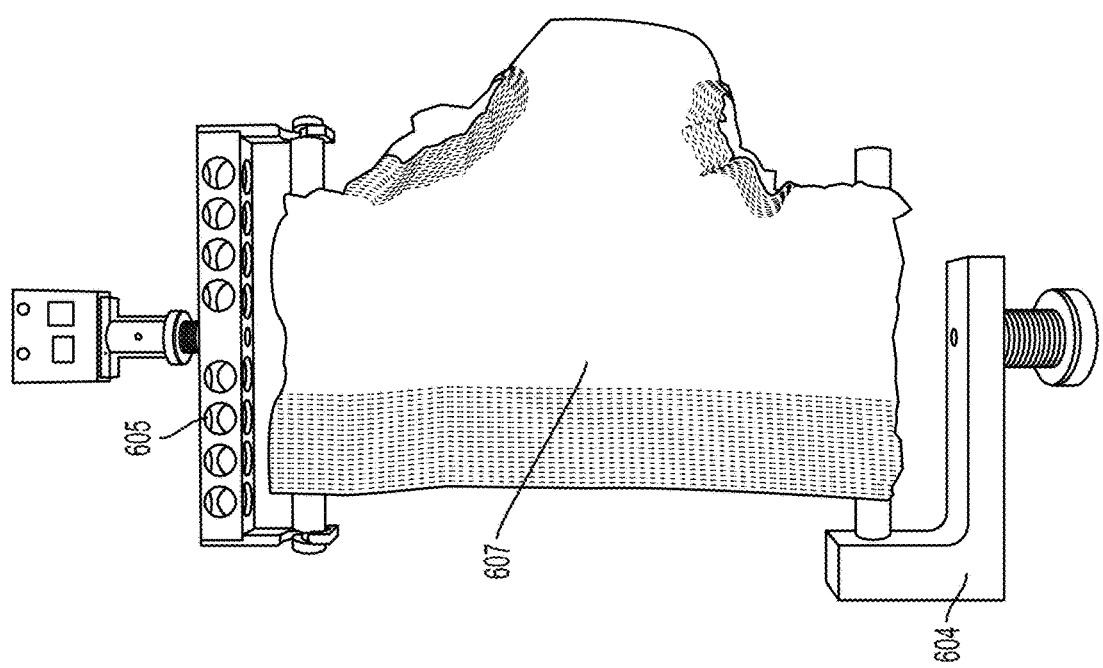
FIG. 22 shows a closed-form pant in the testing apparatus.

Apply the whole product (607) to the bars as shown in FIG. 22 while minimizing manipulation of the specimen. Pull Sample to 5 N Force then hold for 10 seconds. Return to initial gauge length.

Crosshead Speed=254.0 mm/min, Data acquisition rate=50 Hz.

Cycles=1

Remove the specimen from the bars while minimizing manipulation. Lay the specimen flat with the front side facing upward as shown in FIG. 2.

Repeat for all 10 specimens

Physical Measurements

Each of the measurements below is to be conducted on 10 separate like specimens and the average of the 10 separate like specimens is considered to be the measurement for that specific specimen set.

Relaxed Product Length (600)

Relaxed Product Length is the longitudinal distance between the longitudinally distal most point in the crotch region and the longitudinally distal most point along the front waist edge. The longitudinal distance is measured parallel to the longitudinal axis of the product. Refer to FIG. 2.

Relaxed Product Hip Width (601)

Relaxed Product Hip Width is the lateral distance from the laterally distal most point of the left side edge of the product at the upper edge of the left leg opening to the laterally distal most point of the right side edge of the product at the upper edge of the right leg opening. Refer to FIG. 2. The lateral distance is measured perpendicular to the longitudinal axis of the product.

Relaxed Product Waist Width (602)

Relaxed Product Waist Width is the lateral distance from the distal most point at the right side of the front waist edge to the distal most point at the left side of the front waist edge. The lateral distance is measured perpendicular to the longitudinal axis of the product. Refer to FIG. 2.

Relaxed Product Crotch Width (608)

Relaxed Product Crotch Width is the lateral distance from the laterally distal most point of the left side edge of the product at the lower edge of the left leg opening to the laterally distal most point of the right side edge of the product at the lower edge of the right leg opening. Refer to FIG. 2. The lateral distance is measured perpendicular to the longitudinal axis of the product.

Average-Strand-Spacing

Using a ruler calibrated against a certified NIST ruler and accurate to 0.5 mm, measure the distance between the two distal strands within a section to the nearest 0.5 mm, and then divide by the number of strands in that section−1

$$\text{Average-Strand-Spacing} = d/(n-1) \text{ where } n > 1$$

report to the nearest 0.1 mm.

Pressure-Under-Strand (Also Referred to as Average Pressure-Under-Strand)

Figure 16:
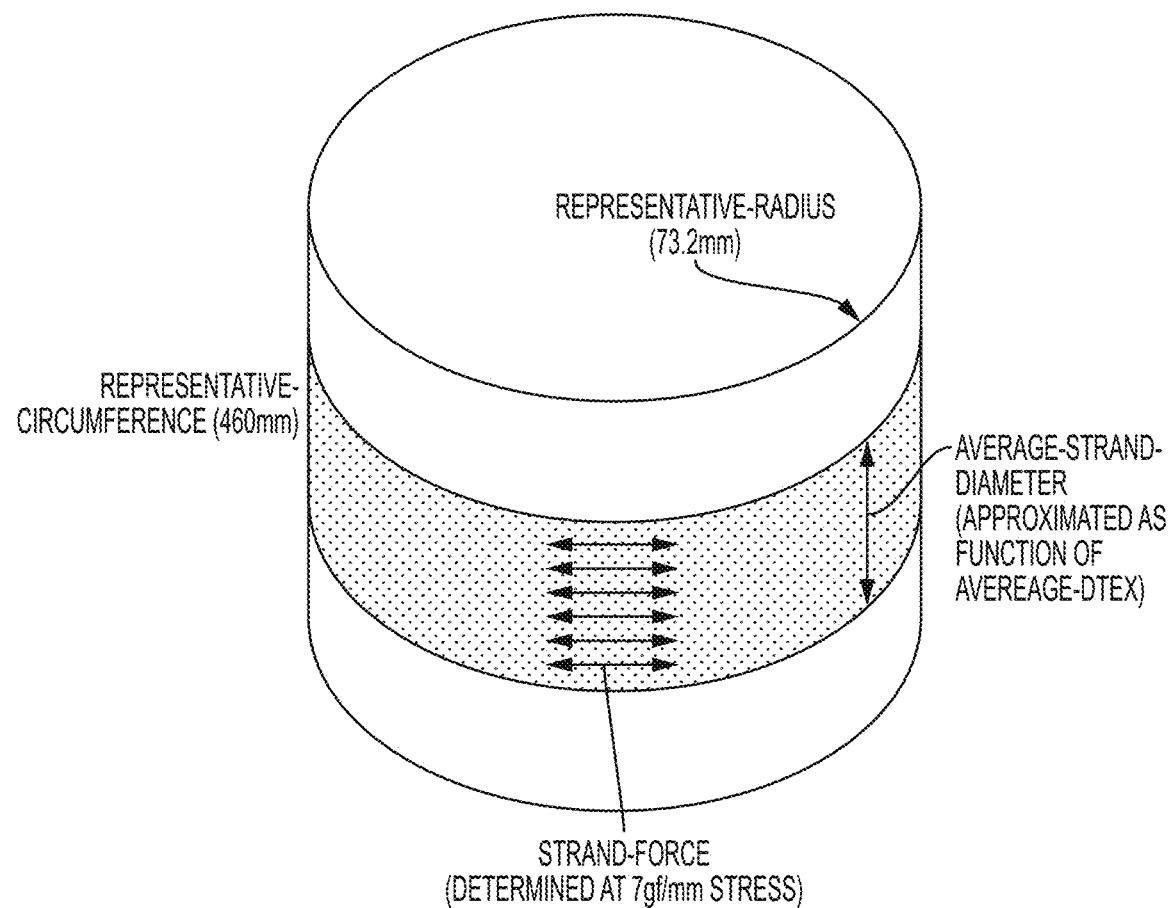
FIG. 16 illustrates Pressure-Under-Strand.

Defined as the average pressure imparted by each individual elastic strand of a section under specific conditions. These conditions are defined as (refer to FIG. 16):

The section is pulled to a Stress of 7 gf/mm (within a consumer preferred range of stresses as determined experimentally)

The section is pulled over a cylinder whose circumference is defined as a Representative-Circumference Where:

Pressure-Under-Strand (psi)=1.422*Strand-Force/(2*Representative-Radius*Average-Strand-Diameter)

Representative-Radius (mm)=Representative-Circumference/(2*pi)

Representative-Circumference (mm)=460 mm

Stress (gf/mm)=(Summation of Strand-Forces within a section)/(Section-Width)

Section-Width (mm)=(Number of Elastics in the section) *Average-Strand-Spacing (mm)

Strand-Force (gf)=Strand-Strain (%)*0.046875*Average-Dtex

Strand-Strain (%)=strain in each elastic strand within a section

Average-Strand-Diameter (mm)=2*sqrt (Strand-Cross-Sectional-Area/pi)

Strand-Cross-Sectional-Area (mm$^2$)=Average-Dtex/Strand-Density/10,000

Strand-Density (g/cc)=1.15 g/cc (industry standard for PolyUrethaneUrea based spandex elastics)

Dtex (g/10,000 m)=Standard textile unit of measure. Dtex is weight in grams for 10,000 m of the material Average-Pre-Strain=Amount of stretch in elastic strands in a section prior to combining with substrate layer(s).

Maximum-Strain=Average-Pre-Strain. This is the maximum amount of strain each section can be pulled to. It cannot exceed the Average-Pre-Strain.

Maximum-Section-Force=Summation of each strand in the section pulled to the Maximum-Strain.

Section-Modulus

Figure 15:
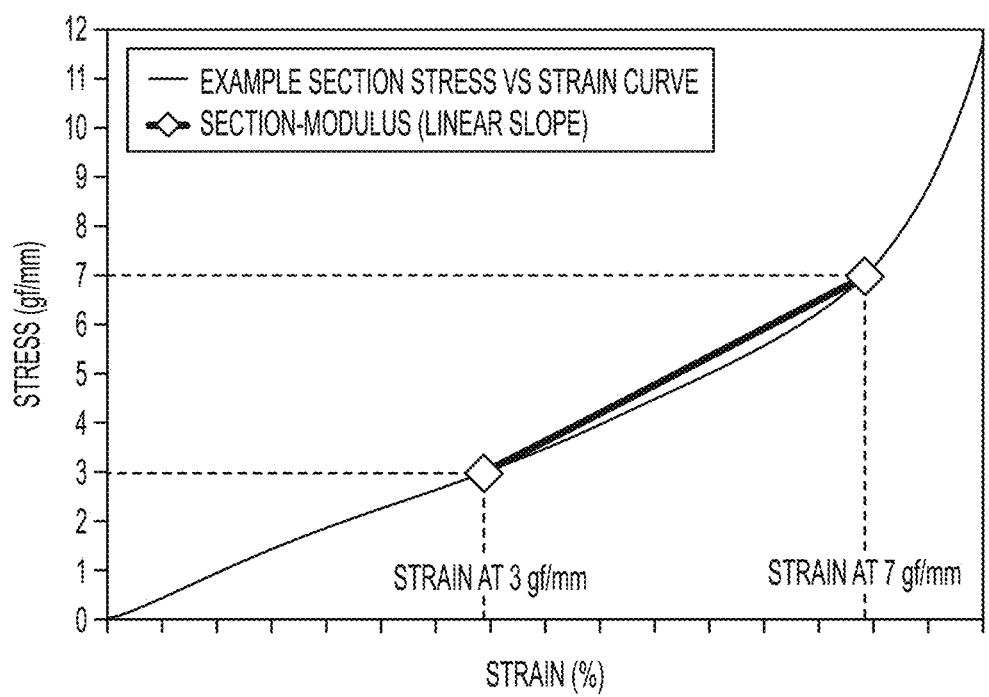
FIG. 15 illustrates the SECTION-MODULUS.

Defined as the modulus of a given section. Section-Modulus (also referred to as modulus) is the linear slope of the stress vs strain data of the section between 3 gf/mm and 7 gf/mm (refer to FIG. 15). Section-Modulus is calculated as:

$$\text{Section-Modulus} = [7 \text{ gf/mm} - 3 \text{ gf/mm}]/[(\text{section strain at } 7 \text{ gf/mm}) - (\text{section strain at } 3 \text{ gf/mm})]$$

Where:

section strain at 7 gf/mm=7 gf/mm*(Average-Strand-Spacing)/DTEX-FACTOR section strain at 3 gf/mm=3 gf/mm*(Average-Strand-Spacing)/DTEX-FACTOR Average-Strand-Spacing (mm)=d/(n−1)

d is the distance (mm) between the two distal strands of the section n is the number of strands, when n>1

DTEX-FACTOR=37.5*Average-Dtex/800 (dtex as measured, specified)

Section-Modulus is reported in units of (gf/mm)

Average Decitex (Average-Dtex)

The Average Decitex Method is used to calculate the Average-Dtex on a length-weighted basis for elastic fibers present in an entire article, or in a specimen of interest extracted from an article. The decitex value is the mass in grams of a fiber present in 10,000 meters of that material in the relaxed state. The decitex value of elastic fibers or elastic laminates containing elastic fibers is often reported by manufacturers as part of a specification for an elastic fiber or an elastic laminate including elastic fibers. The Average-Dtex is to be calculated from these specifications if available. Alternatively, if these specified values are not known, the decitex value of an individual elastic fiber is measured by determining the cross-sectional area of a fiber in a relaxed state via a suitable microscopy technique such as scanning electron microscopy (SEM), determining the composition of the fiber via Fourier Transform Infrared (FT-IR) spectroscopy, and then using a literature value for density of the composition to calculate the mass in grams of the fiber present in 10,000 meters of the fiber. The manufacturer-provided or experimentally measured decitex values for the individual elastic fibers removed from an entire article, or specimen extracted from an article, are used in the expression below in which the length-weighted average of decitex value among elastic fibers present is determined.

The lengths of elastic fibers present in an article or specimen extracted from an article is calculated from overall dimensions of and the elastic fiber pre-strain ratio associated with components of the article with these or the specimen, respectively, if known. Alternatively, dimensions and/or elastic fiber pre-strain ratios are not known, an absorbent article or specimen extracted from an absorbent article is disassembled and all elastic fibers are removed. This disassembly can be done, for example, with gentle heating to soften adhesives, with a cryogenic spray (e.g. Quick-Freeze, Miller-Stephenson Company, Danbury, Conn.), or with an appropriate solvent that will remove adhesive but not swell, alter, or destroy elastic fibers. The length of each elastic fiber in its relaxed state is measured and recorded in millimeters (mm) to the nearest mm.

Calculation of Average-Dtex

For each of the individual elastic fibers f of relaxed length $L_i$ and fiber decitex value $d_i$ (obtained either from the manufacturer's specifications or measured experimentally) present in an absorbent article, or specimen extracted from an absorbent article, the Average-Dtex for that absorbent article or specimen extracted from an absorbent article is defined as:

$$\text{Average-Dtex} = \frac{\sum_{i=1}^{n}(L_i \times d_i)}{\sum_{i=1}^{n} L_i}$$

where n is the total number of elastic fibers present in an absorbent article or specimen extracted from an absorbent article. The Average-Dtex is reported to the nearest integer value of decitex (grams per 10 000 m).

If the decitex value of any individual fiber is not known from specifications, it is experimentally determined as described below, and the resulting fiber decitex value(s) are used in the above equation to determine Average-Dtex.

Experimental Determination of Decitex Value for a Fiber

For each of the elastic fibers removed from an absorbent article or specimen extracted from an absorbent article according to the procedure described above, the length of each elastic fiber $L_k$ in its relaxed state is measured and recorded in millimeters (mm) to the nearest mm. Each elastic fiber is analyzed via FT-IR spectroscopy to determine its composition, and its density $\rho_k$ is determined from available literature values. Finally, each fiber is analyzed via SEM. The fiber is cut in three approximately equal locations perpendicularly along its length with a sharp blade to create a clean cross-section for SEM analysis. Three fiber segments with these cross sections exposed are mounted on an SEM sample holder in a relaxed state, sputter coated with gold, introduced into an SEM for analysis, and imaged at a resolution sufficient to clearly elucidate fiber cross sections. Fiber cross sections are oriented as perpendicular as possible to the detector to minimize any oblique distortion in the measured cross sections. Fiber cross sections may vary in shape, and some fibers may consist of a plurality of individual filaments. Regardless, the area of each of the three fiber cross sections is determined (for example, using diameters for round fibers, major and minor axes for elliptical fibers, and image analysis for more complicated shapes), and the average of the three areas $a_k$ for the elastic fiber, in units of micrometers squared ($\mu m^2$), is recorded to the nearest 0.1 $\mu m^2$. The decitex $d_k$ of the kth elastic fiber measured is calculated by:

$$d_k = 10\,000 \text{ m} \times a_k \times \rho_k \times 10^{-6}$$

where $d_k$ is in units of grams (per calculated 10,000 meter length), $a_k$ is in units of $\mu m^2$, and $\rho_k$ is in units of grams per cubic centimeter ($g/cm^3$). For any elastic fiber analyzed, the experimentally determined $L_k$ and $d_k$ values are subsequently used in the expression above for Average-Dtex.

Open Area

Defined as the percentage of a Section not occluded by elastic strands. Un-apertured films have an Open Area 0%. Apertured film Open Area=(area occupied by apertures)/(total film area). None of today's marketed disposable absorbent articles comprising a film in one or more of a belt, sided panel, or ear panel, waistband, cuff, wing are believed to have and Open Area above 50%. Open Area is defined as:

Open Area (%)=(Average-Strand-Diameter)/Average-Strand-Spacing

Average-Pre-Strain

The Average-Pre-Strain of a specimen are measured on a constant rate of extension tensile tester (a suitable instrument is the MTS Insight using Testworks 4.0 Software, as available from MTS Systems Corp., Eden Prairie, Minn.) using a load cell for which the forces measured are within 1% to 90% of the limit of the cell. Articles are conditioned at 23° C.±2 C.° and 50%±2% relative humidity for 2 hours prior to analysis and then tested under the same environmental conditions.

Program the tensile tester to perform an elongation to break after an initial gage length adjustment. First raise the cross head at 10 mm/min up to a force of 0.05 N. Set the current gage to the adjusted gage length. Raise the crosshead at a rate of 100 mm/min until the specimen breaks (force drops 20% after maximum peak force). Return the cross head to its original position. Force and extension data is acquired at a rate of 100 Hz throughout the experiment.

Set the nominal gage length to 40 mm using a calibrated caliper block and zero the crosshead. Insert the specimen into the upper grip such that the middle of the test strip is positioned 20 mm below the grip. The specimen may be folded perpendicular to the pull axis, and placed in the grip to achieve this position. After the grip is closed the excess material can be trimmed. Insert the specimen into the lower grips and close. Once again, the strip can be folded, and then trimmed after the grip is closed. Zero the load cell. The specimen should have a minimal slack but less than 0.05 N of force on the load cell. Start the test program.

From the data construct a Force (N) verses Extension (mm). The Average-Pre-Strain is calculated from the bend in the curve corresponding to the extension at which the nonwovens in the elastic are engaged. Plot two lines, corresponding to the region of the curve before the bend (primarily the elastics), and the region after the bend (primarily the nonwovens). Read the extension at which these two lines intersect, and calculate the % Pre-Strain from the extension and the corrected gage length. Record as % Pre-strain 0.1%. Calculate the arithmetic mean of three replicate samples for each elastomeric laminate and Average-Pre-Strain to the nearest 0.1%.

Force Relaxation Over Time

The Force Relaxation over Time of a specimen is measured on a constant rate of extension tensile tester (a suitable instrument is the MTS Insight using Testworks 4.0 Software, as available from MTS Systems Corp., Eden Prairie, Minn.) using a load cell for which the forces measured are within 1% to 90% of the limit of the cell. Articles are conditioned at 23° C.±2 C.° and 50%±2% relative humidity for 2 hours prior to analysis and then tested under the same environmental conditions. Prepare a sample size such that it enables a gauge length of 25.4 mm (parallel to the elastic stretch) at a width of 12.7 mm.

Program the tensile tester to perform an elongation to determine the engineering strain at which the tensile force reaches 0.0294 N/mm.

Prepare and condition a second sample as described above for the Force Relaxation over time test. The test is performed on the same equipment as described above. It is performed at a temperature of 37.8° C. Extend the sample to the strain as determined above. Hold the sample for 10 hours and record the force at a rate of 100 Hz throughout the experiment a chart showing the data for an extruded strand prior art product and an inventive elastomeric laminate comprising beam elastic as described herein is show in FIG. 23.

CONCLUSION

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. An absorbent article, comprising:
 a front waist region, a back waist region, and a crotch region therebetween;
 a chassis comprising a topsheet, a backsheet and an absorbent core disposed between the topsheet and the backsheet, wherein the chassis comprises a front end edge, a back end edge, and a pair of laterally opposing side edges;
 a back belt disposed in the back waist region overlapping and extending outboard of the back end edge of the chassis to form a back waist edge;
 a front belt disposed in the front waist region overlapping and extending outboard of the front end edge of the chassis to form a front waist edge;
 wherein the front belt is joined to the back belt at or adjacent the laterally opposing belt side edges to form leg openings and a waist opening to form a closed-form pant;
 a longitudinal axis extending from the midpoint of the front waist edge to the midpoint of the back waist edge;
 a lateral axis extending perpendicular to the longitudinal axis through the midpoint of the longitudinal axis;
 wherein the back belt comprises a first plurality of elastics comprising greater than about 40 elastic strands, and wherein the front belt comprises a second plurality of elastics comprising greater than about 40 elastic strands;
 wherein the first plurality of elastics has an Average-Strand-Spacing of less than 4 mm, and wherein the second plurality of elastics has an Average-Strand-Spacing of less than 4 mm;
 wherein the Product Hip-to-Waist Silhouette is from about 0.8 to about 1.1;
 wherein the Product Waist-to-Crotch Silhouette is from about 0.8 to about 2.0; and
 wherein the absorbent article has a Relaxed Product Waist Width from about 80 mm to about 270 mm and a Relaxed Product Hip Width from about 80 mm to about 300 mm.

2. The absorbent article of claim 1, wherein the absorbent article has a Relaxed Product Waist Width from about 170 mm to about 270 mm and a Relaxed Product Hip Width from about 170 to about 300 mm.

3. The absorbent article of claim 1, wherein the absorbent article has a Relaxed Product Waist Width from about 80 mm to about 180 mm and a Relaxed Product Hip Width from about 80 mm to about 200 mm.

4. The absorbent article of claim 1, wherein the first plurality of elastics comprises greater than about 70 elastic strands, and wherein the second plurality of elastics comprises greater than about 50 elastic strands.

5. The absorbent article of claim 1, wherein the first plurality of elastics has an Average-Strand-Spacing of less than 3 mm, and wherein the second plurality of elastics has an Average-Strand-Spacing of less than 3 mm.

6. The absorbent article of claim 1, wherein the Average-Dtex of the first plurality of elastics is from about 10 to about 500, and wherein the Average-Dtex of the second plurality of elastics is from about 10 to about 500.

7. The absorbent article of claim 1, wherein the Pressure-Under-Strand of the first plurality of elastics is from about 0.1 to about 1 psi, and wherein the Pressure-Under-Strand of the second plurality of elastics is from about 0.1 to about 1 psi.

8. The absorbent article of claim 1, wherein the back belt is divided into 4 equal sections arranged longitudinally, wherein Section 4 comprises a proximal end edge of the back belt, Section 1 comprises a distal end edge of the back belt and forms the back waist edge, Section 2 is proximate to Section 1 and Section 3 is proximate to Section 4, wherein at least two of the sections each have greater than 10 elastic strands; and
 wherein the front belt is divided into 4 equal sections arranged longitudinally, wherein Section 4 comprises a proximal end edge of the front belt, Section 1 comprises a distal end edge of the front belt and forms the front waist edge, Section 2 is proximate to Section 1 and Section 3 is proximate to Section 4, wherein at least two of the sections each have greater than 10 elastic strands.

9. The absorbent article of claim 8, wherein Section 1 of the back belt is longitudinally longer than Section 1 of the front belt.

10. The absorbent article of claim 1, wherein the first plurality of elastics of the back belt are between an inner and an outer nonwoven, and wherein the second plurality of elastics of the front belt are between an inner and an outer nonwoven, and wherein the inner nonwoven of the front belt and the inner nonwoven of the back belt are separate and distinct and longitudinally spaced from each other, and wherein the outer nonwoven of the front belt and the outer nonwoven of the back belt are separate and distinct and longitudinally spaced from each other.

11. An absorbent article, comprising:
 a front waist region, a back waist region, and a crotch region therebetween;
 a chassis comprising a topsheet, a backsheet and an absorbent core disposed between the topsheet and the backsheet, wherein the chassis comprises a front end edge, a back end edge, and a pair of laterally opposing side edges;

a back belt disposed in the back waist region overlapping and extending outboard of the back end edge of the chassis to form a back waist edge;

a front belt disposed in the front waist region overlapping and extending outboard of the front end edge of the chassis to form a front waist edge;

wherein the front belt is joined to the back belt at or adjacent the laterally opposing belt side edges to form leg openings and a waist opening to form a closed-form pant;

a longitudinal axis extending from the midpoint of the front waist edge to the midpoint of the back waist edge;

a lateral axis extending perpendicular to the longitudinal axis through the midpoint of the longitudinal axis;

wherein the back belt comprises a first plurality of elastics comprising greater than about 60 elastic strands, and wherein the front belt comprises a second plurality of elastics comprising greater than about 60 elastic strands;

wherein the first plurality of elastics has an Average-Strand-Spacing of less than 4 mm, and wherein the second plurality of elastics has an Average-Strand-Spacing of less than 4 mm;

wherein the Product Hip-to-Waist Silhouette is from about 0.8 to about 1.08;

wherein the Product Waist-to-Crotch Silhouette is from about 0.8 to about 2.8; and wherein the absorbent article has a Relaxed Product Waist Width from about 200 mm to about 400 mm and a Relaxed Product Hip Width from about 200 mm to about 450 mm.

12. The absorbent article of claim 11, wherein the absorbent article has a Relaxed Product Waist Width from about 300 mm to about 400 mm and a Relaxed Product Hip Width from about 300 mm to about 450 mm.

13. The absorbent article of claim 11, wherein the absorbent article has a Relaxed Product Waist Width from about 200 mm to about 300 mm and a Relaxed Product Hip Width from about 200 mm to about 350 mm.

14. The absorbent article of claim 11, wherein the first plurality of elastics comprises greater than about 80 elastic strands, and wherein the second plurality of elastics comprises greater than about 80 elastic strands.

15. The absorbent article of claim 11, wherein the first plurality of elastics has an Average-Strand-Spacing of less than 2.5 mm, and wherein the second plurality of elastics has an Average-Strand-Spacing of less than 2.5 mm.

16. The absorbent article of claim 11, wherein the Average-Dtex of the first plurality of elastics is from about 10 to about 500, and wherein the Average-Dtex of the second plurality of elastics is from about 10 to about 500.

17. The absorbent article of claim 11, wherein the Pressure-Under-Strand of the first plurality of elastics is from about 0.1 to about 1 psi, and wherein the Pressure-Under-Strand of the second plurality of elastics is from about 0.1 to about 1 psi.

18. The absorbent article of claim 11, wherein the back belt is divided into 4 equal sections arranged longitudinally, wherein Section 4 comprises a proximal end edge of the back belt, Section 1 comprises a distal end edge of the back belt and forms the back waist edge, Section 2 is proximate to Section 1 and Section 3 is proximate to Section 4, wherein at least two of the sections each have greater than 20 elastic strands; and wherein the front belt is divided into 4 equal sections arranged longitudinally, wherein Section 4 comprises a proximal end edge of the front belt, Section 1 comprises a distal end edge of the front belt and forms the front waist edge, Section 2 is proximate to Section 1 and Section 3 is proximate to Section 4, wherein at least two of the sections each have greater than 20 elastic strands.

19. The absorbent article of claim 11, wherein the first plurality of elastics of the back belt are between an inner and an outer nonwoven, and wherein the second plurality of elastics of the front belt are between an inner and an outer nonwoven, and wherein the inner nonwovens of the front and back belts are separate and distinct and longitudinally spaced from each other, and wherein the outer nonwovens of the front and back belts are a common nonwoven layer that extends continuously longitudinally from the front waist edge to the back waist edge.

20. The absorbent article of claim 11, wherein the first plurality of elastics of the back belt are between an inner and an outer nonwoven, and wherein the second plurality of elastics of the front belt are between an inner and an outer nonwoven, and wherein the inner nonwovens of the front and back belts are a common nonwoven layer that extends continuously longitudinally from the front waist edge to the back waist edge, and wherein the outer nonwovens of the front and back belts are a common nonwoven layer that extends continuously longitudinally from the front waist edge to the back waist edge.

* * * * *